US007888467B2

(12) United States Patent
Martin et al.

(10) Patent No.: US 7,888,467 B2
(45) Date of Patent: Feb. 15, 2011

(54) BACTERIAL EFFECTOR PROTEINS WHICH INHIBIT PROGRAMMED CELL DEATH

(75) Inventors: Gregory B. Martin, Ithaca, NY (US); Robert B. Abramovitch, Ithaca, NY (US); Nai-Chun Lin, Ithaca, NY (US); Young-Jin Kim, Seoul (KR)

(73) Assignee: Boyce Thompson Institute for Plant Research, Ithaca, NY (US)

( * ) Notice: Subject to any disclaimer, the term of this patent is extended or adjusted under 35 U.S.C. 154(b) by 47 days.

(21) Appl. No.: 10/524,750

(22) PCT Filed: Aug. 13, 2003

(86) PCT No.: PCT/US03/25247
§ 371 (c)(1), (2), (4) Date: Jul. 25, 2005

(87) PCT Pub. No.: WO2004/016745
PCT Pub. Date: Feb. 26, 2004

(65) Prior Publication Data
US 2006/0035230 A1 Feb. 16, 2006

Related U.S. Application Data

(60) Provisional application No. 60/404,339, filed on Aug. 16, 2002, provisional application No. 60/425,842, filed on Nov. 12, 2002.

(51) Int. Cl.
C07K 14/00 (2006.01)
(52) U.S. Cl. .................................................. 530/350
(58) Field of Classification Search ................. 800/278
See application file for complete search history.

(56) References Cited

U.S. PATENT DOCUMENTS

| | | | |
|---|---|---|---|
| 4,237,224 A | 12/1980 | Cohen et al. | |
| 4,945,050 A | 7/1990 | Sanford et al. | |
| 5,034,322 A | 7/1991 | Rogers et al. | |
| 5,036,006 A | 7/1991 | Sanford et al. | |
| 5,100,792 A | 3/1992 | Sanford et al. | |
| 5,352,605 A | 10/1994 | Fraley et al. | |
| 5,750,385 A | 5/1998 | Shewmaker et al. | |
| 5,837,838 A * | 11/1998 | Reed et al. ............... | 536/23.1 |
| 6,002,068 A | 12/1999 | Privalle et al. | |
| 6,211,437 B1 * | 4/2001 | Briggs et al. ............. | 800/298 |

OTHER PUBLICATIONS

Lacomme et al, Bax-induced cell death in tobaco is similar to the hypersensitive response, 1999, PNAS, vol. 96, pp. 7956-7961.*
Andersen, Does neuronal loss in Parkinson's disease involve programmed cell death?, 2001, Bioessays, vol. 23, pp. 640-646.*
Managan et al, Stimulation of human monocytes by endotoxin associated protein: inhibition of programmed cell death (apoptosis) and potential significance in adjuvancity, 1992, Infection and immunity, vol. 60, pp. 1684-1686.*
Fouts et al, Genomewide identification of *Pseudomonas syringae* pv tomato dc3000 promoters controlled by the HrpL alternative sigma factor, 2002, PNAS, vol. 99, pp. 2275-2280.*
Kim et al, Two distinct pseudomonas effector proteins interact with the Pto kinase and activate plant immunity, 2002, vol. 109, pp. 589-598.*
Aoyama et al., "A Glucocorticoid-Mediated Transcriptional Induction System in Transgenic Plants," *Plant J.* 11:605-612 (1997).
Ausubel et al., Current Protocols in Molecular Biology, John Wiley & Sons, New York, New York (1989) (Cover Page and Table of Contents Only).
Bogdanove et al., "AvrPto-Dependent Pto-Interacting Proteins and AvrPto-Interacting Proteins in Tomato," *Proc. Natl. Acad. Sci. USA* 97(16):8836-8840 (2000).
Bourouis & Jarry, "Vectors Containing a Prokaryotic Dihydrofolate Reductase Gene Transform *Drosophila* Cells to Methotrexate-Resistance," *EMBO J.* 2(7):1099-1104 (1983).
Chang et al., "*avrPto* Enhances Growth and Necrosis Caused by*Pseudomonas syringae* pv. Tomato in Tomato Lines Lacking Either Pto and Prf," *Mol. Plant-Microbe Interact.* 13(5):568-571 (2000).
Chang et al., "Functional Studies of the Bacterial Avirulence Protein AvrPto by Mutational Analysis," *Mol. Plant-Microbe Interact.* 14(4):451-459 (2001).
Chen et al., "The *Pseudomonas syringae avrRpt2* Gene Product Promotes Pathogen Virulence from Inside Plant Cells," *Mol. Plant Microbe. Interact.* 13(12):1312-1321 (2000).
Clifton et al., "NF-κB-Dependent Inhibition of Apoptosis is Essential for Host Cellsurvival During *Rickettsia rickettsii* Infection," *Proc. Natl. Acad. Sci. USA* 95:4646-4651 (1998).
Clough et al., "The *Arabidopsis dnd1* "Defense, No Death" Gene Encoded a Mutated Cyclic Nucleotide-Gated Ion Channel," *Proc. Natl. Acad. Sci. USA* 97(16):9323-9328 (2000).

(Continued)

*Primary Examiner*—Mark Navarro
(74) *Attorney, Agent, or Firm*—Nixon Peabody LLP

(57) ABSTRACT

The present invention relates to a bacterial effector protein which inhibits programmed cell death in eukaryotes and a nucleic acid molecule encoding such a protein. The present invention also relates to methods of suppressing programmed cell death in eukaryotes, delaying senescence in plants, and increasing protein expression in plants. The present invention further relates to a nucleic acid construct having a nucleic acid molecule encoding a first protein, which suppresses immunity by inhibition of programmed cell death in eukaryotes, coupled to a nucleic acid molecule encoding a second protein which is toxic when expressed in eukaryotes. Additionally, the present invention provides a method of stabilizing a transgenic plant transformed with such a nucleic acid construct. Finally, the present invention provides a method of treating subjects for a condition mediated by programmed cell death involving administering to the subject a bacterial effector protein which inhibits programmed cell death.

5 Claims, 22 Drawing Sheets

PUBLICATIONS

Cohn et al., "Innate Immunity in Plants," *Curr. Opin. Immunol.* 13:55-62 (2001).

Collmer et al., "*Pseudomonas syringae* Hrp Type III Secretion System and Effector Proteins," *Proc. Natl. Acad. Sc. USA* 97(16):8770-8777 (2000).

Dangl & Jones, "Plant Pathogens and Integrated Defense Responses to Infection," *Nature* 411:826-833 (2001).

Del Pozo et al., "Caspases and Programmed Cell Death in the Hypersensitive Response of Plants to Pathogens," *Curr. Biol.* 8:1129-1132 (1998).

Evans et al., Handbook of Plant Cell Cultures, vol. 1, MacMillan Publishing Co., New York (1983) (Cover Page and Table of Contents Only).

Fouts et al., "Genomewide Identification of *Pseudomonas syringae* pv. *Tomato* DC3000 Promoters Controlled by the HrpL Alternative Sigma factor," *Proc. Natl. Acad. Sci. USA* 99:2275-2280 (2002).

Fraley et al., "Entrapment of Bacterial Plasmid in Phospholipid Vesicles: Potential for Gene Transfer," *Proc. Natl. Acad. Sci. USA* 76(7):3348-3352 (1979).

Fraley et al., "Expression of Bacterial Genes in Plant Cells," *Proc. Natl. Acad. Sci. USA* 80:4803-4807(1983).

Frederick et al., "Recognition Specificity for the Bacterial Avirulence Protein AvrPto is Determined by Thr-204 in the Activation Loop of the Tomato Pto Kinase," *Mol. Cell.* 2:241-245 (1998).

Fromm et al., "Expression of Genes Transferred Into Monocot and Dicot Plat Cells by Electroporation," *Proc. Natl. Acad. Sci. USA* 82:5824-5828 (1985).

Galán et al., "Type III Secretion Machines: Bacterial Devices for Protein Delivery Into Host Cells," *Science* 284:1322-1328 (1999).

GenBank Accession No. AF141883 (Sep. 16, 1999).

GenBank Accession No. AY074795 (Feb. 5, 2002).

Geng et al., "*Chlamydia pneumoniae* Inhibits Apoptosis in Human Peripheral Blood Mononuclear Cells Through Induction of IL-10," *J. Immunol.* 164:5522-5529 (2000).

Greenberg, J.T., "Programmed Cell Death in Plant-Pathogen Interactions," *Annu. Rev. Plant Physiol. Plant Mol. Biol.* 48:525-545 (1997).

Goodman et al., "The Hypersensitive Reaction in Plants to Pathogens," APS Press, St. Paul, Minnesota, USA (1994) (Cover Page and Table of Contents Only).

Guttman et al., "A Functional Screen for the Type III (Hrp) Secretome of the Plant Pathogen *Pseudomonas syringae*," *Science* 295:1722-1726 (2002).

Guttman et al., "Functional Analysis of the Type III Effectors Avr-Rpt2 and AvrRpm1 of *Pseudomonas syringae* with the Use of Single-Copy Genomic Integration System," *Mol. Plant Microbe. Interact.* 14:145-155 (2001).

Heath, M.C., "Hypersensitive Response-Related Death," *Plant Mol. Biol.* 44:321-334 (2000).

Hoffman et al., "Phylogenetic Perspectives in Innate Immunity," *Science* 284:1313-1318 (1999).

Innes et al., "Molecular Analysis of Avirulence Gene *avrRpt2* and Identification of a Putative Regulatory Sequence Common to All Known *Pseudomonas syringae* Avirulence Genes," *J. Bacteriol.* 175:4859-4869 (1993).

Jackson et al., "Identification of a Pathogenicity Island, Which Contains Genes for Virulence and Avirulence, on a Large Native Plasmid in the Bean Pathogen *Pseudomonas syringae* Pathovar Phaseolicola," *Proc. Natl. Acad. Sci. USA* 96:10875-10880 (1999).

Jefferson et al., "GUS Fusions: β-Glucuronidase as a Sensitive and Versatile Gene Fusion Marker in Higher Plants," *EMBO J.* 6(13):3901-3907 (1987).

Jia et al., "Alleles of *Pto* and *Fen* Occur in Bacterial Speck-Susceptible and Fenthion-Insensitive Tomato Cultivars and Encode Active Protein Kinase," *Plant Cell* 9:61-73 (1997).

Jin et al., "Role of the Hrp Pilus in Type III Protein Secretion in *Pseudomonas syringae*," *Science* 294:2556-2558 (2001).

Jones et al., "Isolation of the Tomato *Cf-9* Gene for Resistance to *Cladosporium fulvum* by Transposon Tagging," *Science* 266:789-793 (1994).

Jürgensmeier et al., "Bax Directly Induces Release of Cytochrome c from Isolated Mitochondria," *Proc. Natl. Acad. Sci. USA* 95:4997-5002 (1998).

Juris et al., "Yersinia Effectors Target Mammalian Signalling Pathways," *Cell Microbiol.* 4(4):201-211 (2002).

Kampranis et al., "A Novel Plant Glutathione S-Transferase/Peroxidase Suppresses Bax Lethality in Yeast," *J. Biol. Chem.* 275:29207-29216 (2000).

Kawai et al., "Evolutionally Conserved Plant Homologue of the Bax Inhibitor-1 (BI-1) Gene Capable of Suppressing Bax-Induced Cell Death in Yeast," *FEBS Lett.* 464:143-147 (1999).

Kawai-Yamada et al., "Mammalian Bax-Induced Plant Cell Death Can Be Down-Regulated by Overexpression of *Arabidopsis Bax Inhibitor-1 (AtBI-1)*," *Proc. Natl. Acad. Sci. USA* 98(21):12295-12300 (2001).

Keen et al , "Improved Broad-Host-Range Plasmids for DNA Cloning in Gram-Negative Bacteria," *Gene* 70:191-197 (1988).

Kim et al., "Two Distinct *Pseudomonas* Effector Proteins Interact with the Pto Kinase and Activate Plant Immunity," *Cell* 109:589-598 (2002).

Kjemtrup et al., "Effector Proteins of Phytopathogenic Bacteria: Bifunctional Signals in Virulence and Host Recognition," *Curr. Opin. Microbiol.* 3:73-78 (2000).

Knodler et al., "*Salmonella* and Apoptosis: To Live or Let Die?" *Microbes Infect.* 3:1321-1326 (2001).

Krens et al., "In vitro Transformation of Plant Protoplasts with Ti-plasmid DNA," *Nature* 296:72-74 (1982).

Lacomme et al., "Bax-Induced Cell Death in Tobacco is Similar to the Hypersensitive Response," *Proc. Natl. Acad. Sci. USA* 96:7956-7961 (1999).

Lam et al., "Caspase-Like Protease Involvement in the Control of Plant Cell Death," *Plant Mol. Biol.* 44:417-428 (2000).

Lindgren, P.B., "The Role of *hrp* Genes During Plant-Bacterial Interaction," *Annu. Rev. Phytopathol.* 35:129-152 (1997).

Martin et al., "A Member of Tomato *Pto* Gene Family Confers Sensitivity to Fenthion Resulting in Tomato," *Plant Cell* 6:1543-1552 (1994).

Martin et al., "Map-Based Cloning of a Protein Kinase Gene Conferring Disease Resistance in Tomato," *Science* 262:1432-1436 (1993).

Massari et al., "*Neisseria Meningitidis* Porin PorB Interacts with Mitochondria and Protects Cells from Apoptosis," *Proc. Natl. Acad. Sci. USA* 97(16):9070-9075 (2000).

Michelmore & Meyers, "Clusters of Resistance Genes in Plants Evolve by Divergent Selection and a Birth-and-Death Process," *Genome Res.* 8:1113-1130 (1998).

Mudgett & Staskawicz, "Characterization of the *Pseudomonas syringae* pv. *Tomato* AvrRpt2 Protein: Demonstration of Secretion and Processing During Bacterial Pathogenesis," *Mol. Microbiol.* 32:927-941 (1999).

Mumberg et al., "Regulatable Promoters of *Saccharomyces cerevisiae*: Comparison of Transcriptional Activity and Their Use for Heterologous Expression," *Nucleic Acids Res.* 22:5767-5768 (1994).

Nimchuk et al., "Eukaryotic Fatty Acylation Drives Plasma Membrane Targeting and Enhances Function of Several Type III Effector Proteins from *Pseudomonas syringae*," *Cell* 101:353-363 (2000).

Rathjen et al., "Constitutively Active *Pto* Induces a *Prf*-Dependent Hypersensitive Response in the Absence of *avrPto*," *EMBO J.* 18:3232-3240 (1999).

Reuber & Ausubel, "Isolation of Arabidopsis Genes That Differentiate Between Resistance Responses Mediated by the *PRS2* and *RPM1* Disease Resistance Genes," *Plant Cell* 8:241-249 (1996).

Riely & Martin, "Ancient Origin of Pathogen Recognition Specificity Conferred by the Tomato Disease Resistance Gene *Pto*," *Proc. Natl. Acad. Sci. USA* 98(4):2059-2064 (2001).

Ritter & Dangl, "Interference Between Two Specific Pathogen Recognition Events Mediated by Distinct Plant Disease Resistance Genes," *Plant Cell* 8:251-257 (1996).

Ronald et al., "The Cloned Avirulence Gene *avrPto* Induces Disease Resistance in Tomato Cultivars Containing the *Pto* Resistance Gene," *J. Bacteriol.* 174:1604-1611 (1992).

Sambrook et al., Molecular Cloning: A Laboratory Manual, 2$^{nd}$ ed., Cold Spring Harbor, New York, Cold Spring Harbor Laboratory Press (1989).

Salmeron et al., "Molecular Characterization and *hrp* Dependence of the Avirulence Gene *avrPto* from *Pseudomonas syringae* pv. Tomato," *Mol. Gen. Genet.* 239:6-16 (1993).

Salmeron et al., "Tomato Mutants Altered in Bacterial Disease Resistance Provide Evidence for a new Locus Controlling Pathogen Recognition," *Plant Cell* 6:511-520 (1994).

Salmeron et al., "Tomato *Prf* is a Member of the Leucine-Rich Repeat Class of Plant Disease Resistance Genes and Lies Embedded Within the *Pto* Kinase Gene Cluster," *Cell* 86:123-133 (1996).

Schena et al., "A Steroid-Inducible Gene Expression System for Platn Cells," *Proc. Natl. Acad. Sci. USA* 88:10421-10425 (1991).

Scofield et al., "Molecular Basis of Gene-For-Gene Specificity in Bacterial Speck Disease of Tomato," *Science* 274:2063-2065 (1996).

Sessa et al., "Signal Recognition and Transduction Mediated by the Tomato Pto Kinase: A Paradigm of Innate Immunity in Plants," *Microbes Infect.* 2:1591-1597 (2000).

Sessa et al., "Thr38 and Ser198 are Pto Autophosphorylation Sites Required for the AvrPto—Pto-Mediated Hypersensitive Response," *EMBO J.* 19:2257-2269 (2000).

Shan et al., "A Cluster of Mutations Disrupt the Avirulence But not the Virulence Function of AvrPto," *Mol. Plant-Microbe Interact.* 13:592-598 (2000).

Shan et al., "The Pseudomonas AvrPto Protein is Differentially Recognized by Tomato and Tobacco and Is Localized to the Plant Plasma Membrane," *Plant Cell* 12:2323-2337 (2000b).

Studier, "Use of T7 RNA Polymerase to Direct Expression of Cloned Genes," *Methods Enzymol.* 185:60-89 (1990).

Tang et al., "Overexpression of *Pto* Activates Defense Responses and Confers Broad Resistance," *Plant Cell* 11:15-30 (1999).

Tang et al., "Initiation of Plant Disease Resistance by Physical Interaction of AvrPto and Pto Kinase," *Science* 274:2060-2063 (1996).

Tsiamis et al., "Cultivar-Specific Avirulence and Virulence Functions Assigned to *avrPphF* in *Pseudomonas syringae* pv. *phaseolicola*, the Cause of Bean Halo-Blight Disease," *EMBO. J.* 19:3204-3214 (2000).

Van Der Ackerveken et al., "Recognition of the Bacterial Avirulence Protein AvrBs3 Occurs Inside the Host Cell," *Cell* 87:1307-1316 (1996).

Van Der Hoorn et al., "Agroinfiltration is a Versatile Tool That Facilitates Comparative Analyses of *Avr9/Cf*-9-Induced and *Avr4/Cf*-4-Induced Necrosis," *MPMI* 13(4):439-446 (2000).

Van Kan et al., "Cloning and Characterization of cDNA of Avirulence Gene *avr9* of the Fungal Pathogen *Cladosporium fulvum*, Causal Agent of Tomato Leaf Mold," *MPMI* 4(1):52-59 (1991).

Vasil, I.R. (ed.), Cell Culture and Somatic Cell Genetics of Plants, Acad. Press, Orlando, vol. I (1984).

Vasil, I.R. (ed.), Cell Culture and Somatic Cell Genetics of Plants, Acad. Press, Orlando, vol. III (1986).

White et al., "Prospects for Understanding Avirulence Gene Function," *Curr. Opin. Plant Biol.* 3:291-298 (2000).

Windgassen et al., "Rapid Gene Inactivation in *Pseudomonas aeruginosa*," *FEMS Microbiol. Lett.* 193:201-205 (2000).

Xiao et al., "Identification of a Putative Alternate Sigma Factor and Characterization of a Multicomponent Regulatory Cascade Controlling the Expression of *Pseudomonase syringae* pv. syringae Pss61 *hrp* and *hrmA* Genes," *J. Bacteriol.* 176(4):1025-1036 (1994).

Yu et al., "Gene-For-Gene Disease Resistance Without the Hypersensitive Response in *Arabidopsis dnd1* Mutant," *Proc. Natl. Acad. Sci. USA* 95:7819-7824 (1998).

Zhou et al., "The Tomato Gene *Pti1* Encodes a Serine/Threonine Kinase That is Phosphorylated by Pto and Is Involved in the Hypersensitive Response," *Cell* 83:925-935 (1995).

Zhu et al., "The C Terminus of AvrXa10 Can Be Replaced by the Transcriptional Activation Domain of VP 16 from the Herpes Simplex Virus," *Plant Cell* 11:1665-1674 (1999).

Ambramovitch et al., "*Pseudomonas* Type III Effector AvrPtoB Induces Plant Disease Susceptibility by Inhibition of Host Programmed Cell Death," EMBO 22(1):60-69 (2003).

Greenberg, "Programmed Cell Death: A Way of Life for Plants," Proc. Natl. Acad. Sci. USA 93:12094-12097 (1996).

International Search Report for International Patent Application No. PCT/US03/25247 (Jul. 8, 2008).

Reed, "Apoptosis-Based Therapies," Nat. Rev. 1:111-121 (2002).

\* cited by examiner

|  | RG-PtoR (Pto/Pto, Prf/Prf) | RG-Prf3 (Pto/Pto, Prf3/Prf3) | RG-Pto11 (pto11/pto11, Prf/Prf) | RG-ptoS (pto/pto, Prf/Prf) |
|---|---|---|---|---|
| AvrPtoB | + | − | − | − |
| Δ4 | − | − | − | − |
| Δ6 | + | − | + | −* |
| Δ7 | + | − | − | − |

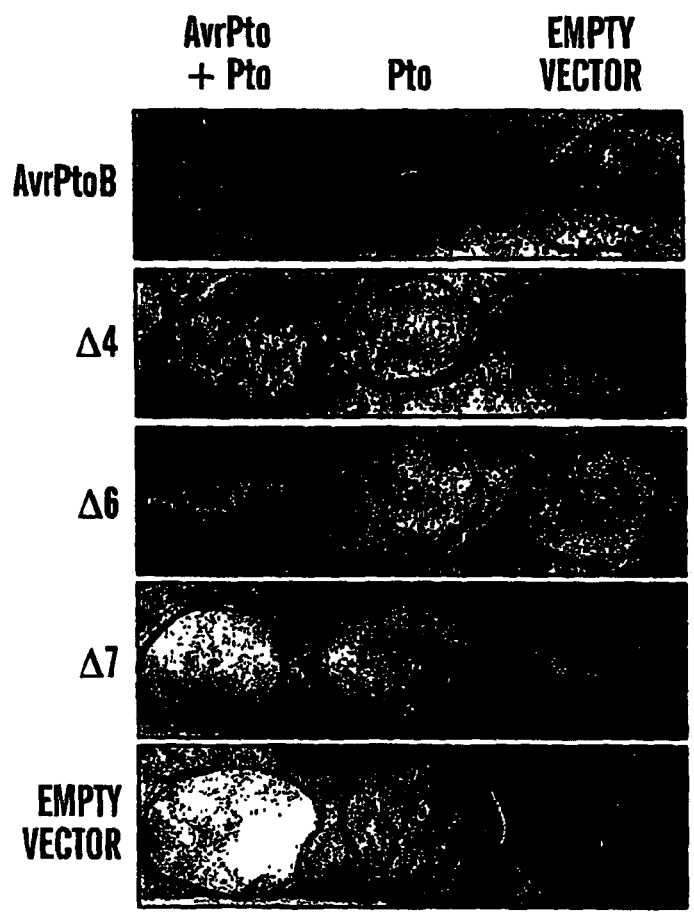
FIG. 4A
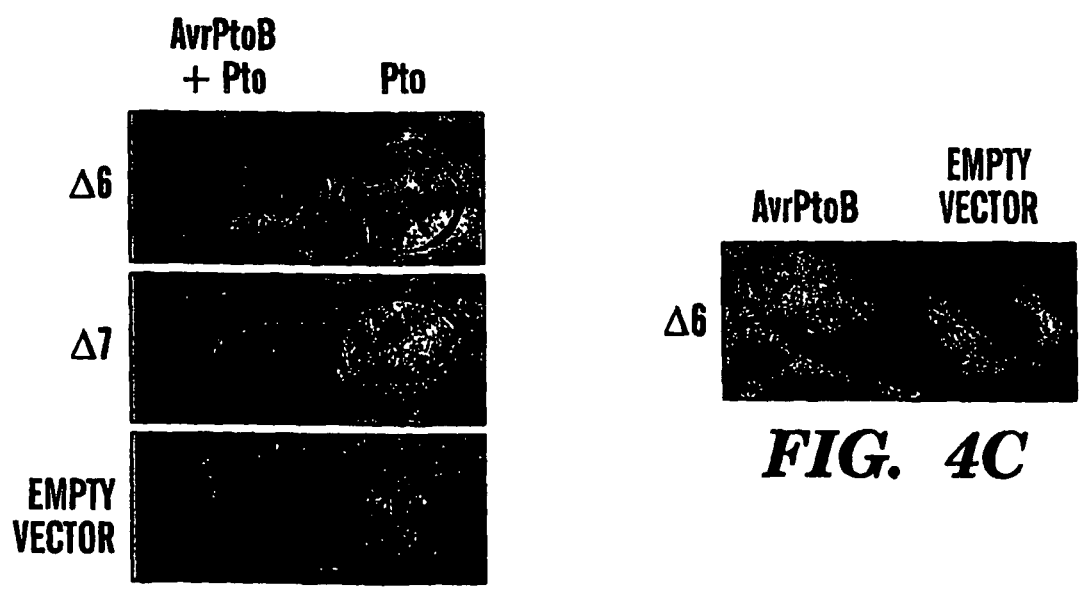
FIG. 4B
FIG. 4C

|  | RG-PtoR (Pto/Pto, Prf/Prf) | RG-prf3 (Pto/Pto, prf3/prf3) | RG-pto11 (pto11/pto11, Prf/Prf) | RG-ptoS (pto/pto, Prf/Prf) |
|---|---|---|---|---|
| AvrPtoB | I | D | D | D |
| mut1 | I | D | D | D |
| mut2 | I | D | D | D |
| mut3 | I | D | D | D |
| mut5 | I | D | I | D |

FIG. 7A

```
                                                                                                        Majority
     MAGINGAGPSGAYFVGHTDP  Majority                    - REMLLRARPLSRQTREWVA
                   10            20                                70             80
1    MAGIN GAGPSGAYFVGHTDP  DC3000          61   GRERLSRSTALSRQTREWLE   DC3000
1    MAGIN RAGPSGAYFVGHTDP  T1              57   -REMLLRARPLSRQTREWVA   T1
1    MAGIN GAGPSGAYFVGHTDP  PT23            57   -REMLLRARPLSRQTREWVA   PT23
1    MAGIN GAGPSGAYFVGHTDP  JL1065          57   -REMLLRARPLSRQTREWVA   JL1065

EPASGGAHGSSSGASSSNSP   Majority             QGMPPTAEAGVPIRPQESAE   Majority
                   30            40                                90            100
21   EPVSGQAHGSGSSGASSSNSP  DC3000          81   QGMPTAEDASVRRRPQVTAD   DC3000
21   EPASGGAHGSSSGARSSNSP   T1              76   QGMPPTAEAGVPIRPQESAE   T1
21   EPASGGAHGSSSGASSSNSP   PT23            76   QGMPPTAEAGVPIRPQESAE   PT23
21   EPASGGAHGSSSGASSSNSP   JL1065          76   QGMPPTAEAGVPIRPQESAE   JL1065

RL-PAPPDAPAPASQARDR-   Majority             AAAPQARAEERHTPEADAAA   Majority
                   50            60                               110           120
41   QVQPRPSNTPPSNAPAPPPT   DC3000         101   AATP-I-RAEARRTPEATADA  DC3000
41   RL-PAPPDAPAPASQARDR-   T1              96   AAAPQARAEERHTPEADAAA   T1
41   RL-PAPPDAPAPASQARDR-   PT23            96   AAAPQARAEERHTPEADAAA   PT23
41   RL-PAPPDAPAPASQARDR-   JL1065          96   AAAPQARAEERHTPEADAAA   JL1065
```

Majority: RSTVPPTSTESSSGSNQRTL

| pos | DC3000 | T1 | PT23 | JL1065 |
|---|---|---|---|---|
| 215/236 | ----PASPAASSSGSQRSL | RSTVPPTSTLSSSGSNQRTL | RSTVPPTSTESSSGSNQRTL | RSTVPPTSTESSSGSNQRTL |

Majority: GANRVVMRNHGNNEADA--

| 268/296 | -RVDRAAMRNRGNDEADA-- | GANRVVMRNHGNNEADA-- | GANRVVMRNHGNNEADA-- | GANRVVMRNHGNNEADA-- |

Majority: LGRFAGLMTPNQRRPSSASN

| 231/256 | FGRFARLVAPNQGRS---N | LGRFAGLMTPNQRRPSSASN | LGRFAGLMTPNQRRPSSASN | LGRFAGLMTPNQRRPSSASN |

Majority: ALQGLAQQGVDMEDLRAALE

| 285/313 | AIRGLVQQGVNLEHLRTALE | ALQGLAQQGVDMEDLRAALE | ALQGLAQQGVDMEDLRAALE | ALQGLAQQGVDMEDLRAALE |

Majority: ASASQRPVDRSPPRVNQVPT

| 248/276 | TAASQTPVDRSPPRVNQRPI | ASASQRPVDRSPPRVNQVPT | ASASQRPVDRSPPRVNQVPT | ASASQRPVDRSPPRVNQVPT |

Majority: RHILHRRPIPMDIAYALQGV

| 305/333 | RHVMQRLPIPLDIGSALQNV | RHILHRRPIPMDIAYALQGV | RHILHRRPIPMDIAYALQGV | RHILHRRPIPMDIAYALQGV |

```
                                                            Putative Hrp-box
   1 ACAGTTCCCCAGGGTGAATAGGGAAAGGTGTGATggaactCTTTCGTGCTCTTTTGCCaC
  61 ACAGCGCTGATCTTGCGGGTGATTCGGTCCGCAGGCAGAAGATCGGAGAGGATCAGCAT
 121 ATGGCGGGTATCAATAGAGCGGGACCATCGGGCGCTTATTTTGTTGGCCACACAGACCCC
   1  M  A  G  I  N  R  A  G  P  S  G  A  Y  F  V  G  H  T  D  P
 181 GAGCCAGTATCGGGGCAAGCACACGGATCCGGCAGCGGCGCCAGCTCCTCGAACAGTCCG
  21  E  P  V  S  G  Q  A  H  G  S  G  S  G  A  S  S  S  N  S  P
 241 CAGGTTCAGCCGCGACCCTCGAATACTCCCCCGTCGAACGCGCCCGCACCGCCGCCAACC
  41  Q  V  Q  P  R  P  S  N  T  P  P  S  N  A  P  A  P  P  P  T
 301 GGACGTGAGAGGCTTTCACGATCCACGGCGCTGTCGCGCCAAACCAGGGAGTGGCTGGAG
  61  G  R  E  R  L  S  R  S  T  A  L  S  R  Q  T  R  E  W  L  E
 361 CAGGGTATGCCTACAGCGGAGGATGCCAGCGTGCGTCGTAGGCCACAGGTGACTGCCGAT
  81  Q  G  M  P  T  A  E  D  A  S  V  R  R  R  P  Q  V  T  A  D
 421 GCCGCAACGCCGCGTGCAGAGGCAAGACGCACGCCGGAGGCAACTGCCGATGCCAGCGCA
 101  A  A  T  P  R  A  E  A  R  R  T  P  E  A  T  A  D  A  S  A
 481 CCGCGTAGAGGGGCGGTTGCACACGCCAACAGTATCGTTCAGCAATTGGTCAGTGAGGGC
 121  P  R  R  G  A  V  A  H  A  N  S  I  V  Q  Q  L  V  S  E  G
 541 GCTGATATTTCGCATACTCGTAACATGCTCCGCAATGCAATGAATGGCGACGCAGTCGCT
 141  A  D  I  S  H  T  R  N  M  L  R  N  A  M  N  G  D  A  V  A
 601 TTTTCTCGAGTAGAACAGAACATATTTCGCCAGCATTTCCCGAACATGCCCATGCATGGA
 161  F  S  R  V  E  Q  N  I  F  R  Q  H  F  P  N  M  P  M  H  G
 661 ATCAGCCGAGATTCGGAACTCGCTATCGAGCTCCGTGGGGCGCTTCGTCGAGCGGTTCAC
 181  I  S  R  D  S  E  L  A  I  E  L  R  G  A  L  R  R  A  V  H
 721 CAACAGGCGGCGTCAGCGCCAGTGAGGTCGCCCACGCCAACACCGGCCAGCCCTGCGGCA
 201  Q  Q  A  A  S  A  P  V  R  S  P  T  P  T  P  A  S  P  A  A
 781 TCATCATCGGGCAGCAGTCAGCGTTCTTTATTTGGACGGTTTGCCCGTTTGATGGCGCCA
 221  S  S  S  G  S  S  Q  R  S  L  F  G  R  F  A  R  L  M  A  P
 841 AACCAGGGACGGTCGTCGAACACTGCCGCCTCTCAGACGCCGGTCGACAGGAGCCCGCCA
 241  N  Q  G  R  S  S  N  T  A  A  S  Q  T  P  V  D  R  S  P  P
 901 CGCGTCAACCAAAGACCCATACGCGTCGACAGGGCTGCGATGCGTAATCGTGGCAATGAC
 261  R  V  N  Q  R  P  I  R  V  D  R  A  A  M  R  N  R  G  N  D
 961 GAGGCGGACGCCGCGGCTGCGGGGGTTAGTACAACAGGGGGTCAATTTAGAGCCCTGCGC
 281  E  A  D  A  A  L  R  G  L  V  Q  Q  G  V  N  L  E  H  L  R
1021 ACGGCCCTTGAAAGACATGTAATGCAGCGCCTCCCTATCCCCCTCGATATAGGCAGCGCG
 301  T  A  L  E  R  H  V  M  Q  R  L  P  I  P  L  D  I  G  S  A
1081 TTGCAGAATGTGGGAATTAACCCAAGTATCGACTTGGGGGAAAGCCTTGTGCAACATCCC
 321  L  Q  N  V  G  I  N  P  S  I  D  L  G  E  S  L  V  Q  H  P
1141 CTGCTGAATTTGAATGTAGCGTTGAATCGCATGCTGGGCTGCGTCCCAGCGCTGAAAGA
 341  L  L  N  L  N  V  A  L  N  R  M  L  G  L  R  P  S  A  E  R
1201 GCGCCTCGTCCAGCCGTCCCCGTGGCTCCCGCGACCGCCTCCAGGCGACCGGATGGTACG
 361  A  P  R  P  A  V  P  V  A  P  A  T  A  S  R  R  P  D  G  T
1261 CGTGCAACACGATTGCGGGTGATGCCGGAGCGGGAGGATTACGAAAATAATGTGGCTTAT
 381  R  A  T  R  L  R  V  M  P  E  R  E  D  Y  E  N  N  V  A  Y
1321 GGAGTGCGCTTGCTTAACCTGAACCCGGGGGTGGGGGTAAGGCAGGCTGTTGCGGCCTTT
 401  G  V  R  L  L  N  L  N  P  G  V  G  V  R  Q  A  V  A  A  F
1381 GTAACCGACCGGGCTGAGCGGCCAGCAGTGGTGGCTAATATCCGGGCAGCCCTGGACCCT
 421  V  T  D  R  A  E  R  P  A  V  V  A  N  I  R  A  A  L  D  P
1441 ATCGCGTCACAATTCAGTCAGCTGCGCACAATTTCGAAGGCCGATGCTGAATCTGAAGAG
 441  I  A  S  Q  F  S  Q  L  R  T  I  S  K  A  D  A  E  S  E  E
1501 CTGGGTTTTAAGGATGCGGCAGATCATCACACGGATGACGTGACGCACTGTCTTTTTGGC
 461  L  G  F  K  D  A  A  D  H  H  T  D  D  V  T  H  C  L  F  G
1561 GGAGAATTGTCGCTGAGTAATCCGGATCAGCAGGTGATCGGTTTGGCGGGTAATCCGACG
 481  G  E  L  S  L  S  N  P  D  Q  Q  V  I  G  L  A  G  N  P  T
1621 GACACGTCGCAGCCTTACAGCCAAGAGGGAAATAAGGACCTGGCGTTCATGGATATGAAA
 501  D  T  S  Q  P  Y  S  Q  E  G  N  K  D  L  A  F  M  D  M  K
1681 AAACTTGCCCAATTCCTCGCAGGCAAGCCTGAGCATCCGATGACCAGAGAAACGCTTAAC
 521  K  L  A  Q  F  L  A  G  K  P  E  H  P  M  T  R  E  T  L  N
1741 GCCGAAAATATCGCCAAGTATGCTTTTAGAATAGTCCCCtgaCCGCGCTGACAGCTAAAA
 541  A  E  N  I  A  K  Y  A  F  R  I  V  P  *
1801 GCCCATCAAGCTAGCGCCGACAGCGCTCACTGCCACTTCGAAGGTCGGCGTGGAAAGCTC
1861 CCGAGTCACGGACTTCGCACCTGCGTCAGGGCTCAGTCCATGCGCTCGGGGTAGGTCATC
```

*FIG. 9B*

- 52% identity of amino acid between AvrPtoB and VirPphA
- Black boxed letters: Putative hrp-box

- Red boxed letters: Computer suggested N-myristoylation site
1.   3- 8     GINRAG
2.  25- 30    GQAHGS
3.  29- 34    GSGSGA
4.  31- 36    GSGASS
5.  33- 38    GASSSN
6.  82- 87    GMPTAE
7. 140-145    GADISH
8. 278-283    GNDEAD
9. 288-293    GVSTTG
10. 294-299   GQFRAL
11. 325-330   GINPSI
12. 353-358   GLRPSA
13. 379-384   GTRATR
14. 412-417   GVRQAV
15. 480-485   GGELSL

- Black bold letters: Amino acid identical with amino acid of VirPphA

- Blue arrow: Fusion point of truncated AvrPtoB with LexA of prey vector
1. 70 AA; HinP1I
2. 112 AA; MspI
3. 121 AA; AciI

*FIG. 9B (CONT.)*

ALIGNMENT OF THE AMINO ACID SEQUENCES OF AvrPtoB AND VirPpha

```
BlastX results
                                                          Score      E
Sequences producing significant alignments:              (bits)    Value gi|5702216|gb|AAD47203.1|AF141883_1   (AF141883) VirPphA [Pse...    500    e-140
gi|5702219|gb|AAD47206.1|AF141883_4   (AF141883) unknown [Pse...     70    6e-11
gi|7512219|pir||T18535   high molecular mass nuclear antigen ...     50    6e-05
gi|15236788|ref|NP_194968.1|   (NC_003075) putative protein [...     45    0.002
gi|5420387|emb|CAB46679.1|   (AJ243459) proteophosphoglycan [...     45    0.003
gi|6322209|ref|NP_012284.1|   (NC_001141) Required for invasi...     44    0.005
gi|14251109|ref|NP_116471.1|   (NC_002794) t120 [Tupaia herpe...     43    0.008
gi|4507349|ref|NP_003176.1|   (NM_003185) TATA box binding pr...     42    0.013
gi|17546705|ref|NP_520107.1|   (NC_003295) PROBABLE TRANSMEMB...     42    0.013
gi|15805485|ref|NP_294181.1|   (NC_001263) hypothetical prote...     42    0.013
gi|17487943|ref|XP_036528.2|   (XM_036528) serine/arginine re...     42    0.018

>gi|5702216|gb|AAD47203.1|AF141883_1 (AF141883) VirPphA [Pseudomonas syringae pv.
phaseolicola]  Length = 539

Score =  500 bits (1287), Expect = e-140
 Identities = 303/581 (52%), Positives = 368/581 (63%), Gaps = 28/581 (4%)
 Frame = +1

Query:  1    MAGINRAGPSGAYFVGHTDPEPVSGQAHGSGSGASSSNSPQVQPRPENTPPSNAPAPPPT  180
             M GIN AGPS   ++    TD EPV+ + H S   ASS+NSP++  P  S          P  +
Sbjct:  1    MPGINGAGPSNFFWQMRTDGEPVTEREHDSSRSASSANSPELPPPAS---------PAES  51

Query:  181  GRERLSRSTALSRQTREWLEQGMPTAEDASVRRRPQVTADAATPRAEARRTPEATADASA  360
             GR+RL RS+ALSRQTREWLE      A  A V+           ATP AEAR++PEA
Sbjct:  52   GRQRLLRSSALSRQTREWLE-----ATPARVQ--------GATPPAEARQSPEAQ-----  93

Query:  361  PRRGAVAHANSIVQQLVSEGADISHTRNMLRNAMNGDAVAPSRVBQNIFRQHFPNMPMHG  540
                     A  IVQ+LV  GAD+++  R MLRN M+  +AVAPSRVE++ +I  QHFPNMPM G
Sbjct:  94   -------QAERIVQELVRGGADLNNVRTMLRNVMENNAVAPSRVERDILLQHFPNMPMTG  146

Query:  541  ISRDSELAIELRGALRRAVHQQAASAPVRSPTPTPASPAASSSGSSQRSLFGRFARLMAP  720
             IS DS LA ELR   LR+ V QQ      R + TPA A SSSGSSQRSL GR    LM P
Sbjct:  147  ISSDSVLANELRQRLRQTVRQQ------RIQSSTPARLADSSSGSSQRSLIGRSTMLMTP  200

Query:  721  NQGRSENTAASQTPVDRSPPRVNQRPIRVDRAAMRNRGNDEADAALRGLVQQGVNLEHLR  900
              +  SS+  AAS+T VDR P  ++  R+ AA N    ++ + ALR L Q+GV++E LR
Sbjct:  201  GRSSSSSAAASRTSVDRHPQGLDLESARLASAARHNHSANQTNEALRRLTQEGVDMERLR  260

Query:  901  TALERHVMQRLPIPLDIGSALQNVGINPSIDLGESLVQHPLLNLNVALNRQMGLRPSAER  1080
             T+L R++M   P+P D+    AL+++VGINP I     SLV HP+LN +  ALNRQML  R +
Sbjct:  261  TSLGRYIMSLEPLPPDLRRALESVGINPFIPEELSLVDHPVLNFSAALNRMLASRQTTTN  320

Query:  1081 APRPAVPVAPATASRR------------------------PDGT---RATRLRVMPERE  1176
             +P      + A + RR                          P  +  RA RL VMP +
Sbjct:  321  SPELPPLASSAESGRRRLLRSPPLLSGQREWIEQSMRQEAEPQSSRLNRAVRLAVMPPQN  380

Query:  1177 DYENNVAYGVRLLNLNPGVGVRQAVAAFVTDRAERPAVVANIRAALDPIASQFSQLRTIS  1356
             + E+NVAY +RL LNPG V + VA+F+TD A R  VV +IRAALD IA QFSQLRTIS
Sbjct:  381  ENEDNVAYAIRLRRLNPGADVSRVVASPITDPAARQQVVNDIRAALD-IAPQFSQLRTIS  439

Query:  1357 KADAESEELGPKDAADHHTDDVTHCLFGGELSLSNPDQQVIGLAGNPTDTSQPYSQBGNK  1536
             KADAESEELGP+DAAD H D+ T CLFG ELSLSNPDQQVIGLA NPTD  QPYSQE NK
Sbjct:  440  KADAESEELGPRDAAD-HPDNATSCLFGEHLSLSNPDQQVIGLAVNPTDKPQPYSQEVNK  498

Query:  1537 DLAFMDNKKLAQFLAGKPEHPMTRETLNAENIAKYAFRIVP  1659
             L FMDNKKLAQ+LA KPEHP+ R+ L+A+NIAKYAF+IVP
Sbjct:  499  ALTFMDNKKLAQYLADKPEHPLNRQRLDAKNIAKYAFKIVP  539
```

FIG. 9C

|  | Subregion |
|---|---|
| MAGINRAGPSGAYFVGHTDPEPVSGQAHGSGSGASSSNSPQVQPRPSNTP | I, II |
| MGNICVGG---------------------SRMAHQVNSPDRVSNNSGDE | |

| | |
|---|---|
| PSNAPAPPPTGRERLSRSTALSRQTREWLEQGMPTAEDASVRRRPQVTAD | III |
| DNVTSSQLLSVRHQLAESAGLPRDQHEFVSSQAP----QSLRNR----- | |

NΔ121↓

AATPRAEARRTPEATADASAPRRGAVAHANSIVQQLVSEGADISHTRNML
------------------------------YNNL---------------

| | |
|---|---|
| RNAMNGDAVAFSRVEQNIFRQHFPNMPMHGISRDSELAIELRGALRRAVH | IV |
| ----------YSHTQRTLDMADMQHRYMTGAS----------------- | |

QQAASAPVRSPTPTPASPAASSSGSSQRSLFGRFARLMAPNQGRSSNTAA
-------------------------------------------------

SQTPVDRSPPRVNQRPIRVDRAAMRNRGNDEADAALRGLVQQGVNLEHLR
-------------------------------------------------

```
                              ATA    A A
TALERHVMQRLPIPLDIGSALQNV GINP SIDLGESLVQHPLLNLNVALNR    V
---------------------   GINP ------GMLPHENVD---------
                         ●           ●
```

| | |
|---|---|
| MLGLRPSAERAPRPAVPVAPATASRRPDGTRATRLRVMPEREDYENNVAY | VI |
| --DMR-SAITDW------------------------------------- | |

| | |
|---|---|
| GVRLLNLNPGVGVRQAVAAFVTDRAERPAVVANIRAALDPIASQFSQLRT | VII |
| --------------------------SDMREAL--------------- | |

| | |
|---|---|
| ISKADAESEELGFKDAADHHTDDVTHCLFGGELSLSNPDQQVIGLAGNPT | VIII |
| -------------------------------------QHAMGIHADIP | |

↑ CΔ40

| | |
|---|---|
| DTSQPYSQEGNKDLAFMDMKKLAQFLAGKPEHPMTRETLNAE ... | IX |
| PSPERFVATMN-----------------PSGSIRMSTLSPS ... | |

*FIG. 13A*

| Consensus: | | SxRxxLxxSxxLxRxxxE | |
|---|---|---|---|
| AvrPto | 38 | SVRHQLAESAGLPRDQHE | 55 |
| AvrPtoB | 60 | TGRERLSRSTALSRQTRE | 77 |
| VirPphA | 51 | SGRQRLLRSSALSRQTRE | 68 |
| AvrRpt2 | 49 | ETRALLATKTVLGRHKIE | 66 |
| AvrRps4 | 38 | TTTSIAQASEGLQRPGAT | 55 |
| AvrXa10 | 61 | SPAFSAGSFGDLLRQFDP | 78 |
| AvrPpiB | 41 | IEEHVADRLSDLGRPDGG | 58 |
| AvrPphF | 33 | VGQYTLTSIHQLSSEERE | 50 |
| AvrBs1 | 49 | RKRVIKENIAALHTSSLE | 69 |
| AvrB | 33 | SQRQLEVYDQCLIGAARW | 50 |
| AvrBsT | 42 | SPSQTSSAFSGLPERPRK | 59 |

*FIG. 13B*

BACTERIAL EFFECTOR PROTEINS WHICH INHIBIT PROGRAMMED CELL DEATH

The present invention claims benefit of U.S. Provisional Application Ser. No. 60/404,339, filed Aug. 16, 2002, and U.S. Provisional Application Ser. No. 60/425,842, filed Nov. 12, 2002, which are hereby incorporated by reference in their entirety.

The subject matter of this application was made with support from the United States Government under the United States Department of Agriculture NRI Grant No. 99-35301-7973 and the National Science Foundation Grant No. DBI-0077622. The Government may have certain rights.

FIELD OF THE INVENTION

The present invention relates to a bacterial effector protein which inhibits programmed cell death ("PCD") in eukaryotes.

BACKGROUND OF THE INVENTION

*Pseudomnonas syringae* pv. tomato DC3000 is a widely studied model plant pathogen that causes disease on tomato and *Arabidopsis*. DC3000 uses a type III secretion (TTSS) system to directly deliver bacterial effector proteins into the host cell (Galan et al., "Type III secretion machines: Bacterial devices for protein delivery into host cells." *Science*, 284: 1322-1328 (1999)). Loss of function mutations in the TTSS completely abrogate *P. syringae* disease formation, indicating that effectors are essential agents of *P. syringae* pathogenesis (Collmer et al., "*Pseudomonas syringae* Hrp type III secretion system and effector proteins." *Proc Natl Acad Sci USA*, 97: 8770-8777 (2000)). In bacterial pathogens of plants, the TISS is encoded by the hypersensitive response ("HR") and pathogenicity (hrp) genes (Lindgren, P. B., "The role of hrp genes during plant-bacterial interactions." *Annu. Rev. Phytopathol.* 35: 129-152 (1997)). Mutations in key hip genes prevent the secretion of effectors and inhibit pathogen growth and host defenses. A hallmark of effector genes is the presence of a "Hrp box" cis element in their promoter which is recognized by the HrpL ECF-like sigma factor (Innes et al., "Molecular analysis of avirulence gene avrRpt2 and identification of a putative regulatory sequence common to all known *Pseudomonas syringae* avirulence genes." *J. Bacteriol.* 175: 4859-4869 (1993); Xiao et al., "Identification of a putative alternate sigma factor and characterization of a multicomponent regulatory cascade controlling the expression of *Pseudomonase syringae* pv. *syringae* Pss61 hrp and hrmA genes." *J. Bacteriol.* 176: 1025-1036 (1994)). A recent search for Hrp box containing genes in the genome of *Pseudomonas syringae* pv. tomato strain DC3000 revealed over 20 putative effector genes (Fouts, et al., "Genomewide identification of *Pseudomonas syringae* pv. tomato DC3000 promoters controlled by the HrpL alternative sigma factor." *Proc Natl Acad Sci USA*, 99: 2275-2280 (2002)). Although the role of effector proteins in pathogen virulence is poorly understood, many effectors have been isolated based on their ability to trigger host immunity.

In the "gene-for-gene" model of plant immunity, disease resistance is initiated by recognition of a pathogen avirulence (Avr) effector protein by a plant resistance (R) protein. The tomato R protein Pto, a serine/threonine protein kinase, recognizes and directly interacts with DC3000 effector proteins AvrPto and AvrPtoB, and initiates immunity in tomato by characterized and uncharacterized signaling mechanisms (Kim et al., "Two distinct *pseudomonas* effector proteins interact with the pto kinase and activate plant immunity." *Cell*, 109: 589-598 (2002); Scofield et al., "Molecular basis of gene-for-gene specificity in bacterial speck disease of tomato." *Science*, 274: 2063-2065 (1996); Sessa et al., "Signal recognition and transduction mediated by the tomato Pto kinase: a paradigm of innate immunity in plants." *Microbes Infect*, 2: 1591-1597 (2000); Tang et al., "Overexpression of Pto activates defense responses and confers broad resistance." *Plant Cell*, 11: 15-30 (1999)). Interestingly, the Pto kinase shares sequence similarity with the human interleukin-1 receptor associated kinase (IRAK) and with the *Drosophlila* Pelle kinase, both of which, like Pto, play a role in immune responses (Cohn et al., "Innate immunity in plants." *Curr. Opin. Immunol.*, 13: 55-62 (2001); Hoffman et al., "Phylogenetic perspectives in innate immunity," *Science* 284:1313-1318 (1999)). The Pto gene belongs to a gene family of 6 members on tomato chromosome 5 (Martin et al., "Map-based cloning of a protein kinase gene conferring disease resistance in tomato." *Science*, 262: 1432-1436 (1993); Michelmore et al., "Clusters of resistance genes in plants evolve by divergent selection and a birth-and-death process." *Genome Res.* 8: 1113-1130 (1998); Riely et al., "Ancient origin of pathogen recognition specificity conferred by the tomato disease resistance gene Pto." *Proc. Natl. Acad. Sci. USA* 98: 2059-2064 (2001)). One of these family members, Fen, encodes a kinase that confers sensitivity to an insecticide (fenthion), while the function of the others is unknown (Martin et al., "A Member of Tomato Pto Gene Family Confers Sensitivity to Fenthion Resulting in Tomato," *Plant Cell* 6:1543-1552 (1994)).

The R gene-mediated plant immune response is characterized by a series of physiological changes in the plant cell, including the formation of reactive oxygen species, induction of defense genes, and the HR. The HR is defined as a defense response involving rapid, localized cell death that functions to limit pathogen growth (Goodman et al., "The hypersensitive reaction in plants to pathogens." APS Press, St. Paul, Minn., USA, (1994)). The cell death associated with the HR is a genetically controlled and regulated process and an example of programmed cell death in plants (Greenberg, J. T. "Programmed cell death in plant-pathogen interactions." *Annu. Rev. Plant Physiol. Plant Mol. Biol.*, 48: 525-545 (1997); Heath, M. C. "Hypersensitive response-related death." *Plant Mol Biol*, 44: 321-334 (2000)). As such, programmed cell death is a hallmark of HR-based immunity in plants, and cell death phenotypes are often used in laboratory experiments to discover and dissect plant immune responses.

The AvrPtoB protein has a predicted molecular mass of 59 kDa, is secreted via the TTSS, and triggers the HR and immunity in Pto-expressing tomato plants. AvrPtoB has limited similarity to AvrPto; however, it shares 52% amino acid identity with the P. s. pv. *phaseolicola* effector VirPphA (Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*, 96: 10875-10880 (1999)). In general, bacterial effector proteins are highly diverse with little amino acid sequence similarity among them (one exception is the AvrBs3 family; Lindgren, P. B., "The role of hrp genes during plant-bacterial interactions." *Annu. Rev. Phytopathol.* 35: 129-152 (1997); White et al., "Prospects for understanding avirulence gene function." *Curr. Opin. Plant Biol.* 3: 291-298 (2000)). They have been identified from all four of the most common genera of plant bacterial pathogens (i.e., *Pseudomonas, Xanthomonzas, Erwinia,* and *Ralstonia*). In a still cryptic process, these pathogens utilize the TTSS to inject effectors across the plant cell wall into the cytoplasm (Galan et al., "Type III secretion machines: Bacterial devices for protein delivery into host cells." *Science*, 284: 1322-1328 (1999); Jin et al., "Role of the Hrp pilus in type III protein secretion in *Pseudomonas syringae*." *Science* 294: 2556-2558 (2001)). Little is known of the fate of bacterial effectors once they are in the plant cell although some members of the AvrBs3 family are localized to the nucleus, some effector proteins are targeted to the plasma membrane after being myristylated, and others are processed to smaller forms (Nimchuk et al., "Eukaryotic fatty acylation drives plasma membrane targeting and enhances function of several type III effector proteins from *Pseudomonas syringae*." *Cell.* 101: 353-363 (2000); Shan et al., "The *Pseudomonas* AvrPto protein is differentially recognized by tomato and tobacco and is localized to the plant plasma membrane." *Plant Cell* 12: 2323-2337 (2000b); Van der Ackerveken et al., "Recognition of the bacterial avirulence protein AvrBs3 occurs inside the host cell." *Cell* 87: 1307-1316 (1996); Zhu et al., "The C terminus of AvrXa10 can be replaced by the transcriptional activation domain of VP16 from the herpes simplex virus." *Plant Cell.* 11: 1665-1674 (1999)).

The AvrPto protein and the Pto kinase physically interact in a yeast two-hybrid system (Scofield et al., "Molecular basis of gene-for-gene specificity in bacterial speck disease of tomato." *Science* 274: 2063-2065 (1996); Tang et al., "The avirulence protein AvrPto physically interacts with the Pto kinase." *Science* 274: 2060-2063 (1996)). Co-expression of Pto and AvrPto as transgenes in a pto mutant leaf is sufficient to activate resistance. Mutations that disrupt this interaction also abolish the ability to elicit disease resistance in plant leaves (Chang et al., "Functional studies of the bacterial avirulence protein AvrPto by mutational analysis." *Mol. Plant-Microbe Interact.* 14: 451-459 (2001); Frederick et al., "Recognition specificity for the bacterial avirulence protein AvrPto is determined by Thr-204 in the activation loop of the tomato Pto kinase." *Molecular Cell.* 2: 241-245 (1998); Shan et al., "The *Pseudomonas* AvrPto protein is differentially recognized by tomato and tobacco and is localized to the plant plasma membrane." *Plant Cell* 12: 2323-2337 (2000)). Resistance is dependent on the Prf protein which bears striking similarity to the large NB-LRR class of R proteins (Salneron et al., "Tomato Prf is a member of the leucine-rich repeat class of plant disease resistance genes and lies embedded within the Pto kinase gene cluster." *Cell* 86: 123-133 (1996)). Pto-Fen chimeras were used to define the kinase activation loop as a key determinant of Pto interaction specificity for AvrPto (Frederick et al., "Recognition specificity for the bacterial avitulence protein AvrPto is determined by Thr-204 in the activation loop of the tomato Pto kinase." *Molecular Cell.* 2: 241-245 (1998); Scofield et al., "Molecular basis of gene-for-gene specificity in bacterial speck disease of tomato." *Science* 274: 2063-2065 (1996); Tang et al., "The avirulence protein AvrPto physically interacts with the Pto kinase." *Science* 214: 2060-2063 (1996)). Pto kinase is phosphorylated on 8 residues and mutation of two of these residues (T38 and S198) abolishes its ability to elicit host resistance (Sessa et al., "Thr38 and Ser198 are Pto autophosphorylation sites required for the AvrPto-Pto-mediated hypersensitive response." *EMBO J.* 19: 2257-2269 (2000)). Recognition specificity of Pto for AvrPto appears to have evolved before *Lycopersicon* speciation because a Pto family member from a distantly related species, *L. hirsutum*, also recognizes AvrPto (Riely et al., "Ancient origin of pathogen recognition specificity conferred by the tomato disease resistance gene Pto." *Proc. Natl. Acad. Sci. USA* 98: 2059-2064 (2001)).

The AvrPto gene was originally isolated from *P. s. tomato* strain JL1065 based on its ability to confer avirulence to a virulent strain of *P. s. inaculicola* (Ronald et al., "The cloned avirulence gene avrPto induces disease resistance in tomato cultivars containing the Pto resistance gene." 174: 1604-1611 (1992)). AvrPto encodes an 18 kD protein that bears little sequence similarity to proteins in current databases (Salmeron et al., "Molecular characterization and hrp dependence of the avirulence gene avrPto from *Pseudomoizas syringae* pv. tomato." *Mol. Gen. Genet.* 239: 6-16 (1993)). Its mechanism of activating resistance is unknown although it likely interacts with Pto inside the plant cell and possibly with certain 'AvrPto-dependent Pto-interacting' (Adi) proteins as part of a complex (Bogdanove et al., "AvrPto-dependent Pto-interacting proteins and AvrPto-interacting proteins in tomato." *Proc. Natl. Acad. Sci. USA* 97: 8836-8840 (2000); Scofield et al., "Molecular basis of gene-for-gene specificity in bacterial speck disease of tomato." *Science* 274: 2063-2065 (1996); Tang et al., "The avirulence protein AvrPto physically interacts with the Pto kinase." *Science* 274: 2060-2063 (1996)). AvrPto acts as a virulence factor when Pto (or Prf) is absent from the plant cell and increases the growth of *P. s. tomato* about 10-fold as compared to a strain lacking the effector (Chang et al., "avrPto enhances growth and necrosis caused by *Pseudomonas syringae* pv. tomato in tomato lines lacking either Pto and Prf." *Mol. Plant-Microbe Interact.* 13: 568-571 (2000); Shan et al., "A cluster of mutations disrupt the avirulence but not the virulence function of AvrPto." *Mol. Plant-Microbe Interact.* 13: 592-598 (2000)). In common with several effectors, AvrPto has a myristylation motif at its N terminus that is required for both its avirulence and virulence activity (Nimchuk et al., "Eukaryotic fatty acylation drives plasma membrane targeting and enhances function of several type III effector proteins from *Pseudomonas syringae*." *Cell.* 101: 353-363 (2000); Shan et al., "The *Pseudomonas* AvrPto protein is differentially recognized by tomato and tobacco and is localized to the plant plasma membrane." *Plant Cell* 12: 2323-2337 (2000)). The amino acids of AvrPto that are required for its recognition by the Pto kinase have been examined by saturation mutagenesis (Chang et al., "Functional studies of the bacterial avirulence protein AvrPto by mutational analysis." *Mol. Plant-Microbe Interact.* 14: 451-459 (2001); Shan et al., "A cluster of mutations disrupt the avirulence but not the virulence function of AvrPto." *Mol. Plant-Microbe Interact.* 13: 592-598 (2000); Shan et al., "The *Pseudomonas* AvrPto protein is differentially recognized by tomato and tobacco and is localized to the plant plasma membrane." *Plant Cell* 12: 2323-2337 (2000)). Mutation of three AvrPto residues—S94, 196, and G99—abolishes interaction with Pto and avirulence activity, but not virulence activity, in tomato (Shan et al., "A cluster of mutations disrupt the avirulence but not the virulence function of AvrPto." *Mol. Plant-Microbe Interact.* 13: 592-598 (2000); Shan et al., "The *Pseudomonas* AvrPto protein is differentially recognized by tomato and tobacco and is localized to the plant plasma membrane." *Plant Cell* 12: 2323-2337 (2000)). Along with the other observations (Chang et al., "Functional studies of the bacterial avirulence protein AvrPto by mutational analysis." *Mol. Plant-Microbe Interact.* 14: 451-459 (2001)), these results indicate that an internal region of AvrPto determines its binding specificity for Pto.

AvrPto-like DNA sequences are present in *Pseudomonas* strains that are known to be avirulent on Pto tomato plants (race 0 strains) and are absent from virulent ones (race 1 strains; Ronald et al., "The cloned avirulence gene avrPto induces disease resistance in tomato cultivars containing the Pto resistance gene." 174: 1604-1611 (1992)). Thus, a homolog of avrPto was identified in avirulent *P. s. tomato* strain DC3000 based on DNA blot hybridization (Ronald et al., "The cloned avirulence gene avrPto induces disease resistance in tomato cultivars containing the Pto resistance gene." 174: 1604-1611 (1992)). Gene replacement strains in which the avrPto reading frame was deleted were constructed in strains JL1065 and DC3000. Surprisingly, both mutant strains were still recognized by Pto-expressing tomato leaves (Ronald et al., "The cloned avirulence gene avrPto induces disease resistance in tomato cultivars containing the Pto resistance gene." 174: 1604-1611 (1992)). A later study found that a tomato line carrying a CaMV 35S::Pto transgene (and not a sibling line without Pto) is resistant to the avrPtoΔDC3000 deletion strain. These results implied that strains DC3000 and JL1065 carry additional avirulence proteins that are recognized specifically by Pto.

In recent years, evidence has accumulated that effector proteins can interfere with host defense responses. In a breakthrough study, Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*, 96: 10875-10880 (1999) demonstrated that VirPphA allows P. s. pv. *phaseolicola* to evade HR-based immunity in bean. Other P. s. pv. *phaseolicola* effectors also allow the pathogen to avoid triggering host immunity, including AvrPphC and AvrPphF (Tsiamis et al., "Cultivar-specific avirulence and virulence functions assigned to avrPphF in *Pseudomonas syringae* pv. *phaseolicola*, the cause of bean halo-blight disease." *Embo J*, 19: 3204-3214 (2000)). Additionally, in the P. s. pv. *maculicola-Arabidopsis* pathosystem, interference has been observed with the effector proteins AvrRpt2 and AvrRpm1 and the HR initiated by the R proteins RPS2 and RPM1, respectively (Reuber et al, "Isolation of arabidopsis genes that differentiate between resistance responses mediated by the RPS2 and RPM1 disease resistance genes." *Plant Cell*, 8: 241-249 (1996); Ritter et al., "Interference between two specific pathogen recognition events mediated by distinct plant disease resistance genes." *Plant Cell*, 8: 251-257 (1996)). These findings suggest that for some effector proteins virulence activity can be dominant over avirulence activity. Although the phenomenon of effector-mediated evasion of plant immunity has been well documented, the molecular basis of this activity has remained mysterious. Several hypotheses have been proposed to explain how some effector proteins (such as VirPphA, AvrPphC and AvrPphF) prevent a host from detecting a pathogen, including: i) inhibition of avr gene expression; ii) blocking of Avr protein secretion or translocation; iii) interference with Avr/R protein recognition inside the plant cell; or iv) suppression of HR or disease resistance signaling downstream of Avr recognition (Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*, 96: 10875-10880 (1999); Tsiamis et al., "Cultivar-specific avirulence and virulence functions assigned to avrPphF in *Pseudomonas syringae* pv. *phaseolicola*, the cause of bean halo-blight disease." *Embo J*, 19: 3204-3214 (2000)). Specific support, however, for any one of these hypotheses has not been reported.

The present invention is directed to overcoming these and other deficiencies in the art.

SUMMARY OF THE INVENTION

The present invention relates to a bacterial effector protein which inhibits programmed cell death in eukaryotes.

The present invention also relates to a nucleic acid molecule encoding a bacterial effector protein which inhibits programmed cell death in eukaryotes.

Another aspect of the present invention pertains to host cells, transgenic plants, and transgenic plant seeds containing a nucleic acid molecule encoding a bacterial effector protein which inhibits programmed cell death in eukaryotes.

The present invention is also directed to a method of suppressing programmed cell death in eukaryotes. This method involves transforming a eukaryote with a nucleic acid encoding a bacterial effector protein which inhibits programmed cell death in eukaryotes. The eukaryote is then grown under conditions effective to suppress programmed cell death in the eukaryote.

A further aspect of the present invention relates to a method of delaying senescence in plants. This method involves transforming a plant with a nucleic acid encoding a bacterial effector protein which inhibits programmed cell death in eukaryotes. The plant is then grown under conditions effective to delay senescence in the plant.

Yet another aspect of the present invention relates to a method of increasing protein expression in plants. This method involves transforming a plant with a nucleic acid encoding a first bacterial effector protein which inhibits programmed cell death in eukaryotes and a second protein which is toxic to plants. The plant is grown under conditions effective to increase expression of the second protein in the plant.

Another aspect of the present invention pertains to expression vectors, transgenic plants, and transgenic plant seeds containing a nucleic acid construct having a nucleic acid molecule encoding a first bacterial effector protein of the present invention coupled to a nucleic acid molecule producing a second protein toxic to eukaryotes.

Yet another aspect of the present invention relates to a method of stabilizing a transgenic plant producing a protein toxic to plants. This method involves providing a transgenic plant transduced with a nucleic acid molecule encoding a first bacterial effector protein which inhibits programmed cell death in eukaryotes and a nucleic acid molecule producing a protein toxic to plants. The plant is then grown under conditions effective to stabilize the plant.

A further aspect of the present invention relates to a method of treating a subject for conditions mediated by programmed cell death. This method involves administering to the subject a bacterial effector protein which inhibits programmed cell death under conditions effective to treat the condition mediated by programmed cell death.

The bacterial effector proteins of the present invention can be used to inhibit programmed cell death in eukaryotes. In particular, AvrPtoB will be a useful tool to dissect the molecular basis of plant R protein programmed cell death signaling, which presently is poorly understood. AvrPtoB anti-PCD activity may also have biotechnical applications. For example, AvrPtoB may allow efficient transgenic expression of proteins that otherwise elicit host PCD or may function to alter PCD-dependent plant developmental processes, such as senescence. Increased understanding of the complex basis of effector-mediated PCD inhibition and host mechanisms that guard against PCD inhibition, should lead to further novel insights into the molecular basis of plant immunity and disease.

BRIEF DESCRIPTION OF THE DRAWINGS

FIG. 1A shows proteins co-expressed in *N. benthamiana* using *Agrobacterium*-mediated transient expression. Leaves were agroinfiltrated within the marked circles and photos were taken 7 days after agroinfiltration. FIG. 1B shows AvrPtoB suppressing PCD initiated by AvrPto/Pto recognition in *N. benthamiana*. The *N. benthamaniana* leaf was agroinfiltrated with AvrPto and Pto and left to dry. On the left hand side, AvrPtoB was agroinfiltrated, and on the right hand side, a vector control was agroinfiltrated. After 7 days, an island of PCD suppressed tissue was observed in AvrPtoB expressing cells. FIG. 1C is an immunoblot analysis of AvrPto:HA, AvrPtoB:HA and Pto:HA co-expression in *N. benthamiana*. Lane 1: AvrPto, AvrPtoB, Pto; 2, AvrPtoB; 3, Pto; 4, AvrPto.

FIG. 2A shows AvrPtoB protecting *S. cerevisiae* strain EGY48 from 3 mM $H_2O_2$-induced PCD. The agar plates show increased survival of yeast cells expressing AvrPtoB as compared to the wild type after treatment with 3 mM $H_2O_2$. FIG. 2B shows AvrPtoB protecting yeast from cell death triggered by: 1) 3 mM $H_2O_2$, 2) 5 mM $H_2O_2$, 3) 5 mM menadione, 4) 10 mM menadione, 5) heat shock at 50° C., and 6) heat shock at 50° C. with a 37° C. pre-treatment. White bars represent wild type yeast and black bars represent AvrPtoB expressing yeast. Error bars show the standard deviation about the mean for three trials.

FIG. 3A is a schematic representation of AvrPtoB truncations examined in this study and yeast two-hybrid analysis of physical interactions between AvrPtoB truncations and the Pto R protein. AvrPtoB truncations were cloned as bait fusions and tested against a Pto prey fusion. Constructs shaded black interacted strongly with Pto. FIG. 3B shows in planta transient expression of AvrPtoB truncations in tomato. RG-PtoR, RG-pto11 and RG-prf3 are isogenic tomato lines with the *L. pimpenillifolium* Pto haplotype and genotypes as indicated. RG-ptoS is a near-isogenic line with the *L. esculentum* Pto haplotype. *Note: a late-onset weak cell death phenotype was observed with Δ6 expression in RG-ptoS. +=cell death, −=no response.

FIGS. 4A-C show recognition and anti-PCD activity of AvrPtoB truncations in *N. benthamiana*. FIG. 4A shows full length and truncated AvrPtoB constructs were transiently expressed: i) with AvrPto+Pto to test for anti-PCD activity, ii) with Pto to test for Pto-mediated PCD, and iii) alone to test for Rsb-mediated PCD. Protein expression of each truncation is established by an observable phenotype. FIG. 4B shows epistasis experiments examining the molecular basis of Δ6/Pto- and Δ7/Pto-initiated PCD and FIG. 4C shows Δ6-initiated PCD. Intact AvrPtoB suppressed PCD initiated by Δ6/Pto, Δ7/Pto, and Δ6, suggesting an intermolecular mechanism of anti-PCD activity. Photos were taken 7 days after agroinfiltration.

FIG. 5A is a schematic representation of avrPtoB chromosomal mutations in P. s. pv. tomato DC3000, generated by insertion of the 6 kb pKnockout plasmid. Amino acid numbers correspond to the amino-acid residue where the expressed mutant protein is interrupted by the insertion. FIG. 5B shows disease responses of tomato plants inoculated with DC3000:mut mutants. Note that only DC3000::mut5 triggers immunity in RG-pto11 plants and this is the only mutant that expresses AvrPtoB with the Rsb triggering domain described in the text. The immunity observed in RG-PtoR plants is likely the result of AvrPto recognition. I=Immunity, D=Disease.

FIG. 6A shows disease symptoms or host immunity on tomato leaves 6 days after inoculation with indicated bacterial strains. Mutant DC3000::mut5 triggers immunity in RG-pto11 and expression of AvrPtoB in trans restores DC3000::mut5 pathogenicity. pDSK519 is a broad host range plasmid. I=Immunity; D=Disease. FIG. 6B shows bacterial growth in leaves over a period of 6 days as measured by the number of colony forming units (cfu) per $cm^2$ of leaf tissue. Errors bars represent the standard deviation of bacterial counts.

Figure 7B:
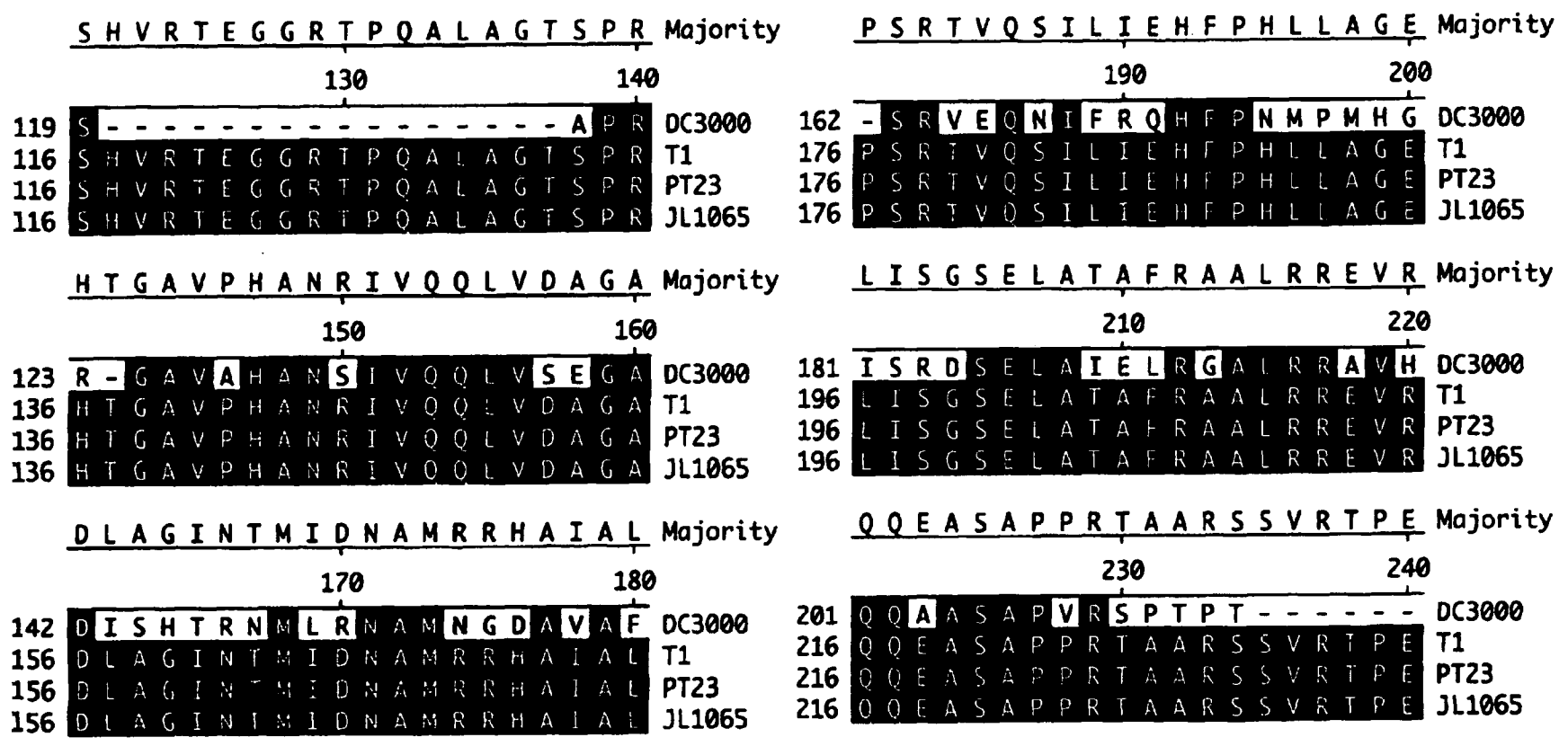
Figure 7D:
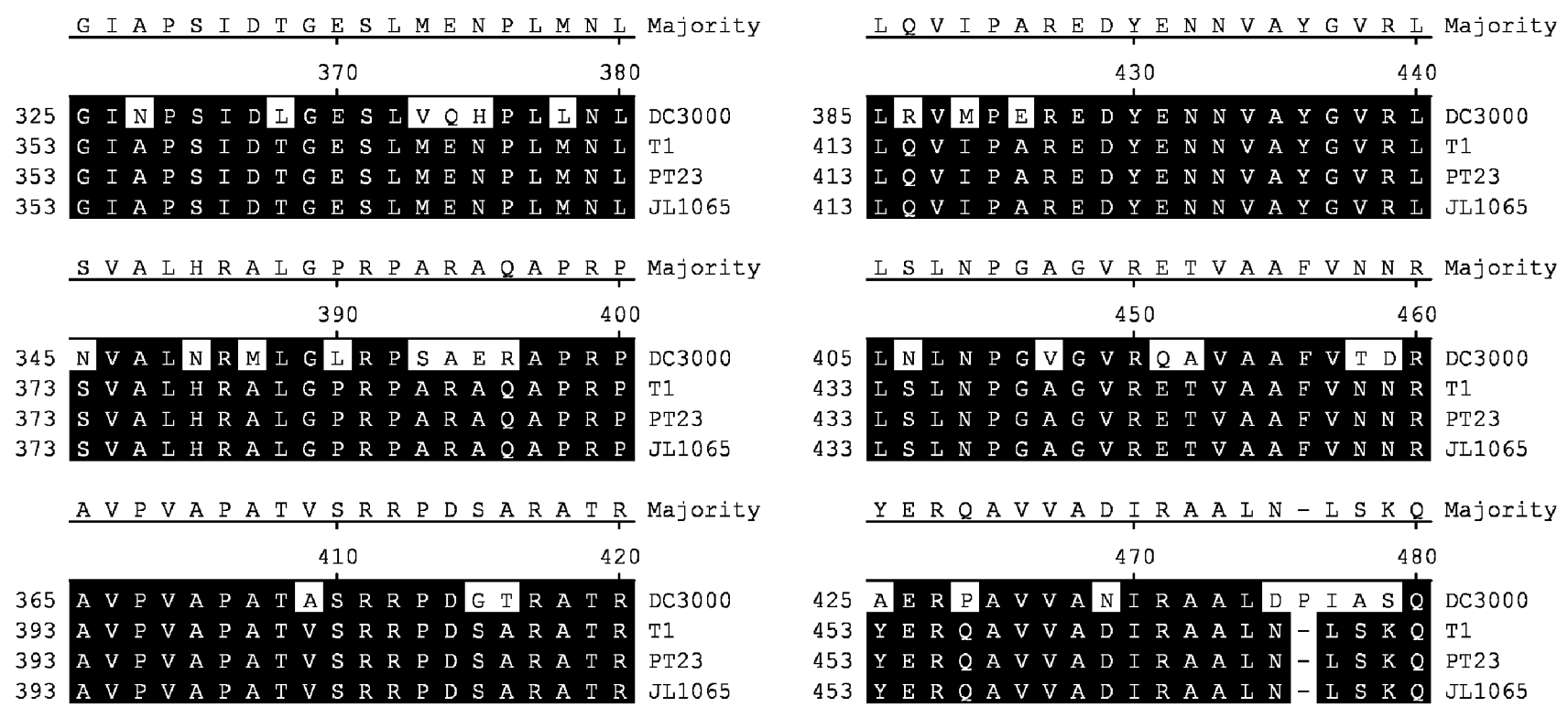
Figure 7E:
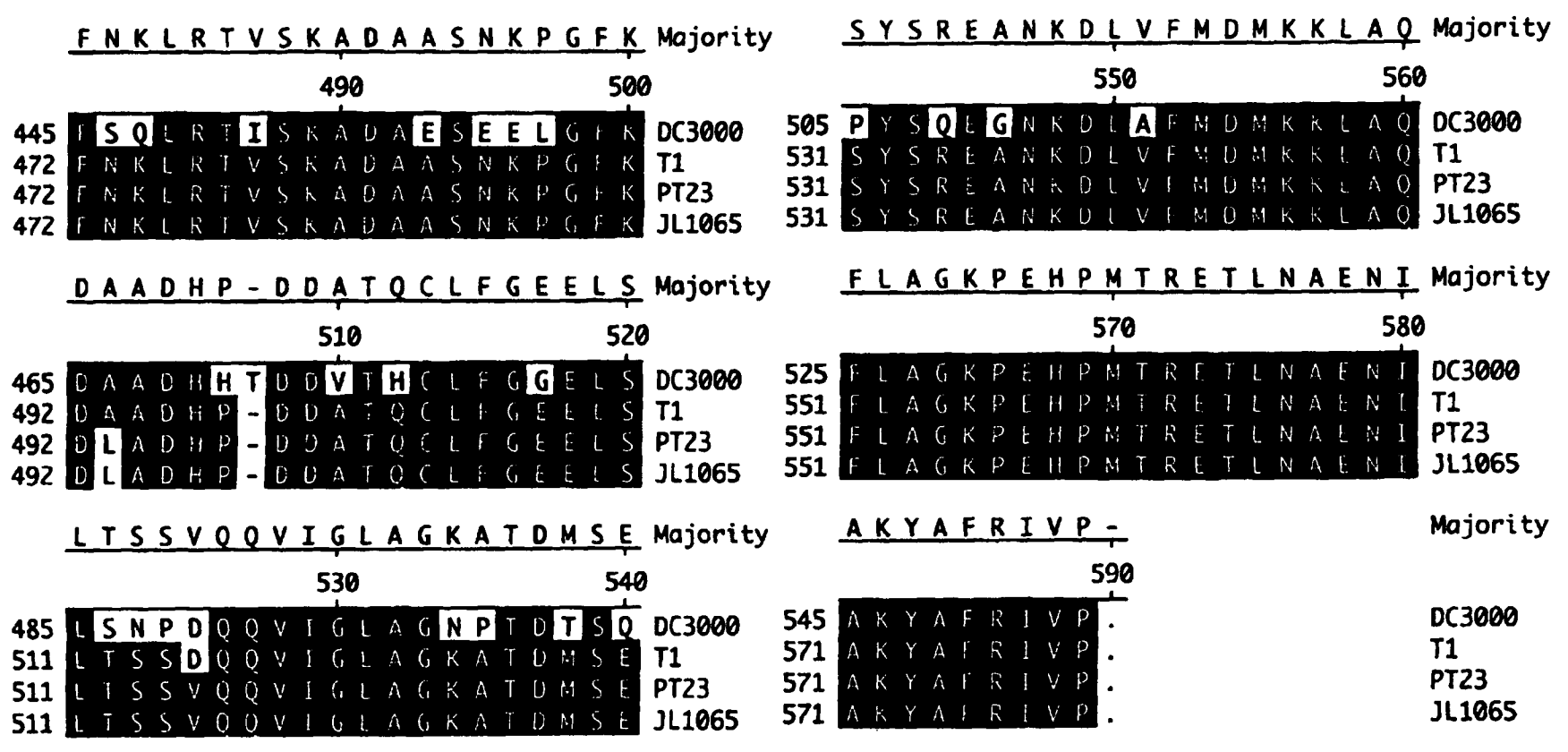

FIGS. 7A-E show AvrPtoB, AvrPtoBT1, AvrPtoBT23, and AvrPtoBJL1065 amino acid sequences aligned by Clustal V method provided by DNAStar software (DNAStar, Inc., Madison, Wis.). Identical amino acids among sequences are shown in black boxes.

FIGS. 9A-C show interaction of *Pseudomonas* effector protein AvrPtoB with the Pto kinase in the yeast two-hybrid system and features of the AvrPtoB gene. FIG. 9A shows a test for specificity of AvrPtoB and AvrPto interaction with Pto family proteins and Pti1 kinase in the LexA yeast two-hybrid system. The avrPtoB (PtiDC1Δ70) and avrPto genes were cloned into the prey vector pJG4-5 and the Pto, Pti1, and Bicoid genes were cloned into the bait vector pEG202. The constructs were transformed into yeast strain EGY48 carrying a lacZ reporter gene and the cells were plated onto medium containing X-gal. Dark blue color indicates interaction. FIG. 9B shows the nucleotide sequence and corresponding encoded amino acid sequence of the avrPtoB gene (GenBank Acc. No. AY074795). The region upstream of the putative start codon shows the Hrp box cis element and the entire open reading frame of avrPtoB. The amino acids of the AvrPtoB protein are given in single letter code. FIG. 9C shows database search results using the avrPtoB gene. The avrPtoB genomic DNA sequence was used to search the National Center for Biotechnology Information sequence database using the BlastX algorithm. VirPphA was the gene in the database with the greatest similarity to avrPtoB with an E value of $e^{-140}$. Amino acid alignments of AvrPtoB (SEQ ID NO:2) and VirPphA (SEQ ID NO: 52) reveal substantial amino acid sequence conservation across both predicted proteins, with 52% amino acid identity and 63% amino acid similarity.

FIG. 10A shows interactions of Pto-Fen chimeric proteins (Tang et al., "The avirulence protein AvrPto physically interacts with the Pto kinase." *Science* 274: 2060-2063 (1996), which is hereby incorporated by reference in its entirety) with AvrPtoB and AvrPto in the LexA yeast two-hybrid system. The diagram depicts Pto (black regions) and Fen (white regions) chimeric proteins. EGY48 yeast cells containing the Pto-Fen chimeric proteins in bait vector pEG202, AvrPtoB or AvrPto in prey vector pJG4-5, and the lacZ reporter gene were grown on medium containing X-gal. Equal expression of each chimeric protein was verified by Western blot (Tang et al., "The avirulence protein AvrPto physically interacts with the Pto kinase." *Science* 274: 2060-2063 (1996), which is hereby incorporated by reference in its entirety). FIG. 10B shows interaction of the internal region of Pto (Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety) with AvrPtoB or AvrPto in the LexA yeast two-hybrid system. Chimeric proteins FPB, FPB2, FPB3 and FPB4 contain the amino acids from Pto (black regions) or from Fen (white regions). Numbers corresponding to amino acid positions in Pto are indicated. Equal expression of Pto-Fen chimeric proteins was verified by Western blot (Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety). FIG. 10C shows the effect of amino acid substitutions in Pto/Fen kinase subdomain VIII on the interaction with AvrPtoB and AvrPto in the yeast two-hybrid system. Portions of proteins, and individual amino acids, derived from Pto (in black) or Fen (in white) are shown. Unboxed amino acids are identical in both kinases. The numbering of amino acids and designation of substitutions correspond to the Pto sequence (Martin et al., "Map-based cloning of a protein kinase gene conferring disease resistance in tomato." *Science,* 262: 1432-1436 (1993), which is hereby incorporated by reference in its entirety).

FIG. 12A shows elicitation of a Pto- and Prf-specific HR in tomato leaves by a *P. fluorescens* strain expressing a type III secretion system and avrPtoB. Tomato leaves of the indicated genotypes were syringe-infiltrated with 1×10$^7$ cfu/mL of *P. fluorescens* (pHIR11; Hrp+) carrying avrPtoB on the wide host range vector pDSK519. The HR appeared within 24 hr only in RG-PtoR leaves (see arrow; some necrosis due to wounding with the syringe is visible on other leaves). Infiltration of 1×10$^7$ cfu/mL of *P. fluorescens* (pHIR11; Hrp+) with pDSK519 alone elicited no response in any leaf genotypes. Photographs were taken 4 days after infiltration. FIG. 12B shows elicitation of a Pto- and Prf-specific HR in tomato leaves upon expression of an avrPtoB transgene directly in plant cells. A suspension of *Agrobacterium* strain GV2260 (OD$_{600}$=0.06) carrying a binary vector with an avrPtoB transgene expressed by the CaMV 35S promoter was infiltrated into leaves of the indicated genotypes. The HR appeared within 18 hr only in RG-PtoR leaves (see arrow). Infiltration of *Agrobacterium* carrying an empty binary vector elicited no response in any leaf genotypes. Photographs were taken 4 days after infiltration. FIG. 12C shows co-expression of Pto and avrPtoB transgenes directly in pto mutant leaf cells elicits the HR. A mixture of suspensions of *Agrobacterium* strain GV2260 (OD$_{600}$=0.06) carrying a binary vector with an avrPtoB or Pto transgene transcribed by the CaMV 35S promoter was infiltrated into leaves of RG-pto11. The HR appeared within 24 hr only in leaves expressing both Pto and avrPtoB (arrow). Infiltration of *Agrobacterium* carrying an empty binary vector elicited no response in any leaf genotypes. Photographs were taken 4 days after infiltration.

FIGS. 13A-B show that AvrPtoB and AvrPto share discrete regions in common and subregion II is conserved among diverse bacterial effector proteins. FIG. 13A shows how amino acid sequences of AvrPtoB (SEQ ID NO:2)(top) and AvrPto (SEQ ID NO:53)(bottom) were aligned using DNAStar software and visually; dashes indicate gaps introduced to optimize the alignment. Nine subregions which contain identical amino acids are shown in boxes. The glycine residue present in the myristylation motif of AvrPto is underlined. Dots indicate residues of AvrPto in which substitutions cause loss of Pto interaction in yeast two-hybrid system and HR in Pto-expressing tomato leaves (Shan et al., "The *Pseudomonas* AvrPto protein is differentially recognized by tomato and tobacco and is localized to the plant plasma membrane." *Plant Cell* 12: 2323-2337 (2000), which is hereby incorporated by reference in its entirety). The arrow in subregion III indicates the most N-terminal truncated AvrPtoB protein (Δ121) that still interacts with Pto in the two-hybrid system. The arrow in subregion VIII indicates the most C-terminal truncated form of AvrPto (Δ40) that still interacts with Pto in the two-hybrid system (Chang et al., "Functional studies of the bacterial avirulence protein AvrPto by mutational analysis." *Mol. Plant-Microbe Interact.* 14: 451-459 (2001), which is hereby incorporated by reference in its entirety). The 'GINP' motif is boxed (located in subregion V) and the substitutions which were made in this region are shown above AvrPtoB. FIG. 13B shows alignment of part of subregion III in AvrPtoB and AvrPto that shares similar residues with diverse effector proteins from other bacterial phytopathogens. A consensus (SEQ ID NO:54) is also shown at the top. The amino acid position of the region in each effector protein is indicated. Origin of the effectors is: *P. s. tomato* strain (AvrPto, AvrPtoB, AvrRpt2), *P. s. glycinea* (AvrB), *P. s. phaseolicola* (VirPphA, AvrPphF), *P. s. pisi* (AvrRps4, AvrPpiB), *Xanthomonas campestris* pv. *vesicatoria* (AvrBs1, AvrBsT), and *X. oryzae* pv. *oryzae* (AvrXa10).

DETAILED DESCRIPTION OF THE INVENTION

Figure 1A:
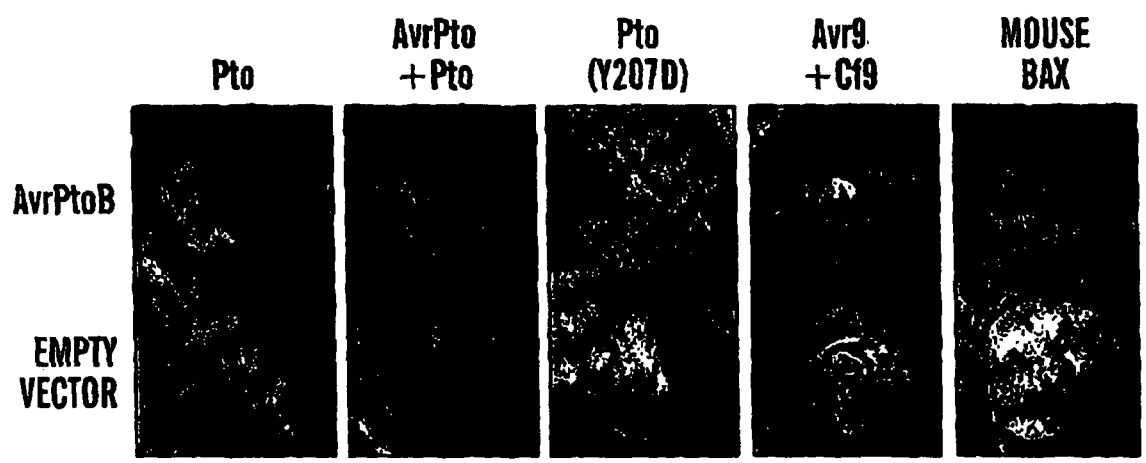
FIGS. 1A-C show AvrPtoB-mediated inhibition of PCD in *N. beizthamiana*.

The present invention relates to a bacterial effector protein which inhibits programmed cell death in eukaryotes.

The present invention also relates to a nucleic acid molecule encoding a bacterial effector protein which inhibits programmed cell death in eukaryotes.

In the first aspect of the present invention, the bacterial effector protein is identified herein as avrPtoB (PstDC3000) and is encoded by a nucleic acid molecule having a nucleotide sequence of SEQ ID NO:1 as follows:

```
atggcgggta tcaatagagc gggaccatcg gcgcttatt ttgttggcca cacagacccc    60
gagccagtat cggggcaagc acacggatcc ggcagcggcg ccagctcctc gaacagtccg   120
caggttcagc cgcgaccctc gaatactccc ccgtcgaacg cgcccgcacc gccgccaacc   180
ggacgtgaga ggctttcacg atccacggcg ctgtcgcgcc aaaccaggga gtggctggag   240
cagggtatgc ctacagcgga ggatgccagc gtgcgtcgta ggccacaggt gactgccgat   300
gccgcaacgc cgcgtgcaga ggcaagacgc acgccgagg caactgccga tgccagcgca    360
ccgcgtagag gggcggttgc acacgccaac agtatcgttc agcaattggt cagtgagggc   420
gctgatattt cgcatactcg taacatgctc cgcaatgcaa tgaatggcga cgcagtcgct   480
ttttctcgag tagaacagaa catatttcgc cagcatttcc cgaacatgcc catgcatgga   540
atcagccgag attcggaact cgctatcgag ctccgtgggg cgcttcgtcg agcggttcac   600
caacaggcgg cgtcagcgcc agtgaggtcg cccacgccaa caccggccag ccctgcggca   660
tcatcatcgg gcagcagtca gcgttcttta tttggacggt ttgcccgttt gatggcgcca   720
aaccagggac ggtcgtcgaa cactgccgcc tctcagacgc cggtcgacag gagcccgcca   780
cgcgtcaacc aaagacccat acgcgtcgac agggctgcga tgcgtaatcg tggcaatgac   840
gaggcggacg ccgcgctgcg ggggttagta caacaggggg tcaatttaga gcacctgcgc   900
acggcccttg aaagacatgt aatgcagcgc ctccctatcc ccctcgatat aggcagcgcg   960
ttgcagaatg tgggaattaa cccaagtatc gacttggggg aaagccttgt gcaacatccc  1020
ctgctgaatt tgaatgtagc gttgaatcgc atgctggggc tgcgtcccag cgctgaaaga  1080
gcgcctcgtc cagccgtccc cgtggctccc gcgaccgcct ccaggcgacc ggatggtacg  1140
cgtgcaacac gattgcgggt gatgccggag cgggaggatt acgaaaataa tgtggcttat  1200
ggagtgcgct tgcttaacct gaacccgggg gtggggtaa gcaggctgt tgcggccttt  1260
gtaaccgacc gggctgagcg gccagcagtg gtggctaata tccgggcagc cctggaccct  1320
atcgcgtcac aattcagtca gctgcgcaca atttcgaagg ccgatgctga atctgaagag  1380
ctgggtttta aggatgcggc agatcatcac acggatgacg tgacgcactg tcttttttggc  1440
ggagaattgt cgctgagtaa tccggatcag caggtgatcg gtttggcggg taatccgacg  1500
gacacgtcgc agccttacag ccaagaggga aataaggacc tggcgttcat ggatatgaaa  1560
aaacttgccc aattcctcgc aggcaagcct gagcatccga tgaccagaga aacgcttaac  1620
gccgaaaata tcgccaagta tgcttttaga atagtcccct ga                     1662
```

The nucleic acid sequence corresponding to SEQ ID NO:1 encodes a bacterial effector protein identified herein as AvrPtoB (Pst DC3000), which has a deduced amino acid sequence corresponding to SEQ ID NO:2 as follows:

```
Met Ala Gly Ile Asn Arg Ala Gly Pro Ser Gly Ala Tyr Phe Val Gly
 1               5                  10                  15

His Thr Asp Pro Glu Pro Val Ser Gly Gln Ala His Gly Ser Gly Ser
            20                  25                  30

Gly Ala Ser Ser Asn Ser Pro Gln Val Gln Pro Arg Pro Ser Asn
        35                  40                  45

Thr Pro Pro Ser Asn Ala Pro Ala Pro Pro Thr Gly Arg Glu Arg
    50                  55                  60

Leu Ser Arg Ser Thr Ala Leu Ser Arg Gln Thr Arg Glu Trp Leu Glu
65                  70                  75                  80

Gln Gly Met Pro Thr Ala Glu Asp Ala Ser Val Arg Arg Pro Gln
                85                  90                  95
```

-continued

```
Val Thr Ala Asp Ala Ala Thr Pro Arg Ala Glu Ala Arg Arg Thr Pro
            100                 105                 110
Glu Ala Thr Ala Asp Ala Ser Ala Pro Arg Arg Gly Ala Val Ala His
        115                 120                 125
Ala Asn Ser Ile Val Gln Gln Leu Val Ser Gly Ala Asp Ile Ser
    130                 135                 140
His Thr Arg Asn Met Leu Arg Asn Ala Met Asn Gly Asp Ala Val Ala
145                 150                 155                 160
Phe Ser Arg Val Glu Gln Asn Ile Phe Arg Gln His Phe Pro Asn Met
                165                 170                 175
Pro Met His Gly Ile Ser Arg Asp Ser Glu Leu Ala Ile Glu Leu Arg
            180                 185                 190
Gly Ala Leu Arg Arg Ala Val His Gln Gln Ala Ser Ala Pro Val
        195                 200                 205
Arg Ser Pro Thr Pro Thr Pro Ala Ser Pro Ala Ala Ser Ser Ser Gly
    210                 215                 220
Ser Ser Gln Arg Ser Leu Phe Gly Arg Phe Ala Arg Leu Met Ala Pro
225                 230                 235                 240
Asn Gln Gly Arg Ser Ser Asn Thr Ala Ala Ser Gln Thr Pro Val Asp
                245                 250                 255
Arg Ser Pro Pro Arg Val Asn Gln Arg Pro Ile Arg Val Asp Arg Ala
            260                 265                 270
Ala Met Arg Asn Arg Gly Asn Asp Glu Ala Asp Ala Ala Leu Arg Gly
        275                 280                 285
Leu Val Gln Gln Gly Val Asn Leu Glu His Leu Arg Thr Ala Leu Glu
    290                 295                 300
Arg His Val Met Gln Arg Leu Pro Ile Pro Leu Asp Ile Gly Ser Ala
305                 310                 315                 320
Leu Gln Asn Val Gly Ile Asn Pro Ser Ile Asp Leu Gly Glu Ser Leu
                325                 330                 335
Val Gln His Pro Leu Leu Asn Leu Asn Val Ala Leu Asn Arg Met Leu
            340                 345                 350
Gly Leu Arg Pro Ser Ala Glu Arg Ala Pro Arg Pro Ala Val Pro Val
        355                 360                 365
Ala Pro Ala Thr Ala Ser Arg Arg Pro Asp Gly Thr Arg Ala Thr Arg
    370                 375                 380
Leu Arg Val Met Pro Glu Arg Glu Asp Tyr Glu Asn Asn Val Ala Tyr
385                 390                 395                 400
Gly Val Arg Leu Leu Asn Leu Asn Pro Gly Val Gly Val Arg Gln Ala
                405                 410                 415
Val Ala Ala Phe Val Thr Asp Arg Ala Glu Arg Pro Ala Val Val Ala
            420                 425                 430
Asn Ile Arg Ala Ala Leu Asp Pro Ile Ala Ser Gln Phe Ser Gln Leu
        435                 440                 445
Arg Thr Ile Ser Lys Ala Asp Ala Glu Ser Glu Leu Gly Phe Lys
    450                 455                 460
Asp Ala Ala Asp His His Thr Asp Asp Val Thr His Cys Leu Phe Gly
465                 470                 475                 480
Gly Glu Leu Ser Leu Ser Asn Pro Asp Gln Gln Val Ile Gly Leu Ala
                485                 490                 495
Gly Asn Pro Thr Asp Thr Ser Gln Pro Tyr Ser Gln Glu Gly Asn Lys
            500                 505                 510
```

-continued
```
Asp Leu Ala Phe Met Asp Met Lys Lys Leu Ala Gln Phe Leu Ala Gly
        515                 520                 525

Lys Pro Glu His Pro Met Thr Arg Glu Thr Leu Asn Ala Glu Asn Ile
    530                 535                 540

Ala Lys Tyr Ala Phe Arg Ile Val Pro
545                 550
```

This bacterial effector protein has a molecular mass from 55-65 kDa.

In another aspect of the present invention, another suitable bacterial effector protein of the present invention is identified herein as avrPtoB (H Pst T1) and is encoded by a nucleic acid molecule having a nucleotide sequence of SEQ ID NO:3 as follows:

```
atggcgggta tcaatggagc gggaccatcg ggcgcttatt ttgttggcca cacagacccc    60
gagccagcat cggggggcgc acacggatcc agcagtggcg cgagatcctc gaacagtccg   120
cgcttgccgg cgcctccgga tgcacccgcg tcgcaggcgc gagatcgacg cgaaatgctt   180
ttgcgagcca ggccgctgtc gcgccaaacc agggagtggg tggcgcaggg tatgccgcca   240
acggcggagg ctggagtgcc catcaggccg caggagtctg ccgaggctgc agcgccgcag   300
gcacgtgcag aggaaagaca cacgccggag gctgatgcag cagcgtcgca tgtacgcaca   360
gagggaggac gcacaccgca ggcgcttgcc ggtacctccc cacgccacac aggtgcggtg   420
ccacacgcca atagaattgt tcaacaattg gttgacgcgg gcgctgatct tgccggtatt   480
aacaccatga ttgacaatgc catgcgtcgc cacgcgatag ctcttccttc tcgaacagta   540
cagagtattt tgatcgagca tttccctcac ctgctagcgg gtgaactcat tagtggctca   600
gagctcgcta ccgcgttccg tgcggctctc cgtcgggagg ttcgccaaca ggaggcgtca   660 gccccccaa gaacagcagc gcggtcctcc gtaaggacgc cggagcggtc gacggtgccg    720
cccacttcta cggaatcatc atcgggcagc aaccagcgta cgttattagg gcggttcgcc   780
gggttgatga cgcctaatca gagacgtccg tcgagcgctt cgaacgcgtc tgcctctcaa   840
aggcctgtag acagaagccc gccacgcgta accaggtac ccacaggcgc taacagggtt    900
gtgatgcgta atcatggtaa taacgaggcc gacgccgcgc tgcaaggatt ggctcagcag   960
ggggttgata tggaggacct gcgcgccgcg cttgaaagac atatattgca tcgccgcccg  1020
atccccatgg atatagcgta cgccttgcag ggtgtgggca ttgcgccaag tatcgatacg  1080
ggagagagcc ttatggaaaa cccgctgatg aatttgagtg ttgcgctgca ccgcgcacta  1140
gggcctcgtc ccgctcgtgc tcaagcgcct cgtccagccg ttccggtggc tcccgcgacc  1200
gtctccaggc gaccagatag cgcgcgtgcc acaagattgc aggtaatacc ggcgcgggag  1260
gattacgaaa ataatgtggc ctacggagtg cgcttgctga gcctgaatcc gggcgcgggg  1320
gtcagggaga ctgttgcggc cttttgtaaac aaccgttacg agcggcaggc ggttgttgcc  1380
gacatacgcg cagccctaaa tttatctaaa caattcaata agttgcgtac ggtctctaag  1440
gccgatgctg cctccaataa accgggcttc aaggatgcgg cggaccaccc agacgacgcg  1500
acgcaatgcc tttttggtga agaattgtcg ctgaccagtt cggatcagca ggtgatcggc  1560
ctggcaggta aggcaacgga catgtcggag tcttacagcc gagaggcaaa taaggacctg  1620
gtgttcatgg atatgaaaaa acttgcccaa ttcctcgcag gcaagcctga gcatccgatg  1680
accagagaaa cgcttaacgc cgaaaatatc gccaagtatg cttttagaat agtcccctga  1740
```

The nucleic acid sequence corresponding to SEQ ID NO:3 encodes a bacterial effector protein identified herein as AvrP-toB (H Pst T1), which has a deduced amino acid sequence corresponding to SEQ ID NO:4 as follows:

```
Met Ala Gly Ile Asn Gly Ala Gly Pro Ser Gly Ala Tyr Phe Val Gly
 1               5                  10                  15
His Thr Asp Pro Glu Pro Ala Ser Gly Gly Ala His Gly Ser Ser Ser
                20                  25                  30
Gly Ala Arg Ser Ser Asn Ser Pro Arg Leu Pro Ala Pro Pro Asp Ala
            35                  40                  45
Pro Ala Ser Gln Ala Arg Asp Arg Arg Glu Met Leu Leu Arg Ala Arg
        50                  55                  60
Pro Leu Ser Arg Gln Thr Arg Glu Trp Val Ala Gln Gly Met Pro Pro
 65                 70                  75                  80
Thr Ala Glu Ala Gly Val Pro Ile Arg Pro Gln Glu Ser Ala Glu Ala
                85                  90                  95
Ala Ala Pro Gln Ala Arg Ala Glu Glu Arg His Thr Pro Glu Ala Asp
               100                 105                 110
Ala Ala Ala Ser His Val Arg Thr Glu Gly Gly Arg Thr Pro Gln Ala
           115                 120                 125
Leu Ala Gly Thr Ser Pro Arg His Thr Gly Ala Val Pro His Ala Asn
       130                 135                 140
Arg Ile Val Gln Gln Leu Val Asp Ala Gly Ala Asp Leu Ala Gly Ile
145                 150                 155                 160
Asn Thr Met Ile Asp Asn Ala Met Arg Arg His Ala Ile Ala Leu Pro
               165                 170                 175
Ser Arg Thr Val Gln Ser Ile Leu Ile Glu His Phe Pro His Leu Leu
           180                 185                 190
Ala Gly Glu Leu Ile Ser Gly Ser Glu Leu Ala Thr Ala Phe Arg Ala
       195                 200                 205
Ala Leu Arg Arg Glu Val Arg Gln Gln Glu Ala Ser Ala Pro Pro Arg
   210                 215                 220
Thr Ala Ala Arg Ser Ser Val Arg Thr Pro Glu Arg Ser Thr Val Pro
225                 230                 235                 240
Pro Thr Ser Thr Glu Ser Ser Ser Gly Ser Asn Gln Arg Thr Leu Leu
               245                 250                 255
Gly Arg Phe Ala Gly Leu Met Thr Pro Asn Gln Arg Arg Pro Ser Ser
           260                 265                 270
Ala Ser Asn Ala Ser Ala Ser Gln Arg Pro Val Asp Arg Ser Pro Pro
       275                 280                 285
Arg Val Asn Gln Val Pro Thr Gly Ala Asn Arg Val Val Met Arg Asn
   290                 295                 300
His Gly Asn Asn Glu Ala Asp Ala Ala Leu Gln Gly Leu Ala Gln Gln
305                 310                 315                 320
Gly Val Asp Met Glu Asp Leu Arg Ala Ala Leu Glu Arg His Ile Leu
               325                 330                 335
His Arg Arg Pro Ile Pro Met Asp Ile Ala Tyr Ala Leu Gln Gly Val
           340                 345                 350
Gly Ile Ala Pro Ser Ile Asp Thr Gly Glu Ser Leu Met Glu Asn Pro
       355                 360                 365
Leu Met Asn Leu Ser Val Ala Leu His Arg Ala Leu Gly Pro Arg Pro
   370                 375                 380
Ala Arg Ala Gln Ala Pro Arg Pro Ala Val Pro Val Ala Pro Ala Thr
385                 390                 395                 400
```

-continued

```
Val Ser Arg Arg Pro Asp Ser Ala Arg Ala Thr Arg Leu Gln Val Ile
            405                 410                 415

Pro Ala Arg Glu Asp Tyr Glu Asn Asn Val Ala Tyr Gly Val Arg Leu
            420                 425                 430

Leu Ser Leu Asn Pro Gly Ala Gly Val Arg Glu Thr Val Ala Ala Phe
            435                 440                 445

Val Asn Asn Arg Tyr Glu Arg Gln Ala Val Val Ala Asp Ile Arg Ala
            450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Ala Ala Asp His
                485                 490                 495

Pro Asp Asp Ala Thr Gln Cys Leu Phe Gly Glu Glu Leu Ser Leu Thr
            500                 505                 510

Ser Ser Asp Gln Gln Val Ile Gly Leu Ala Gly Lys Ala Thr Asp Met
            515                 520                 525

Ser Glu Ser Tyr Ser Arg Glu Ala Asn Lys Asp Leu Val Phe Met Asp
            530                 535                 540

Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
                565                 570                 575

Ile Val Pro
```

This bacterial effector protein has a molecular mass from 55-65 kDa.

Another suitable bacterial effector protein of the present invention is identified herein as avrPtoB (H Pst PT23) and is encoded by a nucleic acid molecule having a nucleotide sequence of SEQ ID NO:5 as follows:

```
atggcgggta tcaatggagc gggaccatcg ggcgcttatt tgttggcca cacagacccc    60 gagccagcat cgggggggcgc acacggatcc agcagtggcg caagctcctc gaacagtccg   120
cgcttgccgg cgcctccgga tgcacccgcg tcgcaggcgc gagatcgacg cgaaatgctt   180
ttgcgagcca ggccgctgtc gcgccaaacc agggagtggg tggcgcaggg tatgccgcca   240
acggcggagg ctggagtgcc catcaggccg caggagtctg ccgaggctgc agcgccgcag   300
gcacgtgcag aggaaagaca cacgccggag gctgatgcag cagcgtcgca tgtacgcaca   360
gagggaggac gcacaccgca ggcgcttgcc ggtacctccc cacgccacac aggtgcggtg   420
ccacacgcca atagaattgt tcaacaattg gttgacgcgg cgctgatct tgccggtatt    480 aacaccatga ttgacaatgc catgcgtcgc cacgcgatag ctcttccttc tcgaacagta   540
cagagtattt tgatcgagca tttccctcac ctgctagcgg gtgaactcat tagtggctca   600
gagctcgcta ccgcgttccg tgcggctctc cgtcgggagg ttcgccaaca ggaggcgtca   660 gccccccaa gaacaacagc gcggtcctcc gtaaggacgc cggagcggtc gacggtgccg    720
cccacttcta cggaatcatc atcgggcagc aaccagcgta cgttattagg gcggttcgcc   780
gggttgatga cgcctaatca gagacgtccg tcgagcgctt cgaacgcgtc tgcctctcaa   840
aggcctgtag acagaagccc gccacgcgta aaccaggtac ccacaggcgc taacagggtt   900
gtgatgcgta atcatggtaa taacgaggcc gacgccgcgc tgcaaggatt ggctcagcag   960
ggggttgata tggaggacct gcgcgccgcg cttgaaagac atatattgca tcgccgcccg  1020
```

```
atccccatgg atatagcgta cgccttgcag ggcgtgggca ttgcgccaag tatcgatacg   1080
ggagagagcc ttatggaaan cccgctgatg aatttgagtg ttgcgctgca ccgcgcacta   1140
gggcctcgtc ccgctcgtgc tcaagcgcct cgtccagccg ttccggtggc tcccgcgacc   1200
gtctccaggc gaccagatag cgcgcgtgcc acaagattgc aggtaatacc ggcgcgggag   1260
gattacgaaa ataatgtggc ctacggagtg cgcttgctga gcctgaatcc gggcgcgtgg   1320
gtcagggaga ctgttgcggc ctttgtaaac aaccgttacg agcggcaggc ggttgttgcc   1380
gacatacgcg cagccctaaa tttatctaaa caattcaata agttgcgtac ggtctctaag   1440
gccgatgctg cctccaataa accgggcttc aaggatctgg cggaccaccc agacgacgcg   1500
acgcaatgcc tttttggtga agaattgtcg ctgaccagtt cggttcagca ggtgatcggc   1560
ctggcaggta aggcaacgga catgtcggag tcttacagcc gagaggcaaa taaggacctg   1620
gtgttcatgg atatgaaaaa acttgcccaa ttcctcgcag gcaagcctga gcatccgatg   1680
accagagaaa cgcttaacgc cgaaaatatc gccaagtatg cttttagaat agtcccctga   1740
```

The nucleic acid sequence corresponding to SEQ ID NO:5 encodes a bacterial effector protein identified herein as AvrP-toB (H Pst PT23), which has a deduced amino acid sequence corresponding to SEQ ID NO:6 as follows:

```
Met Ala Gly Ile Asn Gly Ala Gly Pro Ser Gly Ala Tyr Phe Val Gly
  1               5                  10                  15

His Thr Asp Pro Glu Pro Ala Ser Gly Gly Ala His Gly Ser Ser Ser
             20                  25                  30

Gly Ala Ser Ser Ser Asn Ser Pro Arg Leu Pro Ala Pro Pro Asp Ala
         35                  40                  45

Pro Ala Ser Gln Ala Arg Asp Arg Arg Glu Met Leu Leu Arg Ala Arg
     50                  55                  60

Pro Leu Ser Arg Gln Thr Arg Glu Trp Val Ala Gln Gly Met Pro Pro
 65                  70                  75                  80

Thr Ala Glu Ala Gly Val Pro Ile Arg Pro Gln Glu Ser Ala Glu Ala
                 85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
        115                 120                 125

Leu Ala Gly Thr Ser Pro Arg His Thr Gly Ala Val Pro His Ala Asn
    130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
            180                 185                 190

Ala Gly Glu Leu Ile Ser Gly Ser Glu Leu Ala Thr Ala Phe Arg Ala
        195                 200                 205

Ala Leu Arg Arg Glu Val Arg Gln Gln Glu Ala Ser Ala Pro Pro Arg
    210                 215                 220

Thr Thr Ala Arg Ser Ser Val Arg Thr Pro Glu Arg Ser Thr Val Pro
225                 230                 235                 240

Pro Thr Ser Thr Glu Ser Ser Gly Ser Asn Gln Arg Thr Leu Leu
                245                 250                 255
```

```
        Gly Arg Phe Ala Gly Leu Met Thr Pro Asn Gln Arg Arg Pro Ser Ser
                        260                 265                 270
        Ala Ser Asn Ala Ser Ala Ser Gln Arg Pro Val Asp Arg Ser Pro Pro
                    275                 280                 285
        Arg Val Asn Gln Val Pro Thr Gly Ala Asn Arg Val Val Met Arg Asn
                290                 295                 300
        His Gly Asn Asn Glu Ala Asp Ala Ala Leu Gln Gly Leu Ala Gln Gln
        305                 310                 315                 320
        Gly Val Asp Met Glu Asp Leu Arg Ala Leu Glu Arg His Ile Leu
                        325                 330                 335
        His Arg Arg Pro Ile Pro Met Asp Ile Ala Tyr Ala Leu Gln Gly Val
                        340                 345                 350
        Gly Ile Ala Pro Ser Ile Asp Thr Gly Glu Ser Leu Met Glu Xaa Pro
                        355                 360                 365
        Leu Met Asn Leu Ser Val Ala Leu His Arg Ala Leu Gly Pro Arg Pro
                    370                 375                 380
        Ala Arg Ala Gln Ala Pro Arg Pro Ala Val Pro Val Ala Pro Ala Thr
        385                 390                 395                 400
        Val Ser Arg Arg Pro Asp Ser Ala Arg Ala Thr Arg Leu Gln Val Ile
                        405                 410                 415
        Pro Ala Arg Glu Asp Tyr Glu Asn Asn Val Ala Tyr Gly Val Arg Leu
                        420                 425                 430
        Leu Ser Leu Asn Pro Gly Ala Trp Val Arg Glu Thr Val Ala Ala Phe
                    435                 440                 445
        Val Asn Asn Arg Tyr Glu Arg Gln Ala Val Val Ala Asp Ile Arg Ala
                450                 455                 460
        Ala Leu Asn Leu Ser Lys Gln Phe Asn Lys Leu Arg Thr Val Ser Lys
        465                 470                 475                 480
        Ala Asp Ala Ala Ser Asn Lys Pro Gly Phe Lys Asp Leu Ala Asp His
                        485                 490                 495
        Pro Asp Asp Ala Thr Gln Cys Leu Phe Gly Glu Leu Ser Leu Thr
                    500                 505                 510
        Ser Ser Val Gln Gln Val Ile Gly Leu Ala Gly Lys Ala Thr Asp Met
                    515                 520                 525
        Ser Glu Ser Tyr Ser Arg Glu Ala Asn Lys Asp Leu Val Phe Met Asp
                    530                 535                 540
        Met Lys Lys Leu Ala Gln Phe Leu Ala Gly Lys Pro Glu His Pro Met
        545                 550                 555                 560
        Thr Arg Glu Thr Leu Asn Ala Glu Asn Ile Ala Lys Tyr Ala Phe Arg
                        565                 570                 575
        Ile Val Pro
```

This bacterial effector protein has a molecular mass from 55-65 kDa.

Another suitable bacterial effector protein of the present invention is identified herein as avrPtoB (H Pst JL1065) and is encoded by a nucleic acid molecule having a nucleotide sequence of SEQ ID NO:7 as follows:

```
atggcgggta tcaatggagc gggaccatcg ggcgcttatt ttgttggcca cacagacccc    60
gagccagcat cgggggggcgc acacggatcc agcagtggcg caagctcctc gaacagtccg   120
cgcttgccgg cgcctccgga tgcacccgcg tcgcaggcgc gagatcgacg cgaaatgctt   180
```

-continued

```
ttgcgagcca ggccgctgtc gcgccaaacc agggagtggg tggcgcaggg tatgccgcca    240
acggcggagg ctggagtgcc catcaggccg caggagtctg ccgaggctgc agcgccgcag    300
gcacgtgcag aggaaagaca cacgccggag gctgatgcag cagcgtcgca tgtacgcaca    360
gagggaggac gcacaccgca ggcgcttgcc ggtacctccc cacgccacac aggtgcggtg    420
ccacacgcca atagaattgt tcaacaattg gttgacgcgg gcgctgatct tgccggtatt    480
aacaccatga ttgacaatgc catgcgtcgc cacgcgatag ctcttccttc tcgaacagta    540
cagagtattt tgatcgagca tttccctcac ctgctagcgg gtgaactcat tagtggctca    600
gagctcgcta ccgcgttccg tgcggctctc cgtcgggagg ttcgccaaca ggaggcgtca    660
gcccccccaa gaacagcagc gcggtcctcC gtaaggacgc cggagcggtc gacggtgccg    720
cccacttcta cggaatcatc atcgggcagc aaccagcgta cgttattagg gcggttcgcc    780
gggttgatga cgcctaatca gagacgtccg tcgagcgctt cgaacgcgtc tgcctctcaa    840
aggcctgtag acagaagccc gccacgcgta aaccaggtac ccacaggcgc taacagggtt    900
gtgatgcgta atcatggtaa taacgaggcc gacgccgcgc tgcaaggatt ggctcagcag    960
ggggttgata tggaggacct gcgcgccgcg cttgaaagac atatattgca tcgccgcccg   1020
atccccatgg atatagcgta cgccttgcag ggtgtgggca ttgcgccaag tatcgatacg   1080
ggagagagcc ttatggaaaa cccgctgatg aatttgagtg ttgcgctgca ccgcgcacta   1140
gggcctcgtc ccgctcgtgc tcaagcgcct cgtccagccg ttccggtggc tcccgcgacc   1200
gtctccaggc gaccagatag cgcgcgtgcc acaagattgc aggtaatacc ggcgcgggag   1260
gattacgaaa ataatgtggc ctacgagtg cgcttgctga gcctgaatcc gggcgcgggg   1320
gtcagggaga ctgttgcggc ctttgtaaac aaccgttacg agcggcaggc ggttgttgcc   1380
gacatacgcg cagccctaaa tttatctaaa caattcaata agttgcgtac ggtctctaag   1440
gccgatgctg cctccaataa accgggcttc aaggatctgg cggaccacCc agacgacgcg   1500
acgcaatgcc ttttggtga agaattgtcg ctgaccagtt cggttcagca ggtgatcggc   1560
ctggcaggta aggcaacgga catgtcggag tcttacagcc gagaggcaaa taaggacctg   1620
gtgttcatgg atatgaaaaa acttgcccaa ttcctcgcag gcaagcctga gcatccgatg   1680
accagagaaa cgcttaacgc cgaaaatatc gccaagtatg cttttagaat agtcccctga   1740
```

The nucleic acid sequence corresponding to SEQ ID NO:7 encodes a bacterial effector protein identified herein as AvrP-toB (H Pst JL1065), which has a deduced amino acid sequence corresponding to SEQ ID NO:8 as follows:

```
Met Ala Gly Ile Asn Gly Ala Gly Pro Ser Gly Ala Tyr Phe Val Gly
 1               5                  10                  15

His Thr Asp Pro Glu Pro Ala Ser Gly Gly Ala His Gly Ser Ser Ser
                20                  25                  30

Gly Ala Ser Ser Ser Asn Ser Pro Arg Leu Pro Ala Pro Pro Asp Ala
            35                  40                  45

Pro Ala Ser Gln Ala Arg Asp Arg Arg Glu Met Leu Leu Arg Ala Arg
        50                  55                  60

Pro Leu Ser Arg Gln Thr Arg Glu Trp Val Ala Gln Gly Met Pro Pro
65                  70                  75                  80

Thr Ala Glu Ala Gly Val Pro Ile Arg Pro Gln Glu Ser Ala Glu Ala
                85                  90                  95

Ala Ala Pro Gln Ala Arg Ala Glu Glu Arg His Thr Pro Glu Ala Asp
            100                 105                 110
```

-continued

```
Ala Ala Ala Ser His Val Arg Thr Glu Gly Gly Arg Thr Pro Gln Ala
            115                 120                 125

Leu Ala Gly Thr Ser Pro Arg His Thr Gly Ala Val Pro His Ala Asn
        130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
            180                 185                 190

Ala Gly Glu Leu Ile Ser Gly Ser Leu Ala Thr Ala Phe Arg Ala
        195                 200                 205

Ala Leu Arg Arg Glu Val Arg Gln Gln Glu Ala Ser Ala Pro Pro Arg
    210                 215                 220

Thr Ala Ala Arg Ser Ser Val Arg Thr Pro Glu Arg Ser Thr Val Pro
225                 230                 235                 240

Pro Thr Ser Thr Glu Ser Ser Gly Ser Asn Gln Arg Thr Leu Leu
                245                 250                 255

Gly Arg Phe Ala Gly Leu Met Thr Pro Asn Gln Arg Pro Ser Ser
            260                 265                 270

Ala Ser Asn Ala Ser Ala Ser Gln Arg Pro Val Asp Arg Ser Pro Pro
        275                 280                 285

Arg Val Asn Gln Val Pro Thr Gly Ala Asn Arg Val Val Met Arg Asn
    290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
            340                 345                 350

Gly Ile Ala Pro Ser Ile Asp Thr Gly Glu Ser Leu Met Glu Asn Pro
        355                 360                 365

Leu Met Asn Leu Ser Val Ala Leu His Arg Ala Leu Gly Pro Arg Pro
    370                 375                 380

Ala Arg Ala Gln Ala Pro Arg Pro Ala Val Pro Val Ala Pro Ala Thr
385                 390                 395                 400

Val Ser Arg Arg Pro Asp Ser Ala Arg Ala Thr Arg Leu Gln Val Ile
                405                 410                 415

Pro Ala Arg Glu Asp Tyr Glu Asn Asn Val Ala Tyr Gly Val Arg Leu
            420                 425                 430

Leu Ser Leu Asn Pro Gly Ala Gly Val Arg Glu Thr Val Ala Ala Phe
        435                 440                 445

Val Asn Asn Arg Tyr Glu Arg Gln Ala Val Val Ala Asp Ile Arg Ala
    450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Leu Ala Asp His
                485                 490                 495

Pro Asp Asp Ala Thr Gln Cys Leu Phe Gly Glu Glu Leu Ser Leu Thr
            500                 505                 510

Ser Ser Val Gln Gln Val Ile Gly Leu Ala Gly Lys Ala Thr Asp Met
        515                 520                 525

Ser Glu Ser Tyr Ser Arg Glu Ala Asn Lys Asp Leu Val Phe Met Asp
    530                 535                 540
```

-continued

```
Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
                565                 570                 575

Ile Val Pro
```

This bacterial effector protein has a molecular mass from 55-65 kDa.

Also suitable in all aspects of the present invention are bacterial effector proteins which have an amino acid sequence spanning amino acids 308 and 553 of avrPtoB (PstDC3000) (SEQ ID NO:2).

Based on the avrPtoB (PstDC3000) amino acid comparisons described in FIGS. 7A-E, regions of highly conserved amino acid sequences were identified. Identification of these regions further enabled identification of specific motifs throughout the conserved region of avrPtoB (PstDC3000). As a result of this analysis, several blocks of 5 or more identical amino acids were found as shown in Table 1 below.

TABLE 1

| Location in avrPtoB (PstDC3000) | Motif | |
|---|---|---|
| 7-22 | AGPSGAYFVGHTDPEP | (SEQ ID NO: 9) |
| 32-40 | SGASSSNSP | (SEQ ID NO: 10) |
| 71-78 | LSRQTREW | (SEQ ID NO: 11) |
| 132-137 | IVQQLV | (SEQ ID NO: 12) |
| 221-225 | SSSGS | (SEQ ID NO: 13) |
| 254-264 | PVDRSPPRVNQ | (SEQ ID NO: 14) |
| 361-372 | APRPAVPVAPAT | (SEQ ID NO: 15) |
| 374-378 | SRRPD | (SEQ ID NO: 16) |
| 381-385 | RATRL | (SEQ ID NO: 17) |
| 391-405 | REDYENNVAYGVRLL | (SEQ ID NO: 18) |
| 417-421 | VAAFV | (SEQ ID NO: 19) |
| 434-438 | IRAAL | (SEQ ID NO: 20) |
| 452-456 | SKADA | (SEQ ID NO: 21) |
| 490-497 | QQVIGLAG | (SEQ ID NO: 22) |
| 516-553 | FMDMKKLAQFLAGKPEHPM TRETLNAENIAKYAFRIVP | (SEQ ID NO: 23) |

The information presented in Table 1 can be combined to define the protein of the present invention as having amino acid sequence of SEQ ID NO: 24 (with X being any amino acid) as follows:

| (6X) | AGPSGAYFVGHTDPEP |
|---|---|
| (9X) | SGASSSNSP |
| (30X) | LSRQTREW |
| (53X) | IVQQLV |
| (83X) | SSSGS |
| (28X) | PVDRSPPRVNQ |
| (96X) | APRPAVPVAPAT |
| (X) | SRRPD |
| (2X) | RATRL |
| (5X) | REDYENNVAYGVRLL |
| (11X) | VAAFV |
| (12X) | IRAAL |
| (13X) | SKADA |
| (33X) | QQVIGLAG |
| (18X) | FMDMKKLAQFLAGKPEHPMTRETLNAENIAKYAFRIVP |

Also suitable in all aspects of the present invention are bacterial effector proteins which have an amino acid sequence spanning a C-terminus of SEQ ID NO:2, SEQ ID NO:4, SEQ ID NO:6, or SEQ ID NO:8.

Fragments of the above bacterial effector proteins are encompassed by the present invention.

Suitable fragments can be produced by several means. In one method, subclones of the genes encoding the bacterial effector protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein, fragments of a bacterial effector protein encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for a bacterial effector protein being produced. Alternatively, subjecting a full length bacterial effector protein to high temperatures and pressures will produce fragments. These fragments can then be separated by conventional procedures (e.g., chromatography, SDS-PAGE).

Mutations or variants of the above polypeptides or proteins are encompassed by the present invention. Variants may be made by, for example, the deletion or addition of amino acids that have minimal influence on the properties, secondary structure, and hydropathic nature of a polypeptide or protein. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as an isolated nucleic acid molecule according to the present invention is a nucleic acid molecule having a nucleotide sequence that is at least 85% similar, to the nucleotide sequence of SEQ ID NO:1, SEQ ID NO:3, SEQ ID NO:5, or SEQ ID NO:7 of the present invention by basic BLAST using default parameters analysis.

Suitable nucleic acid molecules are those that hybridize to a nucleic acid molecule comprising a nucleotide sequence of SEQ ID NO:1, SEQ ID NO:3, SEQ ID NO:5, or SEQ ID NO:7 of the present invention under stringent conditions. For the purposes of defining the level of stringency, reference can conveniently be made to Sambrook et al., *Molecular Cloning: a Laboratory Manual* $2^{nd}$ Edition, Cold Spring Harbor, N.Y., Cold Spring Harbor Laboratory Press, at 11.45 (1989). An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at $\geq 45°$ C. for 2-3 hours. An example of high stringency conditions includes 0.1-1×SSC/0.1% w/v SDS at 60° C. for 1-3 hours. The skilled artisan is aware of various parameters which may be altered during hybridization and washing and which will either maintain or change the stringency conditions. Other examples of high stringency conditions include: 4-5×SSC/0.1% w/v SDS at 54° C. for 1-3 hours and 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

The precise conditions for any particular hybridization are left to those skilled in the art, because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

A bacterial effector protein of the present invention is preferably produced in purified form (e.g., at least about 85% pure) by conventional techniques. For example, a bacterial effector protein of the present invention may be secreted into the growth medium of recombinant host cells. To isolate the bacterial effector protein, a protocol involving a host cell such as Escherichia coli may be used, in which protocol the *E. coli* host cell carrying a recombinant plasmid is propagated, homogenized, and the homogenate is centrifuged to remove bacterial debris. The supernatant is then subjected to sequential ammonium sulfate precipitation. The fraction containing the bacterial effector protein of the present invention is subjected to gel filtration in an appropriately sized dextran or polyacrylamide column to separate the proteins or polypeptides. If necessary, the protein fraction may be further purified by high performance liquid chromatography ("HPLC").

Another aspect of the present invention pertains to host cells, transgenic plants, and transgenic plant seeds containing a nucleic acid molecule encoding a bacterial effector protein which inhibits programmed cell death in eukaryotes.

The present invention relates to a nucleic acid construct that contains a nucleic acid molecule encoding for a bacterial effector protein. This involves incorporating one or more of the nucleic acid molecules of the present invention, or a suitable portion thereof, into host cells using conventional recombinant DNA technology. Generally, this involves inserting the nucleic acid molecule into an expression system to which the nucleic acid molecule is heterologous (i.e. not normally present). The expression system contains the necessary elements for the transcription and translation of the inserted protein-coding sequences.

The present invention also relates to an expression vector containing a nucleic acid molecule encoding a bacterial effector protein of the present invention. The nucleic acid molecules of the present invention may be inserted into any of the many available expression vectors and cell systems using reagents that are well known in the art. In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for transformation. The selection of a vector will depend on the preferred transformation technique and target cells for transfection.

Suitable vectors include, but are not limited to, the following viral vectors such as lambda vector system gt11, gt WS.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), pCB201, and any derivatives thereof. Any appropriate vectors now known or later described for genetic transformation are suitable for use with the present invention. Recombinant molecules can be introduced into cells via transformation, particularly transduction, conjugation, mobilization, or electroporation. The nucleic acid sequences are cloned into the vector using standard cloning procedures in the art, as described by Sambrook et al., *Molecular Cloning: A Laboratory Manual* Second Edition, Cold Spring Harbor Press, N.Y. (1989), and Ausubel, F. M. et al. (1989) *Current Protocols in Molecular Biology* John Wiley & Sons, New York, N.Y., which are hereby incorporated by reference in their entirety.

U.S. Pat. No. 4,237,224, issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria The expression elements of these vectors vary in their strength and specificities. Depending upon the host-vector system utilized, any one of a number of suitable transcription and translation elements can be used.

Thus, certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. A constitutive promoter is a promoter that directs expression of a gene throughout the development and life of an organism. An inducible promoter is a promoter that is capable of directly or indirectly activating transcription of one or more nucleic acid sequences or genes in response to an inducer. In the absence of an inducer, the nucleic acid sequences or genes will not be transcribed or will only be minimally transcribed.

The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in $E.\ coli$, its bacteriophages, or plasmids, promoters such as the T7 phage promoter, lac promotor, trp promotor, recA promoter, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other $E.\ coli$ promotors produced by recombinant DNA or other synthetic DNA techniques may be used to provide for transcription of the inserted gene.

Other examples of some constitutive promoters that are widely used for inducing expression of transgenes include the nopoline synthase (NOS) gene promoter, from *Agrobacterium tumefaciens*, (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter derived from the cellular elongation factor 1α gene.

Bacterial host cell strains and expression vectors may be chosen which inhibit the action of the promoter unless specifically induced. In certain operations, the addition of specific inducers is necessary for efficient transcription of the inserted nucleic acid. For example, the lac operon is induced by the addition of lactose or IPTG (isopropylthio-beta-D-galactoside). A variety of other operons, such as trp, pro, etc., are under different controls.

Other examples of some inducible promoters, induced, for examples by a chemical agent, such as a metabolite, growth regulator, herbicide or phenolic compound, or a physiological stress/physical means, such as cold, heat, salt, toxins, or through the action of a pathogen or disease agent such as a virus or fungus, include a glucocorticoid-inducible promoter (Schena et al., *Proc. Natl. Acad. Sci.* 88:10421-5 (1991), which is hereby incorporated by reference in its entirety), the heat shock promoter ("Hsp"), IPTG or tetracycline ("Tet on" system), the metallothionine promoter, which is activated by heavy metal ions, and hormone-responsive promoters, which are activated by treatment of certain hormones. A host cell containing an inducible promoter may be exposed to an inducer by externally applying the inducer to the cell. In addition, "tissue-specific" promoters can be used, which are promoters that function in a tissue specific manner to regulate the gene of interest within selected tissues of the host. Examples of such tissue specific promoters include seed, flower, or root specific promoters as are well known in the field (e.g., U.S. Pat. No. 5,750,385 to Shewmaker et al., which is hereby incorporated by reference in its entirety). Promoters of the nucleic acid construct of the present invention may be either homologous (derived from the same species as the host cell) or heterologous (derived from a different species than the host cell).

Specific initiation signals are also required for efficient gene transcription and translation in prokaryotic cells. These transcription and translation initiation signals may vary in "strength" as measured by the quantity of gene specific messenger RNA and protein synthesized, respectively. The nucleic acid expression vector, which contains a promoter, may also contain any combination of various "strong" transcription and/or translation initiation signals. For instance, efficient translation in $E.\ coli$ requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the $E.\ coli$ tryptophan E, D, C, B or A genes. Additionally, any SD-ATG combination produced by recombinant DNA or other techniques involving incorporation of synthetic nucleotides may be used.

The constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid of the present invention.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A nucleic acid molecule of the present invention, promoter of choice, an appropriate 3' regulatory region, and, if desired, a reporter gene, can be incorporated into a vector-expression system which contains the nucleic acids of the present invention, or suitable fragments thereof, using standard cloning techniques as described in Sambrook et al., *Molecular Cloning: A Laboratory Manual*, Second Edition, Cold Spring Harbor Press, N.Y. (1989), and Ausubel et al. (1989) *Current Protocols in Molecular Biolog* John Wiley & Sons, New York, N.Y., which are hereby incorporated by reference in their entirety. The transcriptional and translational elements are operably linked to the nucleic acid molecule of the present invention or a fragment thereof, meaning that the resulting vector expresses the bacterial effector protein when placed in a suitable host cell.

Once an isolated nucleic acid molecule encoding a bacterial effector protein has been cloned into an expression vector, it is ready to be incorporated into a host cell. Such incorporation can be carried out by the various forms of transformation noted above, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1 989), which is hereby incorporated by reference in its entirety. Suitable host cells include, but are not limited to, bacteria, virus, yeast, mammalian cells, insect, plant, invertebrate, eukaryote and the like.

Thus, the present invention also relates to a host cell incorporating one or more of the isolated nucleic acid molecules of the present invention. In one embodiment, the isolated nucleic acid molecule is heterologous to the host cell. Such incorporation can be carried out by the various forms of transformation noted above, depending upon the vector/host system, and using the various host cells described above.

Methods of transformation may result in transient or stable expression of the DNA under control of the promoter. Preferably, the nucleic acid of the present invention is stably inserted into the genome of the host cell as a result of the transformation, although transient expression can serve an important purpose.

One approach to transforming host cells with a nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression, because the population of cells is very high (on the order of $10^6$). To deliver DNA inside protoplasts, several methodologies have been proposed, but the most common are electroporation (Fromm et al., *Proc. Natl. Acad. Sci. USA* 82:5824-5828 (1985), which is hereby incorporated by reference in its entirety) and polyethylene glycol (PEG) mediated DNA uptake (Krens et al., *Nature* 296:72-74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the nucleic acid molecule of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA* 76:3348-52 (1979), which is hereby incorporated by reference in its entirety).

Stable transformants are preferable for the methods of the present invention. An appropriate method of stably introducing the nucleic acid molecule into plant cells is to infect a plant cell with *Agrobacterium tumefaciens* or *Agrobacterium rhizogenes* previously transformed with a DNA construct of the present invention. Under appropriate conditions known in the art, the transformed plant cells are grown to form shoots or roots, and develop further into plants.

Plant tissues suitable for transformation include without limitation, floral buds, leaf tissue, root tissue, meristems, zygotic and somatic embryos, megaspores, callus, protoplasts, tassels, pollen, embryos, anthers, and the like. The means of transformation chosen is that most suited to the tissue to be transformed.

Suitable plants include dicots and monocots. Monocots suitable for the present invention include Poaceae (e.g. rice, wheat, barley, rye, and sorghum) Gramineae (e.g., grass, corn, grains, bamboo, and sugar cane), Liliaceae (e.g., onion, garlic, asparagus, tulips, hyacinths, day lily, and aloes), Bromeliaceae (e.g. pineapple), and Musaceae (e.g. banana). Examples of dicots suitable for the present invention include Cruciferae (e.g., mustards, cabbage, cauliflower, broccoli, brussel sprouts, kale, kohlrabi, turnip, and radish), Rosaceae (e.g., raspberry, strawberry, blackberry, peach, apple, pear, quince, cherry, almond, plum, apricot, and rose), Vitaceae (e.g. grape), Leguminosae (e.g., pea, bean, peanut, alfalfa, clover, vetch, redbud, broom, wisteria, lupine, black locust, and acacia), Fabaceae (e.g. soybean), Malvaceae (e.g., cotton, okra, and mallow), Umbelliferae (e.g., carrot, parsley, parsnips, and hemlock), Solanaceae (e.g., potato, tomato, pepper, eggplant, tobacco, henbane, atropa, physalis, datura, and Petunia), Convolvulaceae (e.g. sweet potato), Cucurbitaceae (e.g., melon, squash, pumpkin, cucumber, and zucchini), Asteraceae (e.g. chicory), Chenopodiaceae (e.g. spinach), Apiaceae (e.g. celery), Compositae (e.g., sunflower, endive, artichoke, lettuce, safflower, aster, marigold, dandelions, sage brush, *Dalia, Chirysanthemum,* and *Zinna*), Brassiceae (e.g. *Arabidopsis thaliana*), Geraniaceae (e.g. pelargonium and *saintpaulia*), and Euphorbiaceae (e.g. poinsettia).

After transformation, the transformed plant cells can be selected and regenerated. Preferably, transformed cells are first identified using a selection marker simultaneously introduced into the host cells along with the DNA construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of a compound identifiable are suitable. The most widely used reporter gene for gene fusion experiments has been uidA, a gene from *Escherichia coli* that encodes the β-glucuronidase protein, also known as GUS (Jefferson et al., *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. It is known that practically all plants can be regenerated from cultured cells or tissues. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. II (1986), which are hereby incorporated by reference in their entirety.

After the nucleic acid construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds or propagules (e.g., cuttings) are recovered from the transgenic plants. The seeds can then be planted in the soil and cultivated using conventional procedures to produce transgenic plants.

Another aspect of the present invention pertains to expression vectors, transgenic plants, and transgenic plant seeds containing a nucleic acid construct having a nucleic acid molecule encoding a first bacterial effector protein of the present invention coupled to a nucleic acid molecule producing a second protein toxic to eukaryotes.

In this aspect of the present invention, the nucleic acid construct includes a nucleic acid molecule encoding a first protein which is a bacterial effector protein of the present invention coupled to a nucleic acid molecule producing a second protein toxic to eukaryotes. Suitable nucleic acid molecules useful in this aspect of the present invention for the first protein include all those encoding the bacterial effector proteins described above. Suitable second proteins include, but are not limited to, the mouse protein Bax and the mutant kinase Pto (Y207D). Suitable methods of preparation of expression vectors, transformation of desired hosts, selection, and regeneration of transformants can be carried out as described above.

The present invention is also directed to a method of suppressing programmed cell death in eukaryotes. This method involves transforming a eukaryote with a nucleic acid encoding a bacterial effector protein which inhibits programmed cell death in eukaryotes. The eukaryote is then grown under conditions effective to suppress programmed cell death in the eukaryote. Suitable nucleic acid molecules useful in this aspect of the present invention include all those encoding the bacterial effector proteins described above. Suitable methods of preparation of expression vectors, transformation of desired hosts, selection, and regeneration of transformants can be carried out as described above.

A further aspect of the present invention relates to a method of delaying senescence in plants. This method includes transforming a plant with a nucleic acid encoding a bacterial effector protein which inhibits programmed cell death in eukaryotes. The plant is then grown under conditions effective to delay senescence in the plant. Suitable methods of preparation of expression vectors, transformation of desired hosts, selection, and regeneration of transformants can be carried out as described above. Suitable plants in accordance with this method of the present invention are described above.

Yet another aspect of the present invention relates to a method of increasing protein expression in plants. This method involves transforming a plant with a nucleic acid encoding a first bacterial effector protein which inhibits programmed cell death in eukaryotes and a second protein which is toxic to plants. The plant is grown under conditions effective to increase expression of the second protein in the plant. Suitable nucleic acid molecules useful in this aspect of the present invention include all those encoding the bacterial effector proteins described above. Suitable methods of preparation of expression vectors, transformation of desired hosts, selection, and regeneration of transformants can be carried out as described above. Suitable plants in accordance with this method of the present invention are described above.

Another aspect of the present invention relates to a method of stabilizing a transgenic plant producing a protein toxic to plants. This method involves providing a transgenic plant transduced with a nucleic acid molecule encoding a first bacterial effector protein and a nucleic acid molecule producing a protein toxic to plants. The plant is grown under conditions effective to stabilize the plant. Suitable nucleic acid molecules useful in this aspect of the present invention include all those encoding the bacterial effector proteins described above. Suitable methods of preparation of expression vectors, transformation of desired hosts, selection, and regeneration of transformants can be carried out as described above. Suitable plants in accordance with this method of the present invention are described above.

Yet another aspect of the present invention relates to a method of treating a subject for a condition mediated to treat the condition mediated by programmed cell death. Conditions which can be treated in accordance with this method include Parkinson's disease, Alzheimer's disease, hepatitis, acute liver injury, and inflammation. This method involves administering to the subject a bacterial effector protein which inhibits programmed cell death, as described above.

EXAMPLES

Example 1

*Agrobacterium*-Mediated Transient Expression

*Agrobacterium*-mediated transient expression was performed as described in Sessa et al., "Thr38 and Ser198 are Pto autophosphorylation sites required for the AvrPto-Pto-mediated hypersensitive response." *EMBO J.* 19: 2257-2269 (2000), which is hereby incorporated by reference in its entirety. Unless indicated otherwise, *A. tumefaciens* strain GV2260 was used to syringe-infiltrate tomato and *N. benthamiana* leaves at a final density of 0.1 and 0.4 $OD_{600\,nm}$, respectively. All genes were expressed from the constitutive 35S CaMV promoter, except for the mouse Bax protein that was expressed from a dexamethasone inducible promoter (Aoyama et al., "A glucocorticoid-mediated transcriptional induction system in transgenic plants." *Plant Journal*, 11: 605-612 (1997), which is hereby incorporated by reference in its entirety). Avr9 and Cf9 constructs and strains are as described in Van der Hoom et al., "Agroinfiltration is a versatile tool that facilitates comparative analyses of Avr9/Cf-9-induced and Avr4/Cf-4-induced necrosis." *MPMI*, 13: 439-446 (2000), which is hereby incorporated by reference in its entirety. Co-expression experiments were performed by mixing *A. tumefaciens* cultures at equal ratios. For controls and to test responses in the absence of individual genes, *A. tumefaciens* carrying the appropriate empty vector replaced the missing component in the mixtures.

Example 2

Plasmid and Strain Construction

All AvrPtoB truncations were generated by PCR using the following primer sets:

|  |  |  |
|---|---|---|
| Δ4, 2-26 and | 5'GTAATGCAGCGCCTCCCTATC3' | (SEQ ID NO: 25) |
| R5 | 5'TCAGGGGACTATTCTAAAAGC3'; | (SEQ ID NO: 26) |
| Δ6, F1 and | 5'ATGGCGGGTATCAATAGAGCG3' | (SEQ ID NO: 27) |
| R4 | 5'TCACACCCGCAATCGTGTTGCAC3'; | (SEQ ID NO: 28) |
| Δ7, F1 and P3 | 5'TCATACATGTCTTTCAAGGGCCG3'. | (SEQ ID NO: 29) |

Truncations were cloned into pCR2.1 (Invitrogen, Carlsbad, Calif.) and sequenced. For yeast two-hybrid bait constructs, the truncations were excised from pCR2.1 using EcoRI and subcloned into the EcoRI site of the pEG202 vector. Yeast two-hybrid analysis was performed as described by Kim et al., "Two distinct *pseudomonas* effector proteins interact with the pto kinase and activate plant immunity." *Cell,* 109: 589-598 (2002), which is hereby incorporated by reference in its entirety. For transient expression, the cloned truncations were excised from pCR2.1 using XbaI and SpeI enzymes and cloned into the XbaI site of the pBTEX binary vector.

DC3000 chromosomal truncations of AvrPtoB were generated using the pKnockout vector and methods as described in Windgassen et al., "Rapid gene inactivation in *Pseudomonas aeruginosa.*" *FEMS Microbiol Lett,* 193: 201-205 (2000), which is hereby incorporated by reference in its entirety. Using an AvrPtoB template, 400-500 bp PCR products were generated using the following primers sets:

|  |  |  |
|---|---|---|
| Mut1: A2MUT1F and | 5'GTATCAATAGAGCGGGACCATC3' | (SEQ ID NO: 30) |
| A2MUT1R | 5'CACTGACCACTTGCTGAACG3'; | (SEQ ID NO: 31) |
| Mut2, A2MUT2F: and | 5'TGTCGCGCCAAACCAGGGCGTG3' | (SEQ ID NO: 32) |
| A2MUT2R: | 5'CCATCACCAGGGCAAACC3'; | (SEQ ID NO: 33) |
| Mut3, A2MUT3F: and | 5'GTATCGTTCAGCAATTGGTCAGTG3' | (SEQ ID NO: 34) |
| A2MUT3R: | 5'ACG CGTATGGGTCTTTGGTTG3'; | (SEQ ID NO: 35) |
| Mut5, A2MUT5F: and | 5'ACGATTGCGGGTGATGC3' | (SEQ ID NO: 36) |
| A2MUT5R: | 5'CCTCTTGGCTGTAAGGCTGC3'. | (SEQ ID NO: 37) |

Each PCR product was cloned into pCR2.1, subcloned into pKnockout-G and introduced into DC3000 by triparental mating. After primary selection, plasmid insertion into the chromosome was verified by: i) PCR using T7 and 2-30 (5'ATGGCGGGTATCAATAGAGCGG3') (SEQ ID NO:38) primers, and ii) Southern blot analysis using PstI digested genomic DNA and the avrPtoB ORF as a probe.

Example 3

Immunoblotting

Detection of proteins expressed in the *Agrobacterium*-mediated transient assay was performed using standard immunoblotting procedures. Briefly, 48 hours after agroinfiltration, two 1 cm² leaf discs were ground in 400 μl of protein extraction buffer, composed of PBS amended with 1% Triton-x and plant protease inhibitor cocktail (Sigma, St. Louis, Mo.). Protein extracts were denatured and equal amounts of protein were electrophoresed on 12% polyacrylamide gels and transferred to PVDF membrane (Millipore Inmobilon P, Bedford, Mass.) by electroblotting according to the manufacturer's recommendation (Biorad, Hercules, Calif.). HA-tagged proteins were detected using rat anti-HA primary antibody (Boehringer-Mannheim, Indianapolis, Ind.), IRP-conjugated anti-Rat Ig secondary antibody (Amersham-Pharmacia, Piscataway, N.J.) and a chemiluminescent visualization kit (ECL Plus, Amersham-Pharmacia).

Example 4

Yeast Cell Death Assays

The *S. cerevisiae* strain EGY48 (MATa, ura3, his3, trp1, leA$_{op}$(x6)-LEU2) was obtained from Clontech (Palo Alto, Calif.) and the growth, transformation and expression of genes was performed essentially as described by Kampranis et al., "A novel plant glutathione S-transferase/peroxidase suppresses Bax lethality in yeast." *J. Biol Chem* 22: 29207-29216 (2000), which is hereby incorporated by reference in its entirety. The EGY48 cells were grown in YPD medium containing 1% yeast extract, 2% Difco peptone, and 2% glucose. AvrPtoB was cloned under the control of a galactose inducible plasmid in the high-copy yeast expression vector p423 (Mumberg et al., "Regulatable promoters of *Saccharomyces cerevisiae*: comparison of transcriptional activity and their use for heterologous expression." *Nucleic Acids Res,* 22: 5767-5768 (1994), which is hereby incorporated by reference in its entirety) and the plasmid was transformed into EGY48. Cells were grown in synthetic dropout (SD) medium with 2% glucose lacking histidine (SD/glu/-his) to select for the presence of the plasmid. EGY48 cells containing AvrPtoB were grown overnight in SD/glu/-his. The cells were pelleted, washed and resuspended in SD medium containing 2% galactose and 1% raffinose as carbon sources (SD/gal-raff/-his), to induce expression of the fusion protein from the GAL1 promoter. After 6 hr of induction, cells were diluted to 0.05 O.D.$_{600}$ and treated in one of the following ways. For chemical treatments, $H_2O_2$ or menadione were added at selected final concentrations in the medium and cultures were incubated at 30° C. with vigorous shaking for 6 hr. For heat stress, yeast cells were incubated at 37° C. for 30 min with vigorous shaking, then transferred to a water bath at 50° C. for 30 min and then returned to 30° C. with vigorous shaking for 6 hr. Following these treatments, viability was determined by plate counting. Treated and untreated cells were sampled and spread onto YPD medium with 2% agar, then incubated at 30° C. for 48 hr. The number of colony forming units (Cfu) from treated cells (both EGY48 and EGY48 carrying AvrPtoB) were compared to the Cfu of untreated cells. All experiments were repeated in triplicate.

Example 5

Tomato Infection and Measurement of Pathogen Growth in Leaves

Rio Grande (RG) tomato lines with the following genotypes were used in this study: RG-PtoR (Pto/Pto, Prf/Prf), RG-prf3 (Pto/Pto, prf3/prf3), RG-pto11 (pto11/pto11, Prf/Prf, and RG-ptoS (pto/pto, Prf/Prf). Bacterial growth measurements from tomato leaves were performed as described by Tang et al., "Overexpression of Pto activates defense responses and confers broad resistance." *Plant Cell,* 11: 15-30 (1999), which is hereby incorporated by reference in its entirety. Briefly, P. s. pv. tomato DC3000 strains were grown overnight in King's B (KB) medium with appropriate antibiotics. Cultures were washed twice with 10 mM $MgCl_2$ and resuspended in 10 mM $MgCl_2$. Washed cultures were prepared for inoculation by diluting cultures to $10^4$ cells/mL in 10 mM $MgCl_2$ and 0.04% Silwet L-77 (Osi, Danbury, Conn.). Six-week-old tomato plants were inoculated by vacuum infiltration and kept in a greenhouse during the course of infection. Bacterial growth was measured by grinding two 1 cm$^2$ leaf discs in 10 mM $MgCl_2$, and tissue samples were serially diluted, and plated on solid KB medium with antibiotics.

Example 6

AvrPtoB Broadly Suppresses PCD in *N. benthamiana* Leaves

The signaling components necessary for Pto-mediated PCD are conserved in the wild tobacco species *Nicotiana benthamiana*, because *Agrobacterium*-mediated transient co-expression of AvrPto and Pto in *N. benthamiana* leaves causes HR-related cell death, as shown in FIG. 1A (Scofield et al., "molecular basis of gene-for-gene specificity in bacterial speck disease of tomato." *Science* 274: 2063-2065 (1996); Sessa et al., "Signal recognition and transduction mediated by the tomato Pto kinase: a paradigm of innate immunity in plants." *Microbes Infect,* 2: 1591-1597 (2000), which are hereby incorporated by reference in their entirety). AvrPtoB, however, does not trigger cell death when co-expressed with Pto in *N. benthamiana*, as shown in FIG. 1A. This observation was unexpected because from yeast two-hybrid interactions and expression in tomato, it is known that AvrPtoB can interact with Pto and initiate PCD. It had been hypothesized that AvrPtoB, although likely binding to Pto in *N. benthamiana*, may also block downstream signaling events that lead to PCD.

Figure 1B:
Figure 1C:
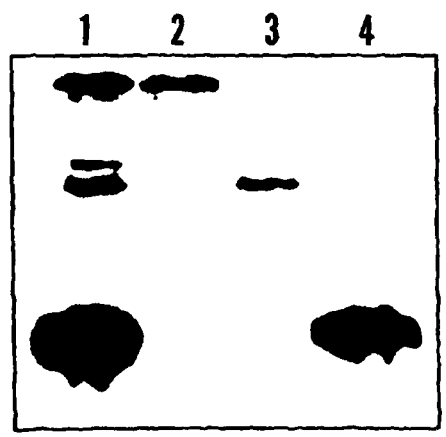

To test if AvrPtoB could suppress AvrPto/Pto-mediated PCD, AvrPto, AvrPtoB and Pto were co-expressed in *N. benthamiana* leaves and found that AvrPto/Pto-dependent cell death was suppressed, as shown in FIG. 1A and in FIG. 1B. Cell death suppression was stable and observed as long as two weeks after inoculation. Expression of the three proteins in plant leaves was verified by using HA epitope-tagged constructs of AvrPto, AvrPtoB, and Pto; all three proteins were detected together and separately by immunoblot, as shown in FIG. 1C. A possible explanation for the observed cell death suppression was that AvrPtoB out-competed AvrPto for interaction with the Pto kinase. To examine this possibility, AvrPtoB and Pto(Y207D) were co-expressed. Pto(Y207D) is a mutant kinase that, independent of effector recognition, initiates PCD (Rathjen et al., "Constitutively active Pto induces a Prf-dependent hypersensitive response in the absence of avrpto." *Embo J,* 18: 3232-3240 (1999), which is hereby incorporated by reference in its entirety). Expression of AvrPtoB suppressed Pto(Y207D)-initiated cell death, as shown in FIG. 1A. This observation suggests AvrPtoB acts downstream of Pto recognition when suppressing cell death.

The activity of AvrPtoB was further investigated by examining Avr9/Cf9-initiated PCD. The Avr9 avirulence protein is produced by the fungus *Cladosporium fulvum* and elicits immunity in tomato plants expressing the Cf9 R protein (Van Kan et al., "Cloning and characterization of cDNA of avirulence gene avr9 of the fungal pathogen *Cladosporium fulvum*, causal agent of tomato leaf mold." MPMI, 4: 52-59 (1991); Jones et al., "Isolation of the tomato Cf-9 gene for resistance to *Cladosporium fulvum* by transposon tagging." *Science,* 266: 789-793 (1994), which are hereby incorporated by reference in their entirety). Avr9 and Cf9 also cause HR-related cell death when they are transiently co-expressed in *N. benthamiana* (Van der Hoom et al., "Agroinfiltration is a versatile tool that facilitates comparative analyses of Avr9/Cf-9-induced and Avr4/Cf4-induced necrosis." *MIMI,* 13: 439-446 (2000), which is hereby incorporated by reference in its entirety). Cf9-dependent and Pto-dependent PCD differ in several ways. First, Pto requires the Prf gene to signal PCD whereas Cf9-dependent PCD does not require Prf. Also, in the transient assay, Cf9-initiated cell death is substantially delayed compared to Pto-initiated cell death. Co-expression of AvrPtoB with Avr9 and Cf9 inhibited Avr9/Cf9-dependent cell death in *N. benthamiana*, as shown in FIG. 1A. This finding suggests that AvrPtoB-mediated suppression of PCD acts on a target downstream of a point where these two R gene signaling pathways converge.

Given its surprisingly broad inhibitory activity, was examined to determine if AvrPtoB acts generally on the process of PCD in *N. benthamiana*. The mouse protein Bax is a member of the Bcl-2 family of pro-apoptotic proteins and initiates PCD by disrupting the mitochondrion and causing the release of cytochrome c and other pro-apoptotic factors (Jurgensmeier et al., "Bax directly induces release of cytochrome c from isolated mitochondria." *Proc Natl Acad Sci USA*, 95: 4997-5002 (1998), which is hereby incorporated by reference in its entirety). Expression of the Bax protein in plants has been found to initiate a rapid cell death response that closely resembles the HR (Kawai et al., "Mammalian Bax-induced plant cell death can be down-regulated by overexpression of Arabidopsis Bax Inhibitor-1 (AtBI-1)." *Proc Natl Acad Sci USA*, 98: 12295-12300 (2001); Lacomme et al., "Bax-induced cell death in tobacco is similar to the hypersensitive response." *Proc Natl Acad Sci USA*, 96: 7956-7961 (1999), which are hereby incorporated by reference in their entirety). In both plants and yeast, Bax-induced cell death is dependent on a C-terminal mitochondrion-targeting domain (Lacomme et al., "Bax-induced cell death in tobacco is similar to the hypersensitive response." *Proc Natl Acad Sci USA*, 96: 7956-7961 (1999), which is hereby incorporated by reference in its entirety), suggesting a common PCD-initiating mechanism across kingdoms. The mouse Bax protein was transiently expressed in *N. benthamiana* under control of a promoter that is inducible by the glucocorticoid hormone dexamethasone (Dex) (Aoyama et al., "A glucocorticoid-mediated transcriptional induction system in transgenic plants." *Plant Journal*, 11: 605-612 (1997), which is hereby incorporated by reference in its entirety). The Bax gene by itself or constitutive avrPtoB and inducible Bax genes were co-transformed into *N. benthamiana* leaves and Bax expression was induced 48 hours after agroinfiltration by spraying leaves daily with 30 µM Dex. After five days of Dex induction, cell death was observed in leaves expressing Bax alone, while cell death was not observed in leaves expressing Bax and AvrPtoB, as shown in FIG. 1A. The ability of AvrPtoB to broadly suppress PCD initiated by two distinct R proteins as well as the pro-apoptotic mouse protein Bax, suggests that AvrPtoB acts generally as an inhibitor of PCD in *N. benthamiana*.

Example 7

AvrPtoB Suppresses PCD in Yeast

Figure 2A:
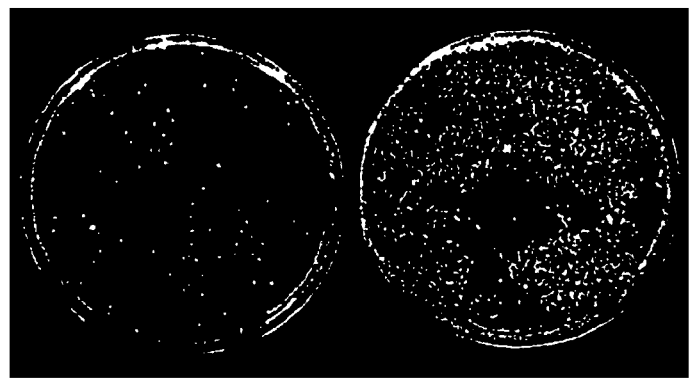
FIGS. 2A-B show AvrPtoB suppresses oxidative and heat stress-induced cell death in yeast.
Figure 2B:
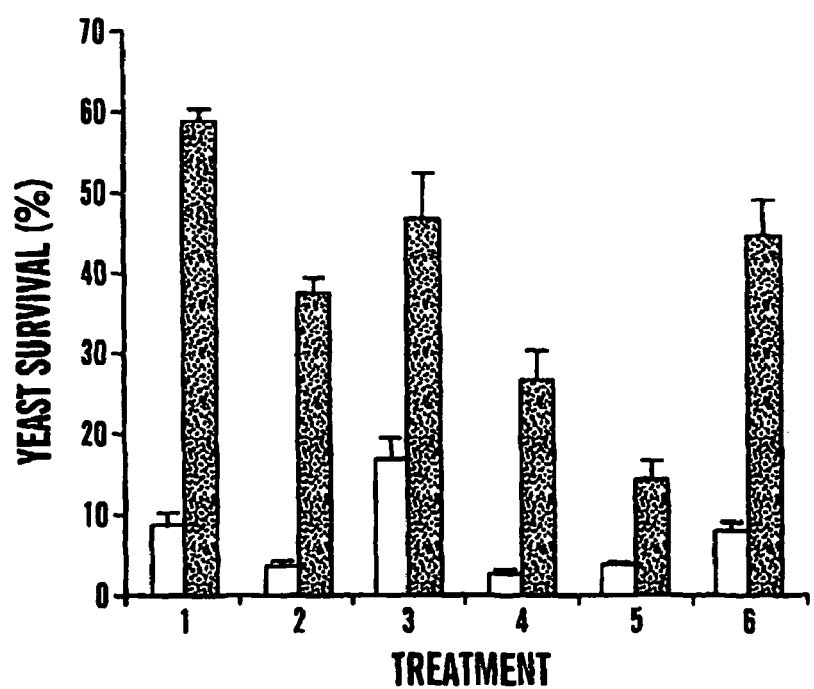

Since AvrPtoB broadly suppressed PCD in *N. benthamiana*, AvrPtoB was examined to determine if it may act on general components of eukaryotic cell death execution and perhaps AvrPtoB anti-PCD activity would be conserved in yeast. In *Saccharomyces cerevisiae*, PCD induced by oxidative stress or mammalian pro-apoptotic factors such as Bax, exhibits many of the hallmarks of metazoan apoptosis, including cytochrome c release, DNA fragmentation and chromatin condensation. As with mammalian apoptosis, oxidative stress is an important regulator of yeast PCD, and apoptotic responses can be induced by addition of low concentrations of hydrogen peroxide. AvrPtoB was expressed in the yeast strain EGY48 and yeast cells were treated with $H_2O_2$. Strikingly, it was observed that AvrPtoB protected yeast from PCD induced by 3 mM $H_2O_2$, as shown in FIGS. 2A and 2B, and 5 mM $H_2O_2$, as shown in FIG. 2B. It was also found that AvrPtoB protected yeast from cell death induced by menadione and heat shock, as shown in FIG. 2B. AvrPtoB, however, did not suppress Bax-induced cell death in yeast, suggesting that differences exist between Bax and AvrPtoB functions in *N. benthamiana* and yeast. The capacity of AvrPtoB to suppress PCD in plants and protect yeast from stress-induced PCD, clearly establishes AvrPtoB as a eukaryotic cell death inhibitor.

Example 8

AvrPtoB has a Modular Structure with Distinct Recognition and Anti-PCD Domains

To better understand the basis of AvrPtoB recognition and anti-PCD functions a series of AvrPtoB N— and C-terminal truncations was constructed. Each of the truncations discussed in this study leads to an observable phenotype when expressed in plant leaves, thus establishing protein expression in vivo. AvrPtoB was examined to determine if it suppresses PCD but is still recognized by Pto, such that an AvrPtoB mutant could be developed such that the anti-PCD function was eliminated while the Pto recognition domain was maintained. In such a case, AvrPtoB/Pto-mediated cell death might be observed in *N. benthamiana*.

Figures 3A, 3B:
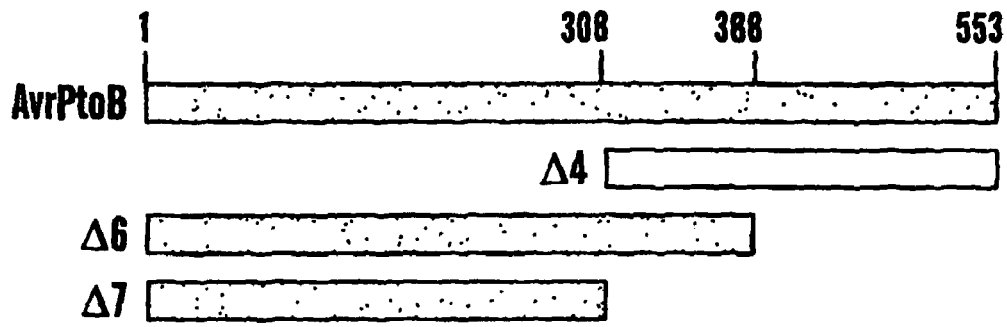
FIGS. 3A-B show structural analysis of AvrPtoB recognition and anti-PCD activity.

To map domains involved in AvrPtoB/Pto recognition, several deletion mutants were cloned as bait fusions and tested for interaction with a Pto prey fusion in a yeast two-hybrid system. Δ6 and Δ7 interacted strongly with Pto, as shown in FIG. 3A. Therefore, an AvrPtoB fragment from amino acids 1-308 of SEQ ID NO:2 is sufficient for strong interaction with Pto in yeast.

The Pto-interacting AvrPtoB truncations were expressed in tomato and *N. benthamiana* to test for Pto-dependent cell death. As predicted from the yeast two-hybrid interaction, Δ7 triggered cell death in a Pto- and Prf-dependent manner in tomato, as shown in FIG. 3B. In *N. benthlamiana*, co-expression of Δ7 and Pto also resulted in cell death, as shown in FIG. 4A. This gain of Δ7/Pto-initiated PCD demonstrates that the AvrPtoB N-terminus is sufficient for in vivo Pto-mediated recognition and suggests that the C-terminus is necessary for the observed PCD suppression. Significantly, intact AvrPtoB suppressed Δ7/Pto-initiated cell death when these three proteins were co-expressed, as shown in FIG. 4B. Given that i) AvrPtoB was shown to act downstream of recognition for PCD suppression, and ii) full length AvrPtoB dominantly suppresses Δ7/Pto-initiated PCD, it is proposed that the N-terminal domain of AvrPtoB is recognized by the Pto kinase in *N. benthamiana*, but that the C-terminus of the same protein suppresses PCD signaled by this recognition event.

The newly observed Δ7/Pto-initiated PCD suggested that anti-PCD activity may reside in the AvrPtoB C-terminus. Several N-terminal deletions were tested for anti-PCD activity in *N. benthamiana*. Δ4 was found to be capable of inhibiting cell death initiated by AvrPto/Pto, as shown in FIG. 4A, Pto(Y207D) and Avr9/Cf9 in *N. benthlamiaiza*. However, Δ4 PCD suppression was not as stable as full length AvrPtoB, often breaking down after seven days. Also, Δ4 did not suppress Bax-induced cell death, which is the most rapid and severe of the cell death phenotypes examined. The weaker anti-PCD function may be the result of altered localization, decreased protein stability or lower expression of the truncated form. Nevertheless, these data show that the C-terminus of AvrPtoB is sufficient for PCD inhibition. As such, recognition and anti-PCD functions could be separated into two non-overlapping AvrPtoB regions. Therefore, AvrPtoB has a modular structure with Pto-recognition in the N-terminal module and anti-PCD function in the C-terminal module.

Example 9

Truncated AvrPtoB Elicits a Novel Resistance Phenotype, Rsb

When testing Δ6 for recognition activity in tomato and *N. benthamiana*, it was unexpectedly discovered that this truncation triggered PCD in the absence of Pto. In tomato plants that have a mutant pto gene, RG-pto11 (Salmeron et al., "Tomato mutants altered in bacterial disease resistance provide evidence for a new locus controlling pathogen recognition." *Plant Cell*, 6: 511-520 (1994), which is hereby incorporated by reference in its entirety), expression of Δ6 initiated rapid cell death, as shown in FIG. 3B; however, in the absence of the Prf gene, Δ6 did not initiate cell death, as shown in FIG. 3B, indicating that Δ6-mediated cell death is not the result of cytotoxicity. This new tomato resistance phenotype has been designated Rsb (Resistance Suppressed by AvrPtoB C-terminus). Similarly, Δ6 initiated cell death when expressed by itself in *N. benthamiana*, as shown in FIG. 4A, demonstrating the conservation of the Rsb phenotype; Rsb-mediated cell death is also Prf-dependent in *N. benthamiana*. Interestingly, when Δ6 and Pto were co-expressed, a faster and more severe cell death phenotype was observed as compared to Δ6- or Δ7/Pto-initiated cell death, as shown in FIG. 4A and in FIG. 4B. This enhanced cell death phenotype may be indicative of multiple recognition events. Because Δ7 does not elicit Pto-independent cell death, a domain was mapped that triggers Rsb-mediated PCD between amino acids 308-388 of SEQ ID NO: 2.

Several explanations exist for the observed Δ6/Rsb-mediated PCD. One possibility is that the C-terminus of full length AvrPtoB physically hides the recognition domain, thus making it inaccessible to Rsb. Alternatively, fall length AvrPtoB may normally suppress Rsb-initiated PCD downstream of Rsb recognition. AvrPtoB and Δ6 were co-expressed in *N. benthamiana* and tomato pto null mutants and in both cases PCD was not observed, as shown in FIG. 4C, indicating that suppression of Rsb-dependent cell death occurs by an intermolecular mechanism. Moreover, intact AvrPtoB also suppressed the more severe Δ6/Pto-initiated PCD, as shown in FIG. 4B. Given the evidence that AvrPtoB can act downstream of recognition for PCD suppression, it was proposed that intact AvrPtoB is recognized by a determinant of the Rsb resistance phenotype in tomato and *N. benthamiana*, but that the C-terminal module normally suppresses subsequent downstream events leading to PCD.

Example 10

Figures 5A, 5B:
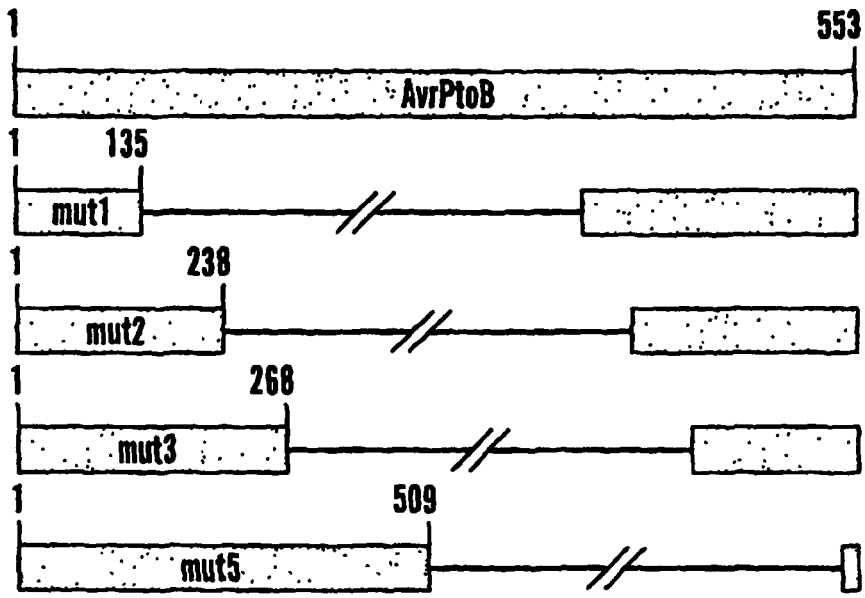
FIGS. 5A-B show P. s. pv. tomato DC3000 chromosomal mutants of avrPtoB and disease responses of inoculated tomato plants.

AvrPtoB is a Pathogenicity Factor that Induces Plant Susceptibility to P. s. pv. tomato DC3000 Infection The discovery of Rsb-mediated PCD presented an opportunity to examine the role of PCD suppression in DC3000 pathogenesis. Since wild type DC3000 causes disease in RG-pto11 plants, it was hypothesized that intact AvrPtoB normally inhibits Rsb-mediated immunity in RG-pto11 tomato plants. Therefore, plant immunity might be elicited by a DC3000 mutant expressing an AvrPtoB C-terminal truncation where the anti-PCD function was destroyed but Rsb recognition was maintained. In parallel to this study, a series of C-terminal AvrPtoB truncations on the DC3000 chromosome was constructed by means of recombination with a plasmid by a single crossover event, as shown in FIG. 5A. One of the mutants, DC3000::mut5, expressed an AvrPtoB fragment from amino acids 1-509, as shown in FIG. 5A. Like wild type DC3000, DC3000::mut5 triggered immunity on RG-PtoR plants and caused disease on RG-prf3 plants, as shown in FIG. 5B, in FIG. 6A and in FIG. 6B. However, like Δ6 in the transient assay, DC3000::mut5 triggered immunity when inoculated on RG-pto11 plants, as shown in FIG. 5B, in FIG. 6A and in FIG. 6B. Wild type and mutant DC3000 strains with several other AvrPtoB chromosomal truncations did not trigger immunity on RG-pto11, as shown in FIG. 5B, demonstrating that the observed immunity is likely the result of the Rsb phenotype discovered in the transient assay.

Figure 6A:
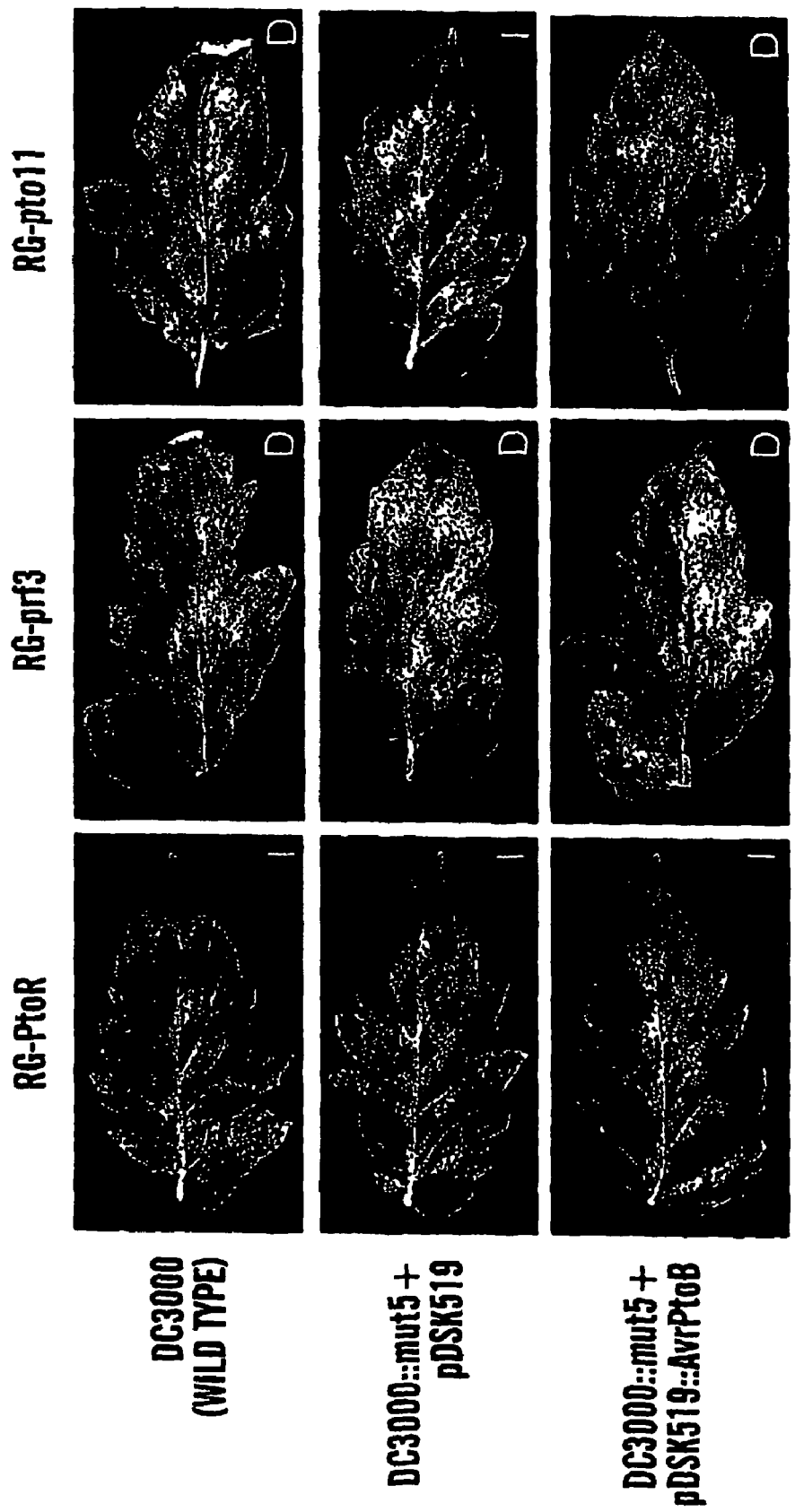
FIGS. 6A-B show AvrPtoB induces plant susceptibility to P. s. pv. tomato DC3000 infection.
Figure 6B:
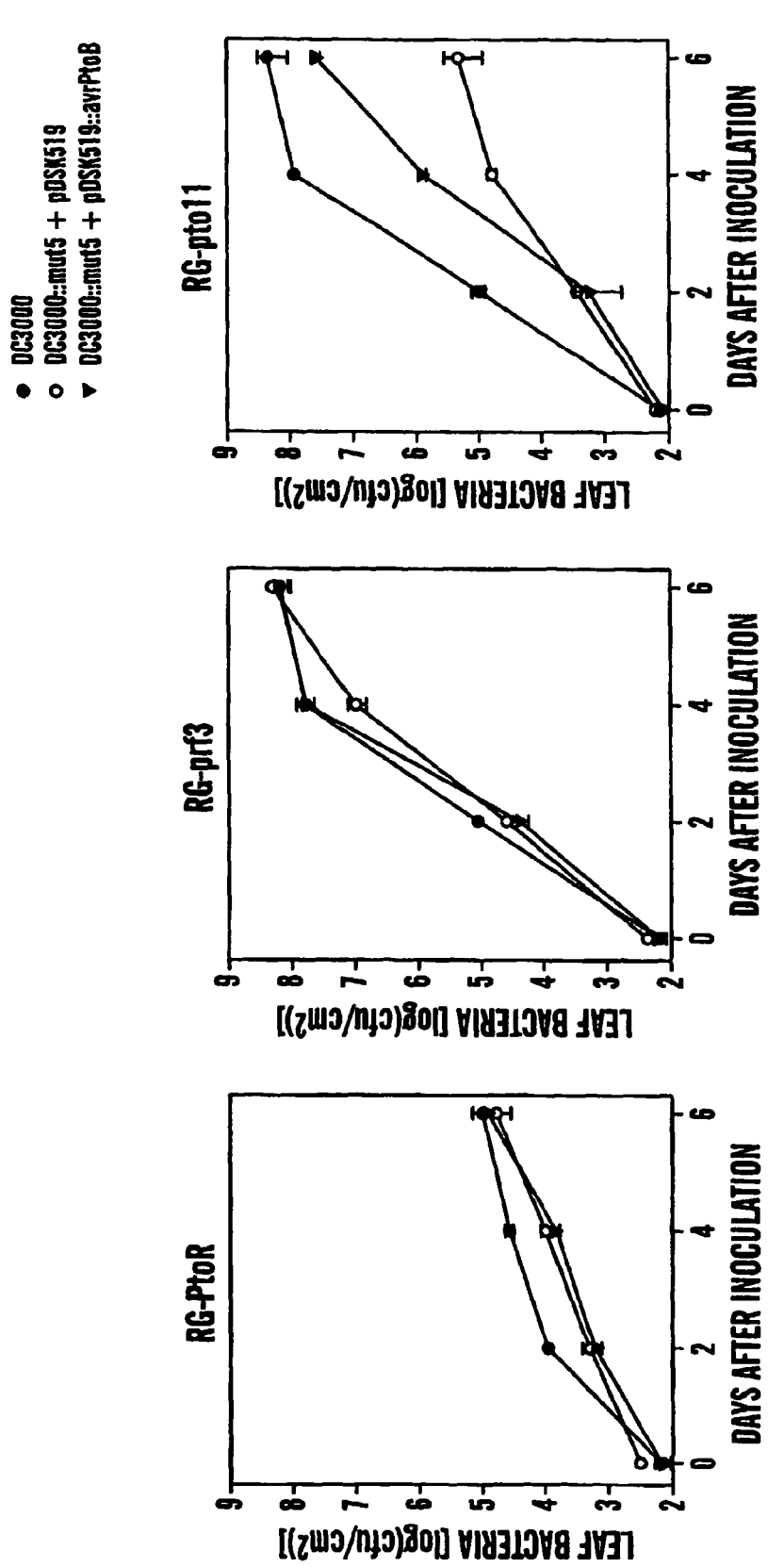

To confirm that AvrPtoB acted as a pathogenicity determinant, DC3000::mut5 was transformed with the pDSK519 broad host range plasmid (Keen et al., "Improved Broad-Host-Range Plasmids for DNA Cloning in Gram-Negative Bacteria," *Gene* 70:191-197 (1988), which is hereby incorporated by reference in its entirety) expressing full length AvrPtoB from its native promoter. Expression of intact AvrPtoB in trans enabled DC3000::mut5 to cause disease in RG-pto11, as shown in FIG. 6A and in FIG. 6B. The observed DC3000::mut5-pDSK519::AvrPtoB disease symptoms were less severe than wild type DC3000, with approximately ten-fold less growth and smaller specks on the leaves. These slightly reduced disease symptoms are consistent with reported observations in P. s. pv. *maculicola* that effectors are sometimes better expressed from the chromosome than from a plasmid (Guttman et al., "Functional analysis of the type III effectors AvrRpt2 and AvrRpm1 of *Pseudomonas syringae* with the use of a single-copy genomic integration system." *Mol Plant Microbe Interact*, 14: 145-155 (2001), which is hereby incorporated by reference in its entirety). Nevertheless, addition of AvrPtoB was sufficient to shift the DC3000::mut5/RG-pto11 interaction from immunity to disease, demonstrating that AvrPtoB is a pathogenicity factor and that the final 44 amino acids of AvrPtoB are necessary to inhibit Rsb-mediated immunity. Interestingly, at four days after inoculation, DC3000::mut5 grew approximately ten-fold less on diseased RG-prf3 plants and caused less severe disease symptoms, when compared to wild type or DC3000::mut5 expressing intact AvrPtoB in trans. This observation hints that intact AvrPtoB may also act quantitatively as a virulence factor, perhaps by suppressing cell death. Because immunity was triggered by DC3000::mut5 and disease was regained with AvrPtoB expression in trans, and taken together with the findings that AvrPtoB acts downstream of recognition to inhibit PCD, these data suggest that AvrPtoB induces plant susceptibility to bacterial infection by inhibiting host PCD. Therefore, it was proposed that effector-mediated inhibition of PCD is an important novel bacterial pathogenesis strategy. Moreover, these data suggest that PCD is a necessary component of HR-based immunity in plants.

The discovery of Rsb-mediated immunity was an unexpected but useful tool to explore the role of AvrPtoB in plant disease. Although the Rsb-phenotype remains mostly uncharacterized, several clues point towards the basis of this immune response. First, the response was shown to be Prf-dependent, indicating it is likely a classical gene-for-gene resistance response. Given the observed Δ6-initiated HR in RG-PtoR and RG-pto11, and the absence of Δ6-initiated HR in RG-prf3 tomato plants, it was possible that Prf was the Rsb determinant. To examine this possibility, Δ6 was expressed in RG-ptoS tomato plants and also inoculated DC3000::mut5 on RG-ptoS plants. RG-ptoS is a near isogenic line with RG-PtoR and differs mainly at the introgressed Pto region, where RG-ptoS and RG-PtoR have the *L. esculentum* and *L. pimpinellifolium* Pto haplotypes, respectively (Martin et al., "Map-based cloning of a protein kinase gene conferring disease resistance in tomato." *Science*, 262: 1432-1436 (1993), which is hereby incorporated by reference in its entirety). RG-ptoS has a functional Prf gene, since ectopic expression of Pto in RG-ptoS plants leads to AvrPto-dependent cell death. Transient expression of Δ6 in RG-ptoS did not lead to HR, as shown in FIG. 3B and DC3000::mut5 caused disease in RG-ptoS, as shown in FIG. 5B. Together, these finding exclude Prf as the sole determinant of the Rsb phenotype and strongly indicate that the Rsb phenotype is governed by another gene (or genes) residing in the *L. pimpinellifolium* Pto region.

Example 11

*Pseudonomnas* type III Effector AvrPtoB Induces Plant Disease Susceptibility by Inhibition of Host Programmed Cell Death It has been shown that the P. s. pv. tomato DC3000 type III effector AvrPtoB is a pathogenicity factor that can suppress HR-based plant immunity. By means of transient expression of individual proteins, inhibition of plant PCD was identified as the pathogenic mechanism of action of AvrPtoB. Given the presumed importance of PCD in HR-based plant defense, it is logical that a type III effector would target this process to induce host susceptibility. It is possible that other type III effectors that have been implicated in allowing plant pathogens to evade HR-based resistance (e.g. VirPphA, AvrPphC, and AvrPphF) also function using a similar mechanism. Previous to this work, several hypotheses had been proposed for the molecular basis of effector-mediated evasion of the HR. The data present a conceptual stride forward in understanding the role of type III effectors in facilitating bacterial pathogenicity, and offer several new and interesting insights into the molecular basis of plant susceptibility and immunity.

AvrPtoB suppresses PCD in *N. benthamiana* triggered by two distinct R proteins and the pro-apoptotic mouse protein Bax and also suppresses cell death in yeast triggered by hydrogen peroxide, menadione and heat shock. Given its broad anti-PCD activity, AvrPtoB likely acts on a target far downstream in the process of HR and PCD signaling. AvrPtoB may act to suppress PCD by directly interfering with a host component necessary for PCD or by altering host gene expression or cell physiology to stimulate a PCD suppressive cellular environment. The molecular basis of plant PCD is still poorly characterized and few components that are known to control metazoan PCD have been characterized for plant PCD. Suppressors of plant PCD, however, have been identified, including pharmacological agents such as caspase inhibitors (del Pozo et al., "Caspases and programmed cell death in the hypersensitive response of plants to pathogens." *Curr Biol*, 8: 1129-1132 (1998); Lam et al., "Caspase-like protease involvement in-the control of plant cell death." *Plant Mol Biol*, 44: 417-428 (2000), which are hereby incorporated by reference in their entirety) and in *Arabidopsis*, the At-BI1 protein, that was identified as a general suppressor of Bax triggered PCD in both yeast and *Arabidopsis* (Kawai et al., "Evolutionarily conserved plant homologue of the Bax inhibitor-1 (BI-1) gene capable of suppressing Bax-induced cell death in yeast." *FEBS Lett*, 464: 143-147 (1999); Kawai et al., "Mammalian Bax-induced plant cell death can be down-regulated by overexpression of Arabidopsis Bax Inhibitor-1 (AtBI-1)." *Proc Natl Acad Sci USA*, 98: 12295-12300 (2001), which are hereby incorporated by reference in their entirety). These observations indicate that, although still uncharacterized, targets for PCD inhibition exist in plants. It will be interesting to use AvrPtoB as a tool to investigate PCD in plants and yeast and possibly in other eukaryotic systems, such as insect and mammalian cells. Yeast can be a powerful tool to study the virulence activity of bacterial effector proteins of mammalian pathogens. Given that little is known about plant PCD, a yeast model should accelerate further study of the genetics, cell biology and biochemistry of AvrPtoB cell death inhibition in both yeast and plants.

Plant immunity is a multifaceted phenomenon associated with an array of physiological responses including defense gene induction, phytoalexin production, reactive oxygen species formation and HR-related PCD. Although PCD is widely believed to play a role in limiting pathogen growth, the importance of PCD in plant immunity is the subject of debate, and gene-for-gene based immunity without HR-like PCD has been proposed (Clough et al., "The *Arabidopsis* dnd1 "defense, no death" gene encodes a mutated cyclic nucleotide-gated ion channel." *Proc Natl Acad Sci USA*, 97: 9323-9328 (2000); Yu et al., "Gene-for-gene disease resistance without the hypersensitive response in Arabidopsis dnd1 mutant." *Proc Natl Acad Sci USA*, 95: 7819-7824 (1998), which are hereby incorporated by reference in their entirety). The finding that AvrPtoB functions to suppress both HR-based immunity and PCD strongly suggests that PCD is an essential and perhaps key component of HR-based immunity to P. s. pv. tomato DC3000. Further study, however, of how AvrPtoB affects plant physiology and gene expression will be necessary to explore this hypothesis.

Suppression of PCD by a bacterial type III effector is a novel pathogenesis strategy. Modulation of host PCD, however, is clearly important for bacterial pathogenesis as it has been observed in numerous model systems. For example, induction of PCD by type III effectors has been associated with disease formation of animal pathogens, including *Yersinia* (Juris et al., "Yersinia effectors target mammalian signalling pathways." *Cell Microbiol*, 4: 201-211 (2002), which is hereby incorporated by reference in its entirety) and *Salmonella* (Knodler et al., "*Salmonella* and apoptosis: to live or let die?" *Microbes Infect*, 3: 1321-1326 (2001), which is hereby incorporated by reference in its entirety). Although not experimentally associated with type III effectors, inhibition of PCD has been described for animal pathogens including *Chlamydia* (Geng et al., "Chlamydia pneumoniae inhibits apoptosis in human peripheral blood mononuclear cells through induction of IL-10." *J Immunol*, 164: 5522-5529 (2000), which is hereby incorporated by reference in its entirety), *Neisseria* (Massari et al., "*Neisseria meningitidis* porin PorB interacts with mitochondria and protects cells from apoptosis." *Proc Natl Acad Sci USA*, 97: 9070-9075 (2000), which is hereby incorporated by reference in its entirety) and *Rickettsia* (Clifton et al., "NF-kappa B-dependent inhibition of apoptosis is essential for host cellsurvival during Rickettsia rickettsii infection." *Proc Natl Acad Sci USA*, 95: 4646-4651 (1998), which is hereby incorporated by reference in its entirety). Interestingly, *Chlamydia* has a TTSS and it is therefore possible that effector-mediated PCD suppression is a common bacterial pathogenesis strategy in both plant and animal disease.

Plant pathogen effectors were initially isolated as avirulence proteins based on their ability to elicit the HR and plant immunity. Given the strong selective pressure for a pathogen to lose a factor that triggers immunity, it is widely assumed that type III effectors must also play an important role in disease formation. This assumption is supported by the observation that the TTSS is required for disease formation and experimental evidence that effector proteins can improve pathogen growth on plants (Chang et al., "avrPto enhances growth and necrosis caused by *Pseudomonas syringae* pv. tomato in tomato lines lacking either Pto or Prf." *Mol Plant Microbe Interact*, 13: 568-571 (2000); Chen et al., "The *Pseudomonas syringae* avrRpt2 gene product promotes pathogen virulence from inside plant cells." *Mol Plant Microbe Interact*, 13: 1312-1321 (2000); Shan et al., "A cluster of mutations disrupt the avirulence but not the virulence function of AvrPto." *MPMI*, 13: 592-598 (2000), which are hereby incorporated by reference in their entirety). One of the longstanding questions of plant pathogen effector research has been if avirulence and virulence functions of an effector could be physically separated. Distinct N— and C-terminal domains of AvrPtoB have been identified that are sufficient for recognition and anti-PCD activity, respectively. The modular nature of AvrPtoB raises several important questions about AvrPtoB evolution and function. For example, given its modular nature, it is possible that AvrPtoB evolved from a fusion of two ancestral proteins. Supporting this observation, truncated homologs of AvrPtoB that only contain the N-terminal module have been identified in Nature, including P. s. pv. *maculicola* effectors HopPmaL and HopPmaN (Guttman et al., "A functional screen for the type III (Hrp) secretome of the plant pathogen *Pseudomonas syringae*." *Science*, 295: 1722-1726 (2002), which is hereby incorporated by reference in its entirety), and the P. s. pv. tomato JL1065 AvrPtoB homolog, as shown in FIGS. 7A-E. Intriguingly, the conservation of the recognized N-terminal domain by itself or with the anti-PCD domain, suggests that this domain may also serve a function in virulence, otherwise it would not be maintained in the pathogen. In fact, preliminary evidence using the DC3000:mut mutants described in this paper, suggests that the recognized N-terminal domain of AvrPtoB does play a role in P. s. pv. tomato DC3000 virulence.

Figure 8:
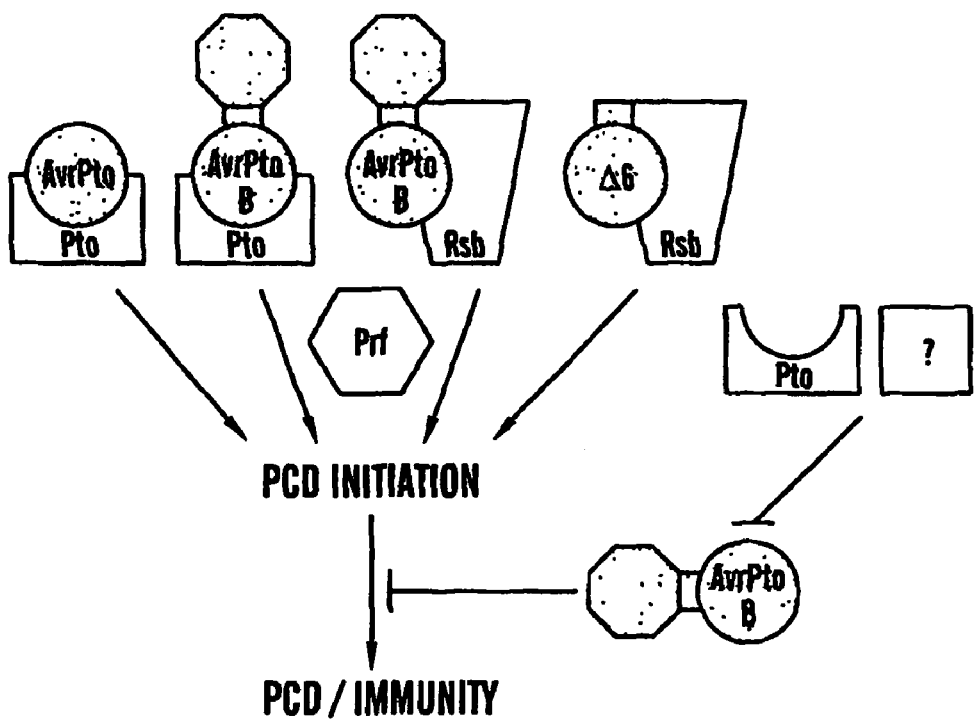
FIG. 8 shows a model for AvrPtoB recognition and PCD inhibition in tomato. The modular structure of AvrPtoB is depicted with the Pto-recognized N-terminal module shown as a brown circle, the anti-PCD C-terminal module shown as a red octagon, and the region recognized by Rsb shown as a blue connecting line. The black box represents an unknown factor predicted to act with Pto to suppress AvrPtoB anti-PCD function. Rsb-mediated cell death and immunity only occurs in the presence of the Δ6 truncation and the absence of Pto and intact AvrPtoB. Note: the gene(s) controlling the Rsb phenotype has not been identified; therefore, Rsb is presented in this model as a hypothetical R protein.

It is noteworthy that AvrPtoB inhibits Pto-initiated PCD in *N. benthamiana* but not in tomato. This observation reveals that tomato has evolved a novel resistance response that acts to suppress AvrPtoB anti-PCD activity. Tomato, however, is not completely recalcitrant to AvrPtoB PCD inhibition, because Rsb-mediated PCD and immunity can be suppressed in RG-pto11. Because RG-PtoR and RG-pto11 plants are isogenic, except at pto, this implicates the Pto R protein as a candidate factor that acts to suppress anti-PCD activity, perhaps by binding and sequestering AvrPtoB. However, Pto alone is not sufficient, since AvrPtoB can suppress Pto-dependent PCD in *N. benthlamiania*. Therefore, in tomato, it is predicted that other factors act in conjunction with Pto to inhibit AvrPtoB anti-PCD function, as shown in FIG. 8. Overall, the model suggests that a chimeric effector can function at multiple points in a plant immune response and can either elicit or suppress plant immunity depending on the host genetic background. Such host-specific mechanisms are likely widespread, given observations from the P. s. pv. *phaseolicola*-bean pathosystem, where the effector AvrPphF inhibits HR-based resistance in bean cv. Tendergreen but triggers immunity in bean cv. Canadian Wonder (Tsiamis et al., "Cultivar-specific avirulence and virulence functions assigned to avrPphF in *Pseudomonas syringae* pv. *phaseolicola*, the cause of bean halo-blight disease." *Embo J*, 19: 3204-3214 (2000), which is hereby incorporated by reference in its entirety). Isolating factors that suppress the anti-PCD activity of AvrPtoB may reveal new signaling components of plant disease resistance and offer novel strategies for crop protection.

It was reported previously that the AvrPtoB GINP motif, from amino acids 325-328, was involved in AvrPtoB/Pto-mediated recognition (Kim et al., "Two distinct pseudomonas effector proteins interact with the pto kinase and activate plant immunity." *Cell*, 109: 589-598 (2002), which is hereby incorporated by reference in its entirety). This result was based on the observations that: i) point mutations in the GINP motif weakened the interaction of AvrPtoB with Pto in a yeast two-hybrid system; ii) P.s. pv. tomato PT11 expressing AvrPtoB with a mutation in the GINP motif did not elicit an HR or immunity on Pto expressing tomato plants; and iii) the GINP motif is conserved in the AvrPto effector and is required for AvrPto/Pto interaction (Shan et al., "A Cluster of Mutations Disrupt the Avirulence But Not the Virulence Function of AvrPto," *MPMI* 13:592-598 (2000), which is hereby incorporated by reference in its entirety). In this study, however, it was found that Δ7, an AvrPtoB truncation that does not contain the GINP motif, still interacted strongly with Pto and triggered Pto-dependent PCD in plants. These seemingly contradictory data may offer insight into structural aspects of AvrPtoB. Since an AvrPtoB truncation missing the GINP motif is sufficient for Pto recognition, but intact AvrPtoB requires the GINP motif for Pto recognition, it is suspected that the GINP motif plays a key role in maintaining the structure of full length AvrPtoB. Interestingly, when mutations are introduced into the AvrPto GINP motif, the virulence function of AvrPto is maintained, indicating that GINP mutations do not necessarily destabilize the global structure of an effector. Rather, the GINP motif may act to "present" a contact surface to the Pto kinase. Data reported in this paper indicate that the AvrPtoB/Pto contact surface resides between amino acids 1-308 of SEQ ID NO: 2.

The unusually broad conservation of the AvrPtoB type III effector in many plant pathogens suggests AvrPtoB-mediated suppression of PCD and immunity plays an important role in bacterial pathogenesis. Certainly, AvrPtoB will be a useful tool to dissect the molecular basis of plant R protein PCD signaling, which presently is poorly understood. AvrPtoB anti-PCD activity may also have biotechnological applications; for example, AvrPtoB may allow efficient transgenic expression of proteins that otherwise elicit host PCD or may function to alter PCD-dependent plant developmental processes, such as senescence. Further study of AvrPtoB structure and function should lead to new insights into the basis of effector-mediated PCD inhibition and host mechanisms that guard against PCD inhibition.

Example 12

Bacterial Strains

The *E. coli* strains DH5α and DH10B (Gibco-BRL, Grand Island, N.Y.), *Agrobacterium tumefaciens* strains EH1105 and GV2260, and *P. s. tomato* strains were used for plasmid maintenance, transgene delivery, or infection assays, respectively. Plasmids used were pBluescript SK(−) (Stratagene, La Jolla, Calif.), pCR2.1 (Invitrogen, Carlsbad, Calif.), and pDSK519 (Keen et al., "Improved broad-host-range plasmids for DNA cloning in Gram-negative bacteria." *Gene*, 70: 191-197 (1988), which is hereby incorporated by reference in its entirety). Isolates and transconjugants of *P. s. tomato* were grown on King's medium B (KB) agar at 30° C. and *E. coli* strains on LB agar or in LB broth at 37° C.

Example 13

Yeast Two-Hybrid Library Development and Screening

Plasmids (pEG202, pJG4-5; pSH18-34, pRFHM-1, and pJK101) and yeast strain EGY48 (ura3, his3, trp1, LexAop-LEU2) were provided by R. Brent (Mass. General Hospital, Boston, Mass.), and basic procedures for the yeast two-hybrid system are described previously (Zhou et al., "The tomato gene Pti1 encodes a serine/threonine kinase that is phosphorylated by Pto and is involved in the hypersensitive response." *Cell* 83: 925-935 (1995), which is hereby incorporated by reference in its entirety). The *Pseudomonas* prey library was generated in a modified vector series based on pJG4-5. Three sets of sense/antisense oligonucleotides containing a unique ClaI site and based on the EcoRI and XhoI polylinker fragment of pBluescript SK(–) were created:

(1) 5'-GAATTCGATATCAAGCTrATCGATAC-CGTCGACCTCGAG-3' (SEQ ID NO:39);

(2) 5'-GAATTCgaattggGATATCAAGCTTATC-GATACCGTCGACCTCGAG-3' (SEQ ID NO:40); and (3) 5'-GAATTCgaattGATATCAAGCTTATC-GATACCGTCGACCTCGAG-3' (SEQ ID NO:41).

Oligonucleotides (2) and (3) contained the nucleotides shown in bold lower case to produce two additional reading frames. Complementing oligos were annealed and the fragments introduced into pJG4-5 using the EcoRI and XhoI restriction enzyme sites. The resulting plasmids, pJG4-5/Y0, pJG4-5/Y1, and pJG4-5/Y2, contain a unique ClaI site for cloning and each has a different reading frame.

Insert DNA for the prey library was prepared by partial digestion of *P. s. tomato* DC3000 genomic DNA with the enzymes AciI, MspI, HinPlI, or TaqI. Ten μg of each digest was size fractionated on a 0.8% agarose gel and fragments of 500 to 3000 bp were recovered. The DNAs were used in twelve ligation reactions (three vectors x four enzyme digests). Each ligation was transformed into ultracompetent *E. coli* strain DH10B and yielded >$10^8$ transformants. An equal number of transformants derived from each of the twelve libraries were pooled, grown in LB for 3 hour at 37° C., harvested by centrifugation, and DNA was extracted. The pooled DNA was transformed into *Saccharomyces cerevisiae* strain EGY48, which contained a LexA-Pto bait construct and the lacZ reporter plasmid pSH18-34 (Zhou et al., "The tomato gene Pti1 encodes a serine/threonine kinase that is phosphorylated by Pto and is involved in the hypersensitive response." *Cell* 83: 925-935 (1995), which is hereby incorporated by reference in its entirety). Approximately >$10^7$ transformants grew on glucose medium lacking uracil, histidine, and typtophan, and colonies were recovered in TE buffer containing 50% glycerol and stored at –80° C. Approximately 5×$10^7$ yeast cells were plated on 10-cm plates containing galactose agar medium lacking uracil, histidine, tryptophan, and leucine. 2,500 colonies, which appeared within 5 days, were collected, and assays on selective medium containing X-gal were performed. 180 candidates that were either strongly, moderately, or weakly blue on X-gal plates were chosen for plasmid rescue and further analysis.

Example 14

Constructs For Expression of AvrPtoB in *Pseudomonas* or Plant Cells

A cosmid library of DC3000 from Alan Collmer (Cornell Univ.) and screened using a AvrPtoB probe. A clone, pDC101, carrying a 37-kb insert was identified and a 6.0-kb PstI fragment was found to have the entire AvrPtoB open reading frame and putative Hrp-box. A 2.1-kb fragment from this region was using primer pair (avrPto2-14: 5'-CGGAG-GCGAACAGCCGAGCAG-3' (SEQ ID NO:42); avrPto2-3: 5'-GCAATTCGAAGTGGCAGTGA-3' (SEQ ID NO:43)) and cloned into pCR2.1 and then into the broad host range vector pDSK519, creating pDSK519::avrPtoB. All avrPtoB constructs were verified by sequencing. Triparental mating was used to mobilize pDSK519::avrPtoB DNA from *E. coli* DH5α into *P. s. tomato* strains. For expression in plant cells, primer pair avrpto2-12 (5'-TTATGCTTTATTGGTATTTT-TAGAGG-3') (SEQ ID NO:44) and avrpto2-3, or avrpto2-15- (5'-ATGGCGGGTATCAATAGAGC-3') (SEQ ID NO:45) and avrpto2-3 were used to amplify just the avrPtoB coding region. The sequences obtained were subcloned downstream of the CaMV 35S promoter in the vector pBTEX (Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety) and this construct was used for transient expression in plant leaves (see below). Site-directed mutagenesis of the avrPtoB sequence was performed in plasmid pJG4-5 or in pBTEX using the Quickchange kit from Stratagene (La Jolla, Calif.). The desired mutations were confirmed by sequencing.

Example 15

Determination of Disease Symptoms on Plant Leaves and Bacterial Populations in Liquid Culture Tomato (*Lycopersicon esculentum*) plants of Rio Grande-PtoS (RG-PtoS; pto/pto, Prf/Prf), Rio Grande-PtoR (RG-PtoR; Pto/Pto, Prf/Prf), and the mutants RG-prf-3 (Pto/Pto, prf/prf), and RG-pto11 (pto/pto, Prf/Prf) were grown in a greenhouse (24° C., 14 hr day). Tomato leaves on 7- or 8-week-old plants were vacuum-infiltrated with *P. s. tomato* bacterial suspensions of $10^4$ or $10^7$ colony-forming units per milliliter (cfu/mL). In low-inoculum level experiments, symptoms of bacterial speck disease developed over a 3 to 6 day period after inoculation. In high-inoculum level experiments, the HR occurred within 30 hr. Bacterial growth in KB liquid medium was determined by monitoring optical density at 600 nm and by plating serial dilutions of bacteria.

Example 16

*Agrobacterium*-Mediated Transient Expression in Plant Leaves

AvrPtoB expression constructs in pBTEX were introduced by electroporation into *Agrobacterium tumefaciens* strain GV2260 for tomato. *Agrobacterium* for inoculation was grown in LB medium overnight and diluted into induction medium (50 mM MES pH5.6, 0.5% (w/v) glucose, 1.7 mM NaH₂PO₄, 20 mM NH4Cl, 1.2 mM MgSO₄, 2 mM KCl, 17

μM FeSO$_4$, 70 μM CaCl$_2$ and 200 μM acetosyringone) to an OD$_{600}$=0.03. Bacterial suspensions were injected with a needle-less syringe into leaves of 7- to 8-week-old tomato plants. Inoculated tomato plants were kept in constant low light in the laboratory and *N. bentatamiana* was maintained in the greenhouse.

Example 17

Identification of *Pseudomoitas* Proteins that Interact with the Pto Kinase

To identify potential effectors from *P. s. tomato* DC3000 that interact with the Pto kinase a yeast two-hybrid screen was performed by using the tomato Pto kinase as the bait and a pool of DC3000 prey libraries. Based on the DNA sequences, ten classes of bacterial genes were identified in this screen, as shown in Table 2 below.

TABLE 2

Pto-interacting Proteins from *Pseudomonas syringae* pv. tomato DC3000

| Clone | Number retrieved | GenBank Match | Organism | E-value |
|---|---|---|---|---|
| PtiDC1 | 8 | VirPphA (AF141883) | *Pseudomonas syringae* pv. *phaseolicola* | e-140 |
| PtiDC2 | 13 | Dihydrofolate reductase (gi:150520) | *Salmonella typhimurium* | 3e-28 |
| PtiDC3 | 6 | No matching sequence | | |
| PtiDC4 | 5 | Inducible catalase (gi:1778585) | *Pseudomonas putida* | 3e-66 |
| PtiDC5 | 5 | Protein-L-isoaspartate O-methyltransferase (gi:2120644) | *Pseudomonas aeruginosa* | 3e-28 |
| PtiDC6 | 4 | Alginate lyase (AB018795) | *Halomonas marina* | 3e-58 |
| PtiDC7 | 4 | nhaR transcriptional activator (prf: 1817175B) | *Salmonella enteritidis* | 3e-13 |
| PtiDC8 | 4 | Ribosomal protein L11 methyltransferase (gi:1075231) | *Haemophilus influenzae* | 3e-25 |
| PtiDC9 | 3 | Chromosome initiation inhibitor (gi:1519235) | *Aeromonas salmonicida* | 2e-10 |
| PtiDC10 | 2 | Putative transposase (gi:2996223) | *Yersinia pestis* | 3e-10 |

Additional proteins that were retrieved from the yeast two-hybrid screen of the DC3000 genomic library using Pto as the bait.

Figure 9A:
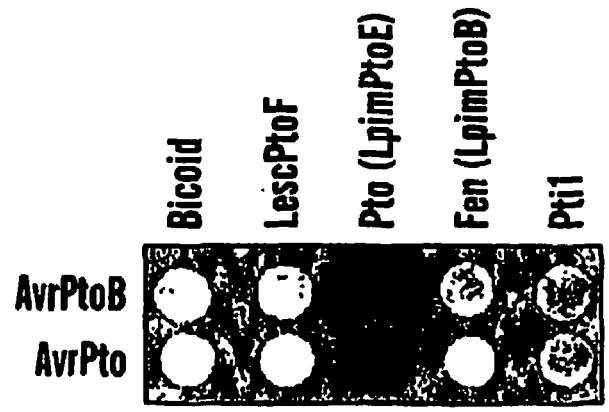

For unknown reasons, AvrPto was not recovered. One Pto-interacting class, PtiDC1, which contained eight clones, shared sequence similarity with a previously described virulence-related protein (see below) and is the focus of this paper. The eight PtiDC1 clones-did not auto-activate the reporter genes and re-transformation of them into the yeast expressing the Pto bait allowed growth on Leu- medium and cleavage of X-gal, as shown in FIG. 9A. Thus, the PtiDC1 clones encode a protein that interacts with Pto kinase in the yeast two-hybrid system.

Example 18

PtiDC1 Sequence is Similar to virPphA from *P. s. phaseolicola*

The nucleotide sequences were determined for the eight PtiDC1 clones and revealed they carried inserts truncated at three distinct 5' ends but were otherwise identical, as shown in FIG. 9B. Comparison of the nucleotide sequences of the PtiDC1 inserts to current databases showed similarity to the effector gene virPphA (GenBank No. AF141883) from *P. s. phaseolicola* (Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*, 96: 10875-10880 (1999), which is hereby incorporated by reference in its entirety). The gene was designated avrPtoB because the initial phenotype associated with the PtiDC1 sequence was avirulence (see below), and because this designation denoted its functional similarity with avrPto (i.e. avrPto, originally isolated from *P. s. tomato* strain JL1065, is formally avrPtoA$_{JL1065}$).

A cosmid was recovered from a DC3000 library by using a PtiDC1 probe and a 6.0 kb PstI fragment containing avrPtoB was subcloned and sequenced. The sequence revealed an open reading frame (ORF) spanning 1,659 bp, as shown in FIG. 9B (GenBank Acc. No. AY074795) (SEQ ID NO:2) with 52% nucleotide identity to the virPphA gene. A putative Hrp box (GGAACT-N$_{16}$-CCAC) (SEQ ID NO:46) is located 85 nucleotides upstream of the predicted AUG initiation codon and conforms closely to a consensus Hrp box recently derived from a large set of effectors from DC3000 (Fouts, et al., "Genomewide identification of *Pseudomonas syringae* pv. tomato DC3000 promoters controlled by the HrpL alternative sigma factor." *Proc Natl Acad Sci USA*, 99: 2275-2280 (2002), which is hereby incorporated by reference in its entirety). In accordance with this observation it was found that avrPtoB gene expression is induced in apoplast-mimicking medium and in planta in a hrp-dependent fashion.

The avrPtoB ORF produces a predicted protein of 553 amino acids with a molecular mass of 59 kDa. Putative amino acid sequence of AvrPtoB is 52% identical to VirPphA (BLASTP e value=e−140), as shown in FIG. 9C. The truncation points in the PtiDC1 clones, as shown in FIG. 9B, were found to remove the first 70, 112, or 121 amino acids of the AvrPtoB open reading frame. Database searches detected no sequence similarity between AvrPtoB and AvrPto. In addition, unlike AvrPto, the AvrPtoB protein has no myristylation motif immediately following the initiation methionine (Nimchuk et al., "Eukaryotic fatty acylation drives plasma membrane targeting and enhances function of several type III effector proteins from *Pseudonmonas syringae*." *Cell*. 101: 353-363 (2000); Shan et al., "The *Pseudomonas* AvrPto protein is differentially recognized by tomato and tobacco and is localized to the plant plasma membrane." *Plant Cell* 12: 2323-2337 (2000), which are hereby incorporated by reference in their entirety). However, pattern searching with PIR (Protein Information Resource) detected a possible myristylation site near the N-terminus (i.e. MAGINRAG (SEQ ID NO: 47); consensus motif is G-{not EDRKHPFYW}-x(2)-[STAGCN]-{not P}) (SEQ ID NO: 48) and 10 myristylation motifs within the protein.

Example 19

Interaction Specificity of AvrPtoB Protein for the Pto Kinase

Interaction specificity between AvrPto and Pto has been characterized extensively (Scofield et al., "Molecular basis of gene-for-gene specificity in bacterial speck disease of tomato." *Science* 274: 2063-2065 (1996); Tang et al., "The avirulence protein AvrPto physically interacts with the Pto kinase." *Science* 274: 2060-2063 (1996), Frederick et al., "Recognition specificity for the bacterial avirulence protein AvrPto is determined by Thr-204 in the activation loop of the tomato Pto kinase." *Molecular Cell.* 2: 241-245 (1998), which are hereby incorporated by reference in their entirety). To initially compare the Pto-interaction specificity of AvrPtoB with AvrPto, the AvrPtoB prey PtiDC1Δ70 with several bait plasmids expressing kinases closely related to Pto were introduced into the yeast two-hybrid system, as shown in FIG. 9A. AvrPtoB did not interact with the Fen kinase (Martin et al., "A member of tomato Pto gene family confers sensitivity to fenthion resulting in rapid cell death." *Plant Cell* 6: 1543-1552 (1994), which is hereby incorporated by reference in its entirety), the Pti1 kinase (Zhou et al., "The tomato gene Pti1 encodes a serine/threonine kinase that is phosphorylated by Pto and is involved in the hypersensitive response." *Cell* 83: 925-935 (1995), which is hereby incorporated by reference in its entirety), or the LescPtoF kinase (Jia et al., "Alleles of Pto and Fen occur in bacterial speck-susceptible and fenthion-insensitive tomato cultivars and encode active protein kinase." *Plant Cell* 9: 61-73 (1997); Riely et al., "Ancient origin of pathogen recognition specificity conferred by the tomato disease resistance gene Pto." *Proc. Natl. Acad. Sci. USA* 98: 2059-2064 (2001), which are hereby incorporated by reference in their entirety).

Figure 10A:
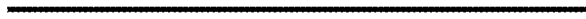
FIGS. 10A-C show interaction of AvrPtoB and AvrPto with the same variant forms of the Pto kinase.
Figure 10B:
Figure 10C:

Next, a series of chimeric Pto-Fen proteins and Pto mutants were examined that were used previously to show that Thr-204 in the Pto activation loop is required for AvrPto-Pto interaction (Tang et al., "The avirulence protein AvrPto physically interacts with the Pto kinase." *Science* 274: 2060-2063 (1996); Frederick et al., "Recognition specificity for the bacterial avirulence protein AvrPto is determined by Thr-204 in the activation loop of the tomato Pto kinase." *Molecular Cell.* 2: 241-245 (1998), which are hereby incorporated by reference in their entirety). AvrPtoB specifically interacted with chimera G and not with other chimeric proteins, as shown in FIG. 10A (Tang et al., "The avirulence protein AvrPto physically interacts with the Pto kinase." *Science* 274: 2060-2063 (1996), which is hereby incorporated by reference in its entirety). Comparison of chimera G with the other chimeras implicated a region in Pto from amino acids 129 to 224 that is required for interaction with AvrPtoB. AvrPto also interacts with chimera G and elicits the HR in tomato plants expressing a chimeric G transgene (Tang et al., "The avirulence protein AvrPto physically interacts with the Pto kinase." *Science* 274: 2060-2063 (1996), which is hereby incorporated by reference in its entirety). Additional Pto-Fen chimeras that subdivide the Pto region spanning amino acids 113 to 217 were all found to interact with AvrPtoB as they do with AvrPto, as shown in FIG. 10B (Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety). AvrPtoB also interacted in an identical fashion as AvrPto with a large series of Pto and Fen mutants that previously served to define recognition specificity of Pto for AvrPto, as shown in FIG. 10C, (Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety). Taken together, AvrPtoB interacts with identical specificity as AvrPto with the Pto variants and these interactions thus indicate that T204 also forms a key recognition determinant of Pto for the AvrPtoB protein.

Further indication of the interaction specificity of AvrPtoB for Pto was obtained by examining a series of Pto proteins which contain single amino acid substitutions for eight previously identified autophosphorylation sites (Sessa et al., "Signal recognition and transduction mediated by the tomato Pto kinase: a paradigm of innate immunity in plants." *Microbes Infect,* 2: 1591-1597 (2000), which is hereby incorporated by reference in its entirety) and four Pto paralogs from the wild tomato species *L. hirsutum* (Riely et al., "Ancient origin of pathogen recognition specificity conferred by the tomato disease resistance gene Pto." *Proc. Natl. Acad. Sci. USA* 98: 2059-2064 (2001), which is hereby incorporated by reference in its entirety). A mutation at Thr-38 of Pto, the main autophosphorylation site in this kinase, abolishes the interaction with AvrPtoB as it does with AvrPto; all other phosphorylation site mutants interact with both AvrPtoB and AvrPto. Among the Pto kinases from *L. hirsutum*, only LhirPtoE interacts with the AvrPtoB and AvrPto proteins. Together, these observations demonstrate remarkable, and biologically meaningful, interaction specificity of the AvrPtoB protein for the Pto kinase.

Example 20

AvrPtoB Sequences are Conserved in at Least Three Genera of Bacterial Pathogens

Figure 11:
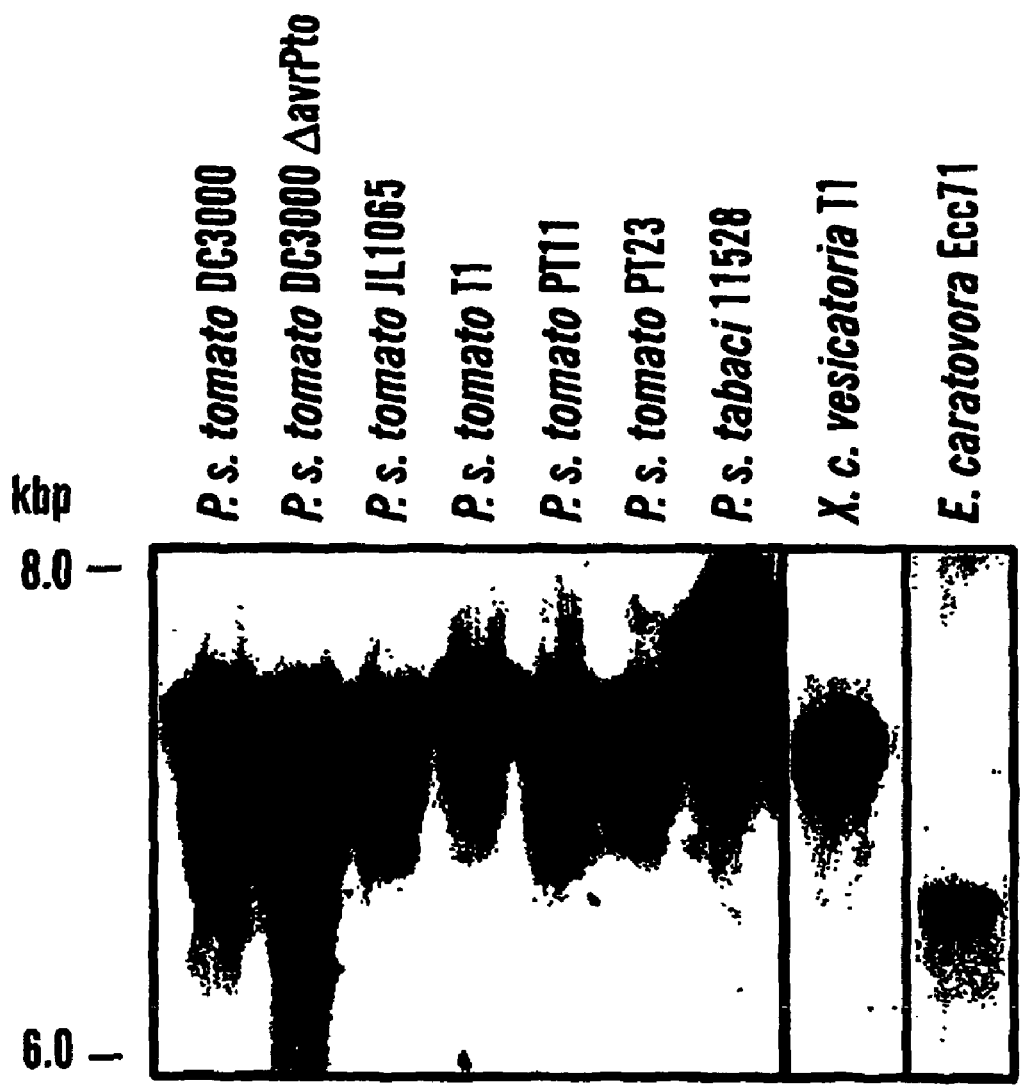
FIG. 11 shows DNA sequences with similarity to avrPtoB are present in diverse bacterial plant pathogens. DNA was isolated from the *Pseudoinonas, Xanthomonas,* or *Erwinia* strains indicated and analyzed on a gel blot using a radiolabeled avrPtoB gene probe. Stringency of the final wash was 0.1×SSC, 0.1% SDS.

To examine the distribution of avrPtoB-like sequences the gene was used to probe DNA blots containing genomic DNA from many *Pseudomonas* pathovars, and some *Xanthlononas* and *Erwinia* strains. It was discovered that sequences with homology to avrPtoB are present in certain strains of each of these three genera, as shown in FIG. 11. Because some of these strains (i.e. T1 and PT11) are virulent on Pto-expressing tomato leaves, as shown in Table 3 below, it has been concluded that not all of these avrPtoB sequences are recognized by Pto. Several of these DNA fragments were cloned and by partial sequence analysis have confirmed their relatedness to avrPtoB.

TABLE 3

Reaction of Tomato Leaves to Inoculation with P.s. pv. tomato Strains Expressing avrPtoB

| | Disease reaction[a] | |
|---|---|---|
| P.s. pv. tomato strain | RG-PtoR | RG-PtoS |
| T1 | + | + |
| T1(avrPto$_{JL1065}$) | − | + |

TABLE 3-continued

Reaction of Tomato Leaves to Inoculation
with P.s. pv. tomato Strains Expressing avrPtoB

| P.s. pv. tomato strain | Disease reaction[a] | |
|---|---|---|
| | RG-PtoR | RG-PtoS |
| T1(avrPtoB) | + | + |
| PT11 | + | + |
| PT11(avrPto$_{JL1065}$) | − | + |
| PT11(avrPtoB) | − | + |
| PT11(avrPtoB$^{1326T}$) | + | + |
| PT11(avrPtoB$^{G333A}$) | − | + |
| Bakersfield | + | + |
| Bakersfield(avrPto$_{JL1065}$) | − | + |
| Bakersfield(avrPtoB) | − | + |

[a]Leaves of 6-week old tomato plants RG-PtoR (Pto/Pto) or RG-PtoS (pto/pto) were vacuum infiltrated with 10$^4$ cfu/mL of the *Pseudomonas* strain indicated. Disease symptoms were recorded 5 days after inoculation. +, >40 specks per leaflet; − no specks observed.

Example 21

Expression of AvrPtoB in several *P. s. tomato* Strains Elicits Resistance to Bacterial Speck Disease in Tomato To determine if *P. s. tomato* strains carrying avrPtoB elicited Pto-specific disease resistance, three race 1 (virulent) strains of *P. s. tomato* (T1, PT11, and Bakersfield) that do not contain a functional avrPto gene were examined. The pDSK519::avrPtoB clone (or pDSK519::avrPto as a control) was introduced into these strains and a suspension of 10$^4$ cfu/mL was vacuum infiltrated into the leaves of resistant (RG-PtoR) or susceptible (RG-PtoS) tomato plants. As summarized in Table 3 above, no disease symptoms were observed on RG-PtoR plants inoculated with strains PT11 or Bakersfield expressing avrPtoB while RG PtoS plants were susceptible to these strains whether or not they carried avrPtoB. Identical results were observed for the avrPto-expressing strains. Interestingly, strain T1 elicited resistance in RG-PtoR only when expressing avrPto. Overall, these results confirmed that when expressed in at least two virulent strains of the bacterial speck pathogen, avrPtoB triggers plant resistance responses in a Pto-specific manner.

Example 22

AvrPtoB is Translocated by the Type III Secretion System to Plant Cells

The interaction of AvrPtoB with Pto and the Hrp-dependent expression of the gene suggested that AvrPtoB is an effector that travels the TTSS to gain access to the plant cell cytoplasm. To test if AvrPtoB is secreted by the TTSS a strain of *P. fluorescens* was used that carries the Hrp cluster from P. s. syringae strain 61. *P. fluorescens* was transformed with the pDSK519::avrPtoB plasmid. Infiltration of tomato leaves with this strain elicited a strong HR in the Pto-containing cultivar RG-PtoR but not in line RG-PtoS that lacks Pto, as shown in FIG. 11A. Infiltrated leaves of two tomato lines that contain inactive alleles of Pto or Prf also did not show induction of the HR. A *P. fluorescens* strain carrying the Hrp cluster but lacking AvrPtoB did not elicit an HR in any of the tomato lines. These results indicate that AvrPtoB is translocated into plant cells via the type m secretion system and that it is recognized specifically by the Pto locus in a Prf-dependent manner.

Example 23

Figure 12A:
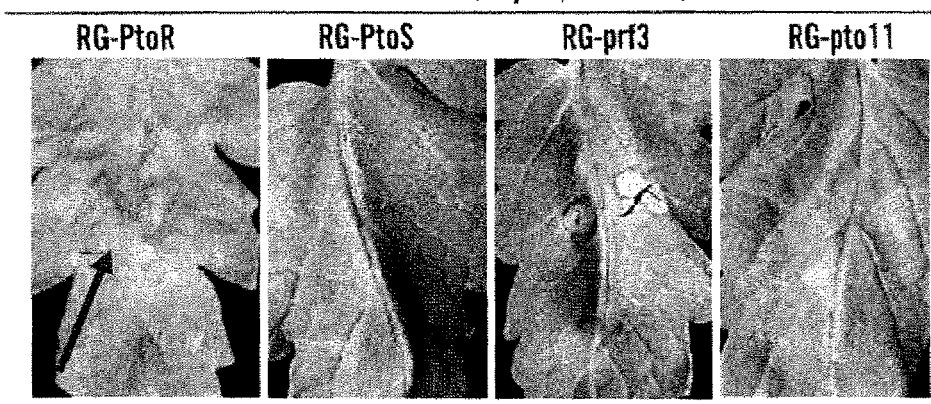
FIGS. 12A-C show AvrPtoB is secreted via the *Pseudomonas* type III secretion system and elicits a Pto- and Prf-specific HR in tomato leaves.
Figure 12B:
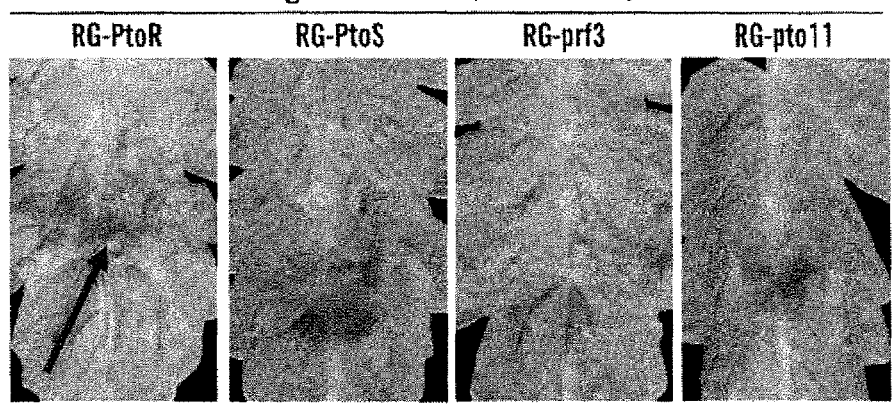

Expression of AvrPtoB Inside Tomato Leaf Cells Elicits a Pto- and Prf-Dependent HR Expression of many Avr proteins directly in plant cells elicits R gene specific defenses indicating that they are the sole bacterial determinants of an intracellular recognition mechanism. Whether avrPtoB activates R gene specific defense was tested from within the plant cell by infiltrating *A. tumefaciens* strain GV2260 containing a CaMV 35S: :avrPtoB construct into tomato leaves with or without a functional Pto pathway, as shown in FIG. 12B. Tomato leaves of line RG-PtoR exhibited an HR within 24 hours of infiltration whereas the other leaves did not. *A. tumefaciens* carrying the empty binary vector elicited no responses in any of the leaves.

Figure 12C:
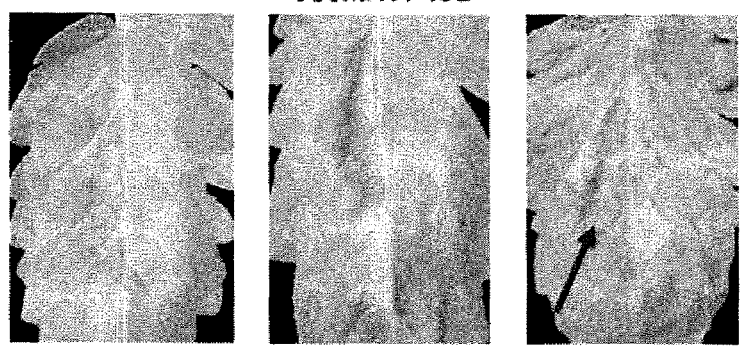

To confirm that AvrPtoB is recognized in tomato leaves specifically by the Pto kinase (and not another member of the Pto family), two *A. tumefaciens* strains containing either a 35S::avrPtoB construct or 35S::Pto construct were prepared and infiltrated either separately or as a mixture into leaves of the susceptible pto mutant, RG-pto11. Tomato leaves infiltrated with *A. tumefaciens* carrying 35S::avrPtoB alone exhibited no response in these leaves (this observation is in contrast to transient expression of avrPto which causes necrosis in susceptible tomato leaves; Chang et al., "avrPto enhances growth and necrosis caused by *Pseudomonas syringae* pv.tomato in tomato lines lacking either Pto or Prf." *Mol Plant Microbe Interact*, 13: 568-571 (2000), which is hereby incorporated by reference in its entirety). However, tomato leaves infiltrated with a mixture of the 35S::Pto and 35S:: avrPtoB strains developed an HR within 24 hr, as shown in FIG. 12C. Thus, AvrPtoB is specifically recognized in tomato leaves by the Pto kinase. An ancillary, but interesting, separate experiment revealed that infiltration of a mixture of *Agrobacterium* carrying 35S::avrPtoB and 35S::Pto into leaves of *Nicotiana benthamiana* or *N. tabacuin* W38 did not elicit an HR. This is in contrast to similar experiments using AvrPto (Scofield et al., "Molecular basis of gene-for-gene specificity in bacterial speck disease of tomato." *Science*, 274: 2063-2065 (1996); Frederick et al., "Recognition specificity for the bacterial avirulence protein AvrPto is determined by Thr-204 in the activation loop of the tomato Pto kinase." *Molecular Cell*. 2: 241-245 (1998), which are hereby incorporated by reference in their entirety) and might indicate that AvrPtoB requires a distinct host component(s) for Pto-mediated HR which is lacking in these *Nicotiana* species.

Example 24

AvrPtoB and AvrPto Proteins are Similar in Several Dispersed Regions

Although searches of GenBank using BLASTN and BLASTX failed to reveal sequence similarity between AvrPtoB and AvrPto, an alignment of the two proteins using DNASTAR did reveal similarities in several dispersed regions, as shown in FIG. 13A. The similarities between the two proteins have been used to designate nine subregions, I-IX, as shown in FIG. 13A.

Subregion I contains the putative myristylation site for AvrPto. This site is required for both avirulence and virulence activity of AvrPto but not for its physical interaction with Pto. As discussed above, AvrPtoB does not have a likely myristylation site (Nimchuk et al., "Eukaryotic fatty acylation drives plasma membrane targeting and enhances function of several type III effector proteins from *Pseudomonas syringae*." *Cell*.

101: 353-363 (2000), which is hereby incorporated by reference in its entirety). Subregion III of both AvrPto and AvrPtoB contains the consensus sequences "RxxLxxSxx-LxRxxxE" (SEQ ID NO: 49) and "SxRxR (SEQ ID NO: 50)." Interestingly, the first sequence is also found in a similar location in the protein sequences of VirPphA from P. s. phaseolicola race 7, AvrRpt2$_{JL1065}$ from P. s. tomato, and in less conserved form in several other Avr proteins, as shown in FIG. 13B. In AvrRpt2, this sequence lies in an N-terminus 7.5 kDa region which is essential for secretion and translocation, but not for in planta avirulence activity (Mudgett et al., "Characterization of the Pseudonmonas syringae pv. tomato Avr-Rpt2 protein: demonstration of secretion and processing during bacterial pathogenesis." Mol. Microbiol. 32: 927-941 (1999), which is hereby incorporated by reference in its entirety). A substitution mutation (H54P) within this region, when introduced into AvrPto and expressed in P. s. tomato or P. s. tabaci, abolishes its HR-eliciting activity in Pto-expressing leaves (Chang et al., "Functional studies of the bacterial avirulence protein AvrPto by mutational analysis." Mol. Plant-Microbe Interact. 14: 451-459 (2001), which is hereby incorporated by reference in its entirety). However, AvrPto (H54P) interacts with Pto in the yeast two-hybrid system and, when expressed directly within the plant cell, elicits an HR in N. benthamiana expressing CaMV35.-:Pto and (Chang et al., "Functional studies of the bacterial avirulence protein AvrPto by mutational analysis." Mol. Plant-Microbe Interact. 14: 451-459 (2001), which is hereby incorporated by reference in its entirety). Therefore, this subregion might play a role in secretion or in translocating AvrPto and AvrPtoB (and possibly other proteins that have this sequence) into the plant cell. Finally, it should be noted that the retrieval from the two-hybrid screen of AvrPtoB proteins lacking the first 121 amino acids indicates that neither subregions I, II or III are necessary for Pto binding in yeast.

Subregion IV contains four shared residues and one of them, S94 of AvrPto, was previously found to be important for interaction of AvrPto with Pto and for recognition by Pto in tomato (but not tobacco) cells (Shan et al., "The Pseudomonas AvrPto protein is differentially recognized by tomato and tobacco and is localized to the plant plasma membrane." Plant Cell 12: 2323-2337 (2000), which is hereby incorporated by reference in its entirety). In AvrPto, this residue lies next to a sequence that constitutes subregion V in our alignment. Subregion V consists of four conserved residues, GINP. Shan et al., "A cluster of mutations disrupt the avirulence but not the virulence function of AvrPto." MPMI, 13: 592-598 (2000), which is hereby incorporated by reference in its entirety, reported that a substitution in AvrPto at I96 in this sequence, or at the nearby G99 abolished recognition by Pto in yeast and tomato cells (G99, however, is not conserved in AvrPtoB). VirPphA from P. s. phaseolicola also has the GDIP sequence (Jackson et al., "Identification of a pathogenicity island, which contains genes for virulence and avirulence, on a large native plasmid in the bean pathogen Pseudomonas syringae pathovar phaseolicola." Proc Natl Acad Sci USA, 96: 10875-10880 (1999), which is hereby incorporated by reference in its entirety) and it has been found this protein both interacts with Pto in our yeast two-hybrid system and elicits an HR when expressed transiently in Pto-containing tomato leaves. Based on these observations it was speculated that residues in subregion V might be required for interaction of AvrPtoB with Pto (see below).

Finally, the alignment of AvrPto and AvrPtoB revealed four other discrete regions of shared amino acids in the C-terminal region. Deletion of the C-terminal 40 amino acids of AvrPto does not affect its interaction with Pto in yeast (Chang et al., "Functional studies of the bacterial avirulence protein AvrPto by mutational analysis." Mol. Plant-Microbe Interact. 14: 451-459 (2001), which is hereby incorporated by reference in its entirety) and this suggests that subregions VIII and IX of AvrPtoB are not required for Pto interaction. Substitutions at N145, P146, S147, or S153 of AvrPto abolished its ability to elicit the HR in tobacco line W38 raising the possibility that another Pto-like R protein exists in that line (Shan et al., "The Pseudomonas AvrPto protein is differentially recognized by tomato and tobacco and is localized to the plant plasma membrane." Plant Cell 12: 2323-2337 (2000), which is hereby incorporated by reference in its entirety). N511 and P512 of AvrPtoB might serve a similar function although AvrPtoB also has an NPSxxxxxS (SEQ ID NO: 51) motif near subregion V (i.e., N327, P328, S329, S335). It has been found that expression of AvrPtoB in W38 does not elicit the HR but whether this is due to the different locations of this motif in the proteins or some other reason is not known.

Example 25

Figure 14:
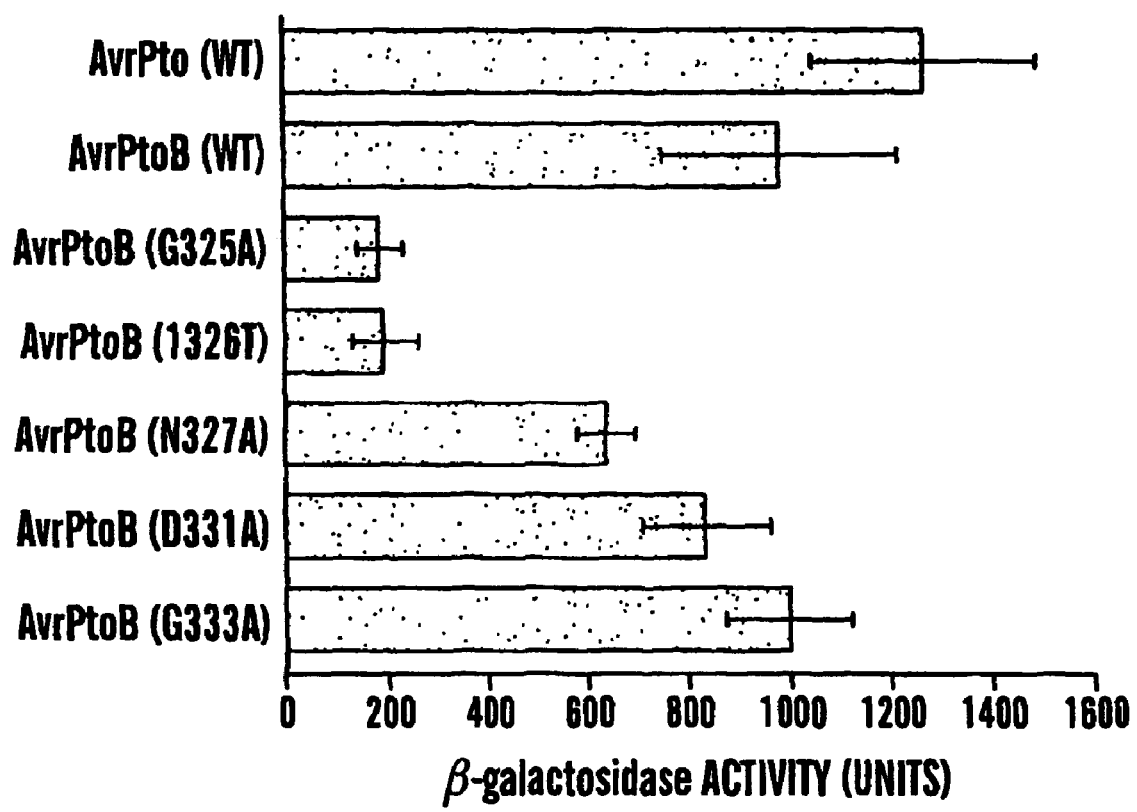
FIG. 14 shows a motif shared by AvrPtoB and AvrPto is required for interaction with the Pto kinase. Amino acid substitutions in and near subregion V were created in AvrPtoB and the mutant proteins were tested for interaction with the Pto kinase in the LexA yeast two-hybrid system. Degree of lacZ reporter gene activation was determined by measuring relative units of β-galactosidase activity in yeast strains expressing the mutant proteins and Pto (as in Frederick et al., "Recognition specificity for the bacterial avirulence protein AvrPto is determined by Thr-204 in the activation loop of the tomato Pto kinase." *Molecular Cell.* 2: 241-245 (1998), which is hereby incorporated by reference in its entirety). The β-galactosidase activity data are the means (gray boxes) and standard errors (error bars) of duplicate experiments each with three independent colonies per construct.
Figure 15:
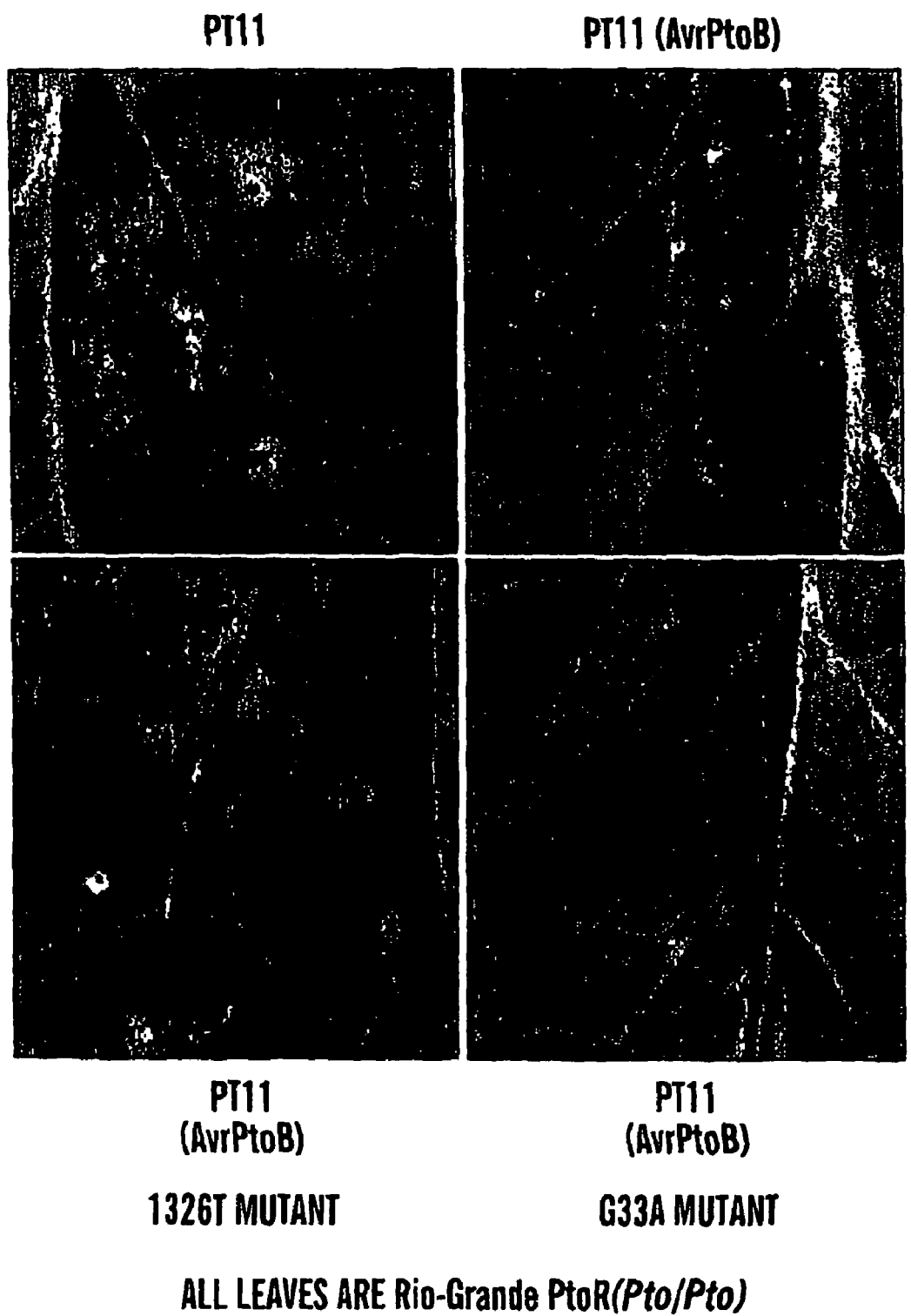
FIG. 15 shows tomato leaves (variety Rio Grande-PtoR) expressing Pto that were inoculated with the *Pseudomonas syringae* pv. tomato strain PT11 or derivatives of this strain. In the top right panel PT11 expresses avrPtoB from an introduced plasmid (PT11(avrPtoB)). In the bottom panels, PT11 expresses mutant versions of avrPtoB from an introduced plasmid (the mutations each cause a substitution of one amino acid: isoleucine to threonine at amino acid position 326 or glycine to alanine at amino acid position 333. The conclusion from the experiments is that introduction of avrPtoB into the normally disease-causing strain PT11 allows it to now be recognized by Pto. Mutation of a residue at position 326 abolishes this recognition while a mutation at position 333 does not affect it. This data supports a role for subdomain V in the recognition of AvrPtoB by the Pto kinase (as also supported by data presented in Table 2).

Subregion V of AvrPtoB Contains Recognition Determinants for Interaction with Pto A series of point mutations in AvrPtoB was developed to determine if subregion V, which is required for AvrPto interaction with Pto (Shan et al., "The Pseudomonas AvrPto protein is differentially recognized by tomato and tobacco and is localized to the plant plasma membrane." Plant Cell 12: 2323-2337 (2000), which is hereby incorporated by reference in its entirety), is also required for the AvrPtoB-Pto interaction, as shown in FIG. 14. Each AvrPtoB point mutant was co-expressed with Pto in the yeast two-hybrid system and activation of the lacZ reporter gene was measured. Expression of the mutant proteins was confirmed by western blots. Substitutions G325A, I326T, or N327A of AvrPtoB reduced the interaction with Pto as compared with wildtype AvrPtoB (SEQ ID NO:2), as shown in FIG. 14. Point mutations in nearby residues D331 and G333, which do not correspond to AvrPto residues, resulted in lacZ expression that was not statistically different from wildtype AvrPtoB. Two of these mutated avrPtoB genes were transformed into the virulent Pseudomonas strain PTII and examined their avirulence activity on RG-PtoR and RG-PtoS tomato leaves. Consistent with the two-hybrid data, AvrPtoB(I326T) (SEQ ID NO:2) did not elicit disease resistance on Pto-expressing leaves while AvrPtoB(G333A) (SEQ ID NO:2) elicited Pto-specific defense, as shown in Table 3. Thus, subregion V of AvrPto and AvrPtoB plays an important role in the Pto interaction and HR-eliciting activity of these effectors.

Example 26

Two Distinct Pseudomonas Effector Proteins Interact with the Pto Kinase and Activate Plant Immunity A second Pseudomonas protein, AvrPtoB, was identified that interacts with the Pto kinase and elicits Pto-specific and Prf-dependent disease resistance in tomato leaves. Speculation that such a protein exists arose after it was found that deletion of AvrPto from P. s. tomato strains JL1065 or DC3000 did not alter the avirulence of these strains on Pto-expressing tomato leaves. It was hypothesized that, like AvrPto, this putative second effector might also interact directly with the Pto kinase in a yeast two-hybrid system. A cross-kingdom yeast two-hybrid screen was employed and it permitted rapid and efficient isolation of AvrPtoB. AvrPto and AvrPtoB proteins have exactly the same interaction specificity for Pto in the yeast two-hybrid system and despite many differences they share several small, discrete, subregions in common. Subregion V plays a key role in the interaction with the Pto kinase and it is possible that other subregions also have conserved roles. These findings demonstrate that distinct bacterial effector proteins interact with the Pto kinase by using a common structural mechanism.

A yeast two-hybrid screen involving 12 *Pseudomonas* genomic prey libraries and a Pto bait construct was used to isolate AvrPtoB. The *Pseudomonas* genome is about 6.6 Mb, and, therefore, the screening of $5 \times 10^7$ random prey clones with an average insert size of 1 kb provides a >99.9% probability of testing every *Pseudomonas* genome sequence in the proper reading frame at least once for interaction with Pto. By using the DC3000 genome sequence (www.tigr.org) each of the PtiDC clones recovered were examined, as shown in Table 2 above, and, so far, have observed a Hrp box upstream of only the AvrPtoB open reading frame. Thus, unless the type III pathway also secretes non-Hrp-regulated proteins, it is likely that the interactions with Pto of the other proteins that were identified are not biologically meaningful. Eight AvrPtoB clones were recovered including some that were missing up to 121 amino acids from the N terminus of AvrPtoB but no clones that were missing anything downstream of this point. Because of the high probability that many subfragments of AvrPtoB are present in the *Pseudomonas* prey libraries these results suggest that structural features spanning the C-terminal 432 amino acids of AvrPtoB are required for its interaction with Pto.

Several lines of evidence indicate that AvrPtoB is an effector that plays a role in restricting host range of *Pseudomonas*. First, in common with all previously identified Avr genes the avrPtoB promoter contains a consensus Hrp box. As expected, expression of avrPtoB is induced by growth medium that simulates the apoplastic fluid of plant leaves and is controlled by the Hrp regulon. Secondly, it was shown that delivery of AvrPtoB from *P. fluresceils* to plant cells is strictly dependent upon the presence of the TTSS encoded by the Htp cluster. Third, the delivery of AvrPtoB from two normally virulent *Pseudomonas* strains or by *Agrobacterium*-mediated expression in the plant cell is detectable based on the specific recognition of the protein by the Pto kinase. Because Pto is localized within the plant cell this observation indicates that, as with many other Avr proteins (reviewed in Kjemtrup et al., "Effector proteins of phytopathogenic bacteria: bifunctional signals in virulence and host recognition." *Curr. Opin. Microbiol.* 3: 73-78 (2000), which is hereby incorporated by reference in its entirety), AvrPtoB is active inside the plant cell. Finally, there is the similarity of AvrPtoB to the VirPphA protein. VirPphA was originally identified in a *P. s. phaseolicola* strain as a virulence factor, because it promotes watersoaking by the pathogen in a bean pod assay. It was subsequently found to confer avirulence to *P. s. phaseolicola* bacteria infiltrated into soybean leaves (Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*. 96: 10875-10880 (1999), which is hereby incorporated by reference in its entirety). In a related study, it was found that AvrPtoB also promotes watersoaking in the bean pod assay and, therefore, has virulence activity, too. VirPphA also interacts with Pto in the yeast two-hybrid system and elicits a Pto-specific HR in tomato leaves. Thus, the alignment of the two proteins, as shown in FIG. 9C should expedite the identification of key residues in each protein that play a role in avirulence and virulence.

It was found that avrPtoB did not confer avirulence on all *P. s. tomato* strains tested, as shown in Table 3 above. This is consistent with the fact that AvrPtoB was not isolated previously by screening of DC3000 cosmids in a virulent strain of *Pseudonmonas* (Ronald et al., "The cloned avirulence gene avrPto induces disease resistance in tomato cultivars containing the Pto resistance gene." 174: 1604-1611 (1992), which is hereby incorporated by reference in its entirety). It is possible that another *Pseudomonas* protein (e.g. a chaperone) is required for the effective secretion or translocation of AvrPtoB from *Pseudomonas* and that this factor is not present in all *P. s. tomato* strains. It is also possible that expression of AvrPtoB in certain bacterial strains is "masked" as observed for some effectors in *P. s. phaseolicola* (Jackson et al., "Identification of a pathogenicity island, which contains genes for virulence and avirulence, on a large native plasmid in the bean pathogen *Pseudomonas syringae* pathovar *phaseolicola*." *Proc Natl Acad Sci USA*. 96: 10875-10880 (1999), which is hereby incorporated by reference in its entirety).

AvrPto was previously found to interact with certain Pto variants, and these proteins were used to define residue T204 of Pto as a key determinant of recognition specificity for AvrPto (Frederick et al., "Recognition specificity for the bacterial avirulence protein AvrPto is determined by Thr-204 in the activation loop of the tomato Pto kinase." *Molecular Cell*. 2: 241-245 (1998), which is hereby incorporated by reference in its entirety). Remarkably, AvrPtoB interacts with the same Pto variants as AvrPto and, thus, T204 is also a key Pto determinant for interaction with AvrPtoB. AvrPtoB also interacts with the one AvrPto-interacting member of the Pto family isolated from a bacterial speck-resistant wild species of tomato, *Lycopersicon hirsutum*. These observations suggest that there has been selection in *Lycopersicon* spp. over a long period of time for Pto-kinases that specifically recognize a conserved feature present in both the AvrPto and AvrPtoB proteins.

Dual recognition specificity previously has been reported for three other plant R proteins (i.e. RPM1, RPP8/HRT, Mi1; for review see Dangl et al., "Plant pathogens and integrated defence responses to infection." *Nature* 411: 826-833 (2001), which is hereby incorporated by reference in its entirety). However, in none of these cases have the host and pathogen proteins been shown to interact directly. Thus, the dual (or perhaps even multiple) recognition specificity of R proteins may turn out to be a common feature of plant defense responses. This notion is consistent with the recent report that *Arabidopsis* contains only 150 putative R loci (of the NB-LRR class) yet is likely defending itself against many thousands of potential plant pathogens (Dangl et al., "Plant pathogens and integrated defence responses to infection." *Nature* 411: 826-833 (2001), which is hereby incorporated by reference in its entirety). Although the pathogen proteins recognized by most of these R genes are unknown, the present work suggests that common structural motifs embedded within diverse pathogen proteins might play a role in their recognition. Finally, if the possibility that the Pto kinase originally might have been an important target for several bacterial virulence proteins is considered, then the data are also consistent with the "guard" hypothesis which postulates that NB-LRR proteins (e.g. Prf) have evolved to interact with a complex of Avr proteins and their virulence targets (Dangl et al., "Plant pathogens and integrated defence responses to infection." *Nature* 411: 826-833 (2001), which is hereby incorporated by reference in its entirety).

A detailed structure-function analysis of both Avr proteins will be necessary to fully understand the importance of residues conserved between them. This analysis began by examining subregion V (the "GINP motif"), because it is perfectly conserved in both AvrPto and AvrPtoB and previous work with AvrPto found that several residues within this subregion are required for interaction with Pto (Shan et al., "A cluster of mutations disrupt the avirulence but not the virulence function of AvrPto." *MPMI*, 13: 592-598 (2000), which is hereby incorporated by reference in its entirety). Substitutions in the three residues examined in subregion V significantly decreased interaction of AvrPtoB with Pto while substitutions just outside subregion V did not. These results, along with the previous findings with AvrPto, suggest that the GINP motif may play a role as contact point between the Pto kinase and these two effector proteins. Alternatively, the GINP motif could affect the structure of another part of these proteins that interacts with Pto. The three-dimensional structure of the AvrPto protein is currently being determined, and this will allow further examination of the role of the GINP motif in Pto recognition.

Although avrPto-like sequences occur only in a subset of *Pseudomonas* strains that are known to be avirulent on Pto-expressing tomato plants (Ronald et al., "The cloned avirulence gene avrPto induces disease resistance in tomato cultivars containing the Pto resistance gene." 174: 1604-1611 (1992), which is hereby incorporated by reference in its entirety) avrPtoB-like sequences are present in at least three genera of bacterial phytopathogens, as shown in FIG. 11. AvrPtoB is one of only a few known Avr genes to show this wide distribution (White et al., "Prospects for understanding avirulence gene function." *Curr. Opin. Plant Biol.* 3: 291-298 (2000), which is hereby incorporated by reference in its entirety). It might be anticipated that widely conserved effectors serve as virulence factors, and this appears to be the case for AvrPtoB. Several avrPtoB-related sequences have been cloned from selected *Pseudomonas, Erwinia*, and *Xanthonionas* strains and from preliminary sequence analysis find a high degree of similarity among them. Future study of the AvrPtoB/VirPphA family will reveal if it plays a conserved role in promoting virulence in these diverse phytopathogens.

Although these studies revealed many similarities between AvrPto and AvrPtoB, some striking and intriguing differences were also observed. First, are the differences in the genes and corresponding proteins. AvrPtoB-like sequences are widely distributed whereas avrPto-like sequences have not been observed outside of the *Pseudonmonas* spp. The proteins encoded by each gene are very different with AvrPtoB, at 59 kD, over three times the mass of AvrPto at 18 kD. There are sequence similarities at both the N— and C termini of the proteins and the main additions of AvrPtoB lie within four large internal segments. It was also found that, unlike AvrPto, the AvrPtoB protein lacks a myristylation motif at the penultimate position of the N terminus. The myristylation motif of AvrPto is required for both its avirulence and virulence activity and also for association of AvrPto with the membrane fraction (Shan et al., "A cluster of mutations disrupt the avirulence but not the virulence function of AvrPto." *MPMI*, 13: 592-598 (2000), which is hereby incorporated by reference in its entirety). The possibility that AvrPtoB protein might be processed to reveal an internal myristylation motif like, the AvrPphB protein, cannot be excluded (Nimchuk et al., "Eukaryotic fatty acylation drives plasma membrane targeting and enhances function of several type III effector proteins from *Pseudomonas syringae*." *Cell.* 101: 353-363 (2000), which is hereby incorporated by reference in its entirety). However, in preliminary experiments using an AvrPtoB::GFP fusion, the protein does not appear to localize specifically to the cell periphery.

The second major difference observed between AvrPto and AvrPtoB is their apparent activity in plant cells. Unlike avrPto, the expression of avrPtoB in susceptible tomato or *N. benthamiana* leaves does not cause severe yellowing and necrosis that is dependent on the presence of Prf (Chang et al., "avrPto enhances growth and necrosis caused by *Pseudomonas syringae* pv.tomato in tomato lines lacking either Pto or Prf." *Mol Plant Microbe Interact*, 13: 568-571 (2000), which is hereby incorporated by reference in its entirety). It is not clear whether this AvrPto-mediated necrosis is a defense or susceptibility response, but the lack of the response in leaves expressing AvrPtoB might indicate that the two proteins target different host proteins as susceptibility targets when Pto is not present. In this regard, it will be interesting to see if host proteins that are known to interact with AvrPto or the AvrPto-Pto complex will also do so with AvrPtoB or AvrPtoB-Pto (Bogdanove et al., "AvrPto-dependent Pto-interacting proteins and AvrPto-interacting proteins in tomato." *Proc. Natl. Acad. Sci. USA* 97: 8836-8840 (2000), which is hereby incorporated by reference in its entirety). Finally, it was surprising to discover that co-expression of AvrPtoB and Pto in leaves of *N. benthamiana* did not lead to an HR as does co-expression of AvrPto and Pto. This suggests that, although both effectors target the Pto kinase, they each may require additional and distinct host proteins for their avirulence activities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting programmed cell death in a plant or yeast eukaryote, said method comprising:
administering to the plant or yeast eukaryote a bacterial effector protein which inhibits programmed cell death, wherein the protein comprises either: (1) the amino acid sequence of SEQ ID NO: 2; or (2) the amino acid sequence spanning amino acids 308 and 553 of SEQ ID NO: 2.

2. The method according to claim 1, wherein the protein comprises the amino acid sequence of SEQ ID NO: 2.

3. The method according to claim 1, wherein the protein comprises the amino acid sequence spanning amino acids 308 and 553 of SEQ ID NO: 2.

4. The method according to claim 1, wherein the eukaryote is a plant.

5. The method according to claim 1, wherein the eukaryote is a yeast.

* * * * *

UNITED STATES PATENT AND TRADEMARK OFFICE
CERTIFICATE OF CORRECTION

PATENT NO. : 7,888,467 B2  
APPLICATION NO. : 10/524750  
DATED : February 15, 2011  
INVENTOR(S) : Martin et al.

Page 1 of 1

It is certified that error appears in the above-identified patent and that said Letters Patent is hereby corrected as shown below:

Col. 1 at lines 9-13, delete the following paragraph:
"The subject matter of this application was made with support from the United States Government under the United States Department of Agriculture NRI Grant No. 99-35301-7973 and the National Science Foundation Grant No. DBI-0077622. The Government may have certain rights."
and insert the following paragraph in its place:
--This invention was made with government support under NRI Grant No. 99-35301-7973 awarded by the United States Department of Agriculture and Grant No. DBI-0077622 awarded by the National Science Foundation. The government has certain rights in this invention.--

Signed and Sealed this
Twenty-eighth Day of August, 2012

David J. Kappos
*Director of the United States Patent and Trademark Office*

SEQUENCE LISTING

```
<160> NUMBER OF SEQ ID NOS: 54

<210> SEQ ID NO 1
<211> LENGTH: 1662
<212> TYPE: DNA
<213> ORGANISM: Pseudomonas syringae

<400> SEQUENCE: 1
atggcgggta tcaatagagc gggaccatcg ggcgcttatt ttgttggcca cacagacccc      60
```

-continued

```
gagccagtat cggggcaagc acacggatcc ggcagcggcg ccagctcctc gaacagtccg    120
caggttcagc cgcgaccctc gaatactccc ccgtcgaacg cgcccgcacc gccgccaacc    180
ggacgtgaga ggctttcacg atccacggcg ctgtcgcgcc aaaccaggga gtggctggag    240
cagggtatgc ctacagcgga ggatgccagc gtgcgtcgta ggccacaggt gactgccgat    300
gccgcaacgc cgcgtgcaga ggcaagacgc acgccgagg caactgccga tgccagcgca     360
ccgcgtagag gggcggttgc acacgccaac agtatcgttc agcaattggt cagtgagggc    420
gctgatattt cgcatactcg taacatgctc cgcaatgcaa tgaatggcga cgcagtcgct    480
ttttctcgag tagaacagaa catatttcgc cagcatttcc cgaacatgcc catgcatgga    540
atcagccgag attcggaact cgctatcgag ctccgtgggg cgcttcgtcg agcggttcac    600
caacaggcgg cgtcagcgcc agtgaggtcg cccacgccaa caccggccag ccctgcggca    660
tcatcatcgg gcagcagtca gcgttcttta tttggacggt ttgcccgttt gatggcgcca    720 aaccaggggac ggtcgtcgaa cactgccgcc tctcagacgc cggtcgacag gagcccgcca   780
cgcgtcaacc aaagacccat acgcgtcgac agggctgcga tgcgtaatcg tggcaatgac    840
gaggcggacc ccgcgctgcg ggggttagta caacaggggg tcaatttaga gcacctgcgc    900
acggcccttg aaagacatgt aatgcagcgc ctccctatcc ccctcgatat aggcagcgcg    960
ttgcagaatg tgggaattaa cccaagtatc gacttggggg aaagccttgt gcaacatccc   1020
ctgctgaatt tgaatgtagc gttgaatcgc atgctggggc tgcgtcccag cgctgaaaga   1080
gcgcctcgtc cagccgtccc cgtggctccc gcgaccgcct ccaggcgacc ggatggtacg   1140
cgtgcaacac gattgcgggt gatgccggag cgggaggatt acgaaaataa tgtggcttat   1200
ggagtgcgct tgcttaacct gaacccgggg gtggggtaa ggcaggctgt tgcggccttt    1260
gtaaccgacc gggctgagcg gccagcagtg gtggctaata tccgggcagc cctggaccct   1320
atcgcgtcac aattcagtca gctgcgcaca atttcgaagg ccgatgctga atctgaagag   1380 ctgggttta aggatgcggc agatcatcac acggatgacg tgacgcactg tcttttggc    1440 ggagaattgt cgctgagtaa tccggatcag caggtgatcg gtttggcggg taatccgacg   1500
gacacgtcgc agccttacag ccaagaggga ataaggacc tggcgttcat ggatatgaaa     1560
aaacttgccc aattcctcgc aggcaagcct gagcatccga tgaccagaga aacgcttaac   1620
gccgaaaata tcgccaagta tgcttttaga atagtcccct ga                      1662
```

<210> SEQ ID NO 2
<211> LENGTH: 553
<212> TYPE: PRT
<213> ORGANISM: Pseudomonas syringae

<400> SEQUENCE: 2

```
Met Ala Gly Ile Asn Arg Ala Gly Pro Ser Gly Ala Tyr Phe Val Gly
 1               5                  10                  15

His Thr Asp Pro Glu Pro Val Ser Gly Gln Ala His Gly Ser Gly Ser
                20                  25                  30

Gly Ala Ser Ser Asn Ser Pro Gln Val Gln Pro Arg Pro Ser Asn
            35                  40                  45

Thr Pro Pro Ser Asn Ala Pro Ala Pro Pro Thr Gly Arg Glu Arg
        50                  55                  60

Leu Ser Arg Ser Thr Ala Leu Ser Arg Gln Thr Arg Glu Trp Leu Glu
 65                  70                  75                  80

Gln Gly Met Pro Thr Ala Glu Asp Ala Ser Val Arg Arg Arg Pro Gln
                85                  90                  95
```

```
Val Thr Ala Asp Ala Ala Thr Pro Arg Ala Glu Ala Arg Arg Thr Pro
            100                 105                 110

Glu Ala Thr Ala Asp Ala Ser Ala Pro Arg Arg Gly Ala Val Ala His
        115                 120                 125

Ala Asn Ser Ile Val Gln Gln Leu Val Ser Glu Gly Ala Asp Ile Ser
    130                 135                 140

His Thr Arg Asn Met Leu Arg Asn Ala Met Asn Gly Asp Ala Val Ala
145                 150                 155                 160

Phe Ser Arg Val Glu Gln Asn Ile Phe Arg Gln His Phe Pro Asn Met
                165                 170                 175

Pro Met His Gly Ile Ser Arg Asp Ser Glu Leu Ala Ile Glu Leu Arg
            180                 185                 190

Gly Ala Leu Arg Arg Ala Val His Gln Gln Ala Ala Ser Ala Pro Val
        195                 200                 205

Arg Ser Pro Thr Pro Thr Pro Ala Ser Pro Ala Ala Ser Ser Ser Gly
    210                 215                 220

Ser Ser Gln Arg Ser Leu Phe Gly Arg Phe Ala Arg Leu Met Ala Pro
225                 230                 235                 240

Asn Gln Gly Arg Ser Ser Asn Thr Ala Ala Ser Gln Thr Pro Val Asp
                245                 250                 255

Arg Ser Pro Pro Arg Val Asn Gln Arg Pro Ile Arg Val Asp Arg Ala
            260                 265                 270

Ala Met Arg Asn Arg Gly Asn Asp Glu Ala Asp Ala Ala Leu Arg Gly
        275                 280                 285

Leu Val Gln Gln Gly Val Asn Leu Glu His Leu Arg Thr Ala Leu Glu
    290                 295                 300

Arg His Val Met Gln Arg Leu Pro Ile Pro Leu Asp Ile Gly Ser Ala
305                 310                 315                 320

Leu Gln Asn Val Gly Ile Asn Pro Ser Ile Asp Leu Gly Glu Ser Leu
                325                 330                 335

Val Gln His Pro Leu Leu Asn Leu Asn Val Ala Leu Asn Arg Met Leu
            340                 345                 350

Gly Leu Arg Pro Ser Ala Glu Arg Ala Pro Arg Pro Ala Val Pro Val
        355                 360                 365

Ala Pro Ala Thr Ala Ser Arg Arg Pro Asp Gly Thr Arg Ala Thr Arg
    370                 375                 380

Leu Arg Val Met Pro Glu Arg Glu Asp Tyr Glu Asn Asn Val Ala Tyr
385                 390                 395                 400

Gly Val Arg Leu Leu Asn Leu Asn Pro Gly Val Gly Val Arg Gln Ala
                405                 410                 415

Val Ala Ala Phe Val Thr Asp Arg Ala Glu Arg Pro Ala Val Val Ala
            420                 425                 430

Asn Ile Arg Ala Ala Leu Asp Pro Ile Ala Ser Gln Phe Ser Gln Leu
        435                 440                 445

Arg Thr Ile Ser Lys Ala Asp Ala Glu Ser Glu Glu Leu Gly Phe Lys
    450                 455                 460

Asp Ala Ala Asp His His Thr Asp Asp Val Thr His Cys Leu Phe Gly
465                 470                 475                 480

Gly Glu Leu Ser Leu Ser Asn Pro Asp Gln Gln Val Ile Gly Leu Ala
                485                 490                 495

Gly Asn Pro Thr Asp Thr Ser Gln Pro Tyr Ser Gln Glu Gly Asn Lys
            500                 505                 510
```

```
Asp Leu Ala Phe Met Asp Met Lys Lys Leu Ala Gln Phe Leu Ala Gly
        515                 520                 525

Lys Pro Glu His Pro Met Thr Arg Glu Thr Leu Asn Ala Glu Asn Ile
    530                 535                 540

Ala Lys Tyr Ala Phe Arg Ile Val Pro
545                 550

<210> SEQ ID NO 3
<211> LENGTH: 1740
<212> TYPE: DNA
<213> ORGANISM: Pseudomonas syringae

<400> SEQUENCE: 3
atggcgggta tcaatggagc gggaccatcg ggcgcttatt ttgttggcca cacagacccc      60
gagccagcat cggggggcgc acacggatcc agcagtggcg cgagatcctc gaacagtccg     120
cgcttgccgg cgcctccgga tgcacccgcg tcgcaggcgc gagatcgacg cgaaatgctt     180
ttgcgagcca ggccgctgtc gcgccaaacc agggagtggg tggcgcaggg tatgccgcca     240
acggcggagg ctggagtgcc atcaggccg caggagtctg ccgaggctgc agcgccgcag     300
gcacgtgcag aggaaagaca cacgccggag gctgatgcag cagcgtcgca tgtacgcaca     360
gagggaggac gcacaccgca ggcgcttgcc ggtacctccc cacgccacac aggtgcggtg     420
ccacacgcca atagaattgt caacaattg gttgacgcgg cgctgatct tgccggtatt       480
aacaccatga ttgacaatgc catgcgtcgc cacgcgatag ctcttccttc tcgaacagta     540
cagagtattt tgatcgagca tttccctcac ctgctagcgg gtgaactcat tagtggctca     600
gagctcgcta ccgcgttccg tgcggctctc cgtcgggagg ttcgccaaca ggaggcgtca     660
gcccccccaa gaacagcagc gcggtcctcc gtaaggacgc cggagcggtc gacggtgccg     720
cccacttcta cggaatcatc atcgggcagc aaccagcgta cgttattagg gcggttcgcc     780
gggttgatga cgcctaatca gagacgtccg tcgagcgctt cgaacgcgtc tgcctctcaa     840
aggcctgtag acagaagccc gccacgcgta accaggtac ccacaggcgc taacagggtt      900
gtgatgcgta tcatggtaa taacgaggcc gacgccgcgc tgcaaggatt ggctcagcag     960
ggggttgata tggaggacct cgcgccgcg cttgaaagac atatattgca tcgccgcccg     1020
atccccatgg atatagcgta cgccttgcag ggtgtgggca ttgcgccaag tatcgatacg    1080
ggagagagcc ttatggaaaa cccgctgatg aatttgagtg ttgcgctgca ccgcgcacta    1140
gggcctcgtc ccgctcgtgc tcaagcgcct cgtccagccg ttccggtggc tcccgcgacc    1200
gtctccaggc gaccagatag cgcgcgtgcc acaagattgc aggtaatacc ggcgcgggag    1260
gattacgaaa ataatgtggc ctacggagtg cgcttgctga gcctgaatcc gggcgcgggg    1320
gtcagggaga ctgttgcggc cttttgaaac aaccgttacg agcggcaggc ggttgttgcc    1380
gacatacgcg cagccctaaa tttatctaaa caattcaata agttgcgtac ggtctctaag    1440
gccgatgctg cctccaataa accgggcttc aaggatgcgg cggaccaccc agacgacgcg    1500
acgcaatgcc tttttggtga agaattgtcg ctgaccagtt cggatcagca ggtgatcggc    1560
ctggcaggta aggcaacgga catgtcggag tcttacagcc gagaggcaaa taaggacctg    1620
gtgttcatgg atatgaaaaa acttgcccaa ttcctcgcag gcaagcctga gcatccgatg    1680
accagagaaa cgcttaacgc cgaaaatatc gccaagtatg cttttagaat agtcccctga    1740

<210> SEQ ID NO 4
<211> LENGTH: 579
<212> TYPE: PRT
```

<213> ORGANISM: Pseudomonas syringae

<400> SEQUENCE: 4

```
Met Ala Gly Ile Asn Gly Ala Gly Pro Ser Gly Ala Tyr Phe Val Gly
 1               5                  10                  15

His Thr Asp Pro Glu Pro Ala Ser Gly Ala His Gly Ser Ser Ser
             20                  25                  30

Gly Ala Arg Ser Ser Asn Ser Pro Arg Leu Pro Ala Pro Pro Asp Ala
         35                  40                  45

Pro Ala Ser Gln Ala Arg Asp Arg Arg Glu Met Leu Leu Arg Ala Arg
     50                  55                  60

Pro Leu Ser Arg Gln Thr Arg Glu Trp Val Ala Gln Gly Met Pro Pro
 65                  70                  75                  80

Thr Ala Glu Ala Gly Val Pro Ile Arg Pro Gln Glu Ser Ala Glu Ala
                 85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
        115                 120                 125

Leu Ala Gly Thr Ser Pro Arg His Thr Gly Ala Val Pro His Ala Asn
    130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
            180                 185                 190

Ala Gly Glu Leu Ile Ser Gly Ser Glu Leu Ala Thr Ala Phe Arg Ala
        195                 200                 205

Ala Leu Arg Arg Glu Val Arg Gln Gln Glu Ala Ser Ala Pro Pro Arg
    210                 215                 220

Thr Ala Arg Ser Ser Val Arg Thr Pro Glu Arg Ser Thr Val Pro
225                 230                 235                 240

Pro Thr Ser Thr Glu Ser Ser Gly Ser Asn Gln Arg Thr Leu Leu
                245                 250                 255

Gly Arg Phe Ala Gly Leu Met Thr Pro Asn Arg Arg Pro Ser Ser
            260                 265                 270

Ala Ser Asn Ala Ser Ala Ser Gln Arg Pro Val Asp Arg Ser Pro Pro
        275                 280                 285

Arg Val Asn Gln Val Pro Thr Gly Ala Asn Arg Val Val Met Arg Asn
    290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
            340                 345                 350

Gly Ile Ala Pro Ser Ile Asp Thr Gly Glu Ser Leu Met Glu Asn Pro
        355                 360                 365

Leu Met Asn Leu Ser Val Leu His Arg Ala Leu Gly Pro Arg Pro
    370                 375                 380

Ala Arg Ala Gln Ala Pro Arg Pro Ala Val Pro Val Ala Pro Ala Thr
385                 390                 395                 400
```

-continued

```
Val Ser Arg Arg Pro Asp Ser Ala Arg Ala Thr Arg Leu Gln Val Ile
                405                 410                 415
Pro Ala Arg Glu Asp Tyr Glu Asn Asn Val Ala Tyr Gly Val Arg Leu
            420                 425                 430
Leu Ser Leu Asn Pro Gly Ala Gly Val Arg Glu Thr Val Ala Ala Phe
        435                 440                 445
Val Asn Asn Arg Tyr Glu Arg Gln Ala Val Val Ala Asp Ile Arg Ala
    450                 455                 460
Ala Leu Asn Leu Ser Lys Gln Phe Asn Lys Leu Arg Thr Val Ser Lys
465                 470                 475                 480
Ala Asp Ala Ala Ser Asn Lys Pro Gly Phe Lys Asp Ala Ala Asp His
                485                 490                 495
Pro Asp Asp Ala Thr Gln Cys Leu Phe Gly Glu Glu Leu Ser Leu Thr
            500                 505                 510
Ser Ser Asp Gln Gln Val Ile Gly Leu Ala Gly Lys Ala Thr Asp Met
        515                 520                 525
Ser Glu Ser Tyr Ser Arg Glu Ala Asn Lys Asp Leu Val Phe Met Asp
    530                 535                 540
Met Lys Lys Leu Ala Gln Phe Leu Ala Gly Lys Pro Glu His Pro Met
545                 550                 555                 560
Thr Arg Glu Thr Leu Asn Ala Glu Asn Ile Ala Lys Tyr Ala Phe Arg
                565                 570                 575
Ile Val Pro
```

<210> SEQ ID NO 5
<211> LENGTH: 1740
<212> TYPE: DNA
<213> ORGANISM: Pseudomonas syringae
<220> FEATURE:
<221> NAME/KEY: unsure
<222> LOCATION: (1100)
<223> OTHER INFORMATION: N at position 1100 can be A, C, T, or G

<400> SEQUENCE: 5

```
atggcgggta tcaatggagc gggaccatcg ggcgcttatt tgttggcca cacagacccc        60
gagccagcat cgggggggcgc acacggatcc agcagtggcg caagctcctc gaacagtccg       120
cgcttgccgg cgcctccgga tgcacccgcg tcgcaggcgc gagatcgacg cgaaatgctt       180
ttgcgagcca ggccgctgtc gcgccaaacc agggagtggg tggcgcaggg tatgccgcca       240
acggcggagg ctggagtgcc catcaggccg caggagtctg ccgaggctgc agcgccgcag       300
gcacgtgcag aggaaagaca cacgccggag gctgatgcag cagcgtcgca tgtacgcaca       360
gagggaggac gcacaccgca ggcgcttgcc ggtacctccc cacgccacac aggtgcggtg       420
ccacacgcca atagaattgt tcaacaattg gttgacgcgg gcgctgatct tgccggtatt       480
aacaccatga ttgacaatgc catgcgtcgc cacgcgatag ctcttccttc tcgaacagta       540
cagagtattt tgatcgagca tttccctcac ctgctagcgg gtgaactcat tagtggctca       600
gagctcgcta ccgcgttccg tgcggctctc cgtcgggagg ttcgccaaca ggaggcgtca       660
gccccccaa gaacaacagc gcggtcctcc gtaaggacgc cggagcggtc gacggtgccg       720
cccacttcta cggaatcatc atcgggcagc aaccagcgta cgttattagg gcggttcgcc       780
gggttgatga cgcctaatca gagacgtccg tcgagcgctt cgaacgcgtc tgcctctcaa       840
aggcctgtag acagaagccc gccacgcgta aaccaggtac ccacaggcgc taacagggtt       900
gtgatgcgta atcatggtaa taacgaggcc gacgccgcgc tgcaaggatt ggctcagcag       960
```

-continued

```
ggggttgata tggaggacct gcgcgccgcg cttgaaagac atatattgca tcgccgcccg    1020
atccccatgg atatagcgta cgccttgcag ggcgtgggca ttgcgccaag tatcgatacg    1080
ggagagagcc ttatggaaan cccgctgatg aatttgagtg ttgcgctgca ccgcgcacta    1140
gggcctcgtc ccgctcgtgc tcaagcgcct cgtccagccg ttccggtggc tcccgcgacc    1200
gtctccaggc gaccagatag cgcgcgtgcc acaagattgc aggtaatacc ggcgcgggag    1260
gattacgaaa ataatgtggc ctacggagtg cgcttgctga gcctgaatcc gggcgcgtgg    1320
gtcagggaga ctgttgcggc ctttgtaaac aaccgttacg agcggcaggc ggttgttgcc    1380
gacatacgcg cagcccctaa atttatctaaa caattcaata agttgcgtac ggtctctaag    1440
gccgatgctg cctccaataa accgggcttc aaggatctgg cggaccaccc agacgacgcg    1500
acgcaatgcc tttttggtga agaattgtcg ctgaccagtt cggttcagca ggtgatcggc    1560
ctggcaggta aggcaacgga catgtcggag tcttacagcc gagaggcaaa taaggacctg    1620
gtgttcatgg atatgaaaaa acttgcccaa ttcctcgcag gcaagcctga gcatccgatg    1680
accagagaaa cgcttaacgc cgaaaatatc gccaagtatg cttttagaat agtcccctga    1740
```

<210> SEQ ID NO 6
<211> LENGTH: 579
<212> TYPE: PRT
<213> ORGANISM: Pseudomonas syringae
<220> FEATURE:
<221> NAME/KEY: UNSURE
<222> LOCATION: (367)
<223> OTHER INFORMATION: Xaa at position 367 can be any amino acid

<400> SEQUENCE: 6

```
Met Ala Gly Ile Asn Gly Ala Gly Pro Ser Gly Ala Tyr Phe Val Gly
  1               5                  10                  15

His Thr Asp Pro Glu Pro Ala Ser Gly Gly Ala His Gly Ser Ser Ser
             20                  25                  30

Gly Ala Ser Ser Asn Ser Pro Arg Leu Pro Ala Pro Pro Asp Ala
         35                  40                  45

Pro Ala Ser Gln Ala Arg Asp Arg Arg Glu Met Leu Leu Arg Ala Arg
     50                  55                  60

Pro Leu Ser Arg Gln Thr Arg Glu Trp Val Ala Gln Gly Met Pro Pro
 65                  70                  75                  80

Thr Ala Glu Ala Gly Val Pro Ile Arg Pro Gln Ser Ala Glu Ala
                 85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
        115                 120                 125

Leu Ala Gly Thr Ser Pro Arg His Thr Gly Ala Val Pro His Ala Asn
    130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
            180                 185                 190

Ala Gly Glu Leu Ile Ser Gly Ser Glu Leu Ala Thr Ala Phe Arg Ala
        195                 200                 205

Ala Leu Arg Arg Glu Val Arg Gln Gln Glu Ala Ser Ala Pro Pro Arg
    210                 215                 220
```

-continued

```
Thr Thr Ala Arg Ser Ser Val Arg Thr Pro Glu Arg Ser Thr Val Pro
225                 230                 235                 240

Pro Thr Ser Thr Glu Ser Ser Ser Gly Ser Asn Gln Arg Thr Leu Leu
                245                 250                 255

Gly Arg Phe Ala Gly Leu Met Thr Pro Asn Gln Arg Arg Pro Ser Ser
            260                 265                 270

Ala Ser Asn Ala Ser Ala Ser Gln Arg Pro Val Asp Arg Ser Pro Pro
        275                 280                 285

Arg Val Asn Gln Val Pro Thr Gly Ala Asn Arg Val Val Met Arg Asn
    290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
            340                 345                 350

Gly Ile Ala Pro Ser Ile Asp Thr Gly Glu Ser Leu Met Glu Xaa Pro
        355                 360                 365

Leu Met Asn Leu Ser Val Ala Leu His Arg Ala Leu Gly Pro Arg Pro
    370                 375                 380

Ala Arg Ala Gln Ala Pro Arg Pro Ala Val Pro Val Ala Pro Ala Thr
385                 390                 395                 400

Val Ser Arg Arg Pro Asp Ser Ala Arg Ala Thr Arg Leu Gln Val Ile
                405                 410                 415

Pro Ala Arg Glu Asp Tyr Glu Asn Asn Val Ala Tyr Gly Val Arg Leu
            420                 425                 430

Leu Ser Leu Asn Pro Gly Ala Trp Val Arg Glu Thr Val Ala Ala Phe
        435                 440                 445

Val Asn Asn Arg Tyr Glu Arg Gln Ala Val Val Ala Asp Ile Arg Ala
    450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Leu Ala Asp His
                485                 490                 495

Pro Asp Asp Ala Thr Gln Cys Leu Phe Gly Glu Glu Leu Ser Leu Thr
            500                 505                 510

Ser Ser Val Gln Gln Val Ile Gly Leu Ala Gly Lys Ala Thr Asp Met
        515                 520                 525

Ser Glu Ser Tyr Ser Arg Glu Ala Asn Lys Asp Leu Val Phe Met Asp
    530                 535                 540

Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
                565                 570                 575

Ile Val Pro
```

<210> SEQ ID NO 7
<211> LENGTH: 1740
<212> TYPE: DNA
<213> ORGANISM: Pseudomonas syringae

<400> SEQUENCE: 7

```
atggcgggta tcaatggagc gggaccatcg ggcgcttatt ttgttggcca cacagacccc     60
```

-continued

```
gagccagcat cgggggcgc acacggatcc agcagtggcg caagctcctc gaacagtccg    120
cgcttgccgg cgcctccgga tgcacccgcg tcgcaggcgc gagatcgacg cgaaatgctt    180
ttgcgagcca ggccgctgtc gcgccaaacc agggagtggg tggcgcaggg tatgccgcca    240
acggcggagg ctggagtgcc catcaggccg caggagtctg ccgaggctgc agcgccgcag    300
gcacgtgcag aggaaagaca cacgccggag gctgatgcag cagcgtcgca tgtacgcaca    360
gagggaggac gcacaccgca ggcgcttgcc ggtacctccc cacgccacac aggtgcggtg    420
ccacacgcca atagaattgt caacaattg gttgacgcgg cgctgatct tgccggtatt    480 aacaccatga ttgacaatgc catgcgtcgc cacgcgatag ctcttccttc tcgaacagta    540
cagagtattt tgatcgagca tttccctcac ctgctagcgg gtgaactcat tagtggctca    600
gagctcgcta ccgcgttccg tgcggctctc cgtcgggagg ttcgccaaca ggaggcgtca    660 gccccccaa gaacagcagc gcggtcctcc gtaaggacgc cggagcggtc gacggtgccg    720
cccacttcta cggaatcatc atcgggcagc aaccagcgta cgttattagg gcggttcgcc    780
gggttgatga cgcctaatca gagacgtccg tcgagcgctt cgaacgcgtc tgcctctcaa    840
aggcctgtag acagaagccc gccacgcgta aaccaggtac ccacaggcgc taacagggtt    900
gtgatgcgta atcatggtaa taacgaggcc gacgccgcgc tgcaaggatt ggctcagcag    960
ggggttgata tggaggacct gcgcgccgcg cttgaaagac atatattgca tcgccgcccg   1020
atccccatgg atatagcgta cgccttgcag ggtgtgggca ttgcgccaag tatcgatacg   1080
ggagagagcc ttatggaaaa cccgctgatg aatttgagtg ttgcgctgca ccgcgcacta   1140
gggcctcgtc ccgctcgtgc tcaagcgcct cgtccagccg ttccggtggc tcccgcgacc   1200
gtctccaggc gaccagatag cgcgcgtgcc acaagattgc aggtaatacc ggcgcgggag   1260
gattacgaaa ataatgtggc ctacggagtg cgcttgctga gcctgaatcc gggcgcgggg   1320
gtcagggaga ctgttgcggc cttttgtaaac aaccgttacg agcggcaggc ggttgttgcc   1380
gacatacgcg cagccctaaa tttatctaaa caattcaata agttgcgtac ggtctctaag   1440
gccgatgctg cctccaataa accgggcttc aaggatctgg cggaccaccc agacgacgcg   1500
acgcaatgcc ttttttggtga agaattgtcg ctgaccagtt cggttcagca ggtgatcggc   1560
ctggcaggta aggcaacgga catgtcggag tcttacagcc gagaggcaaa taaggacctg   1620
gtgttcatgg atatgaaaaa acttgcccaa ttcctcgcag gcaagcctga gcatccgatg   1680
accagagaaa cgcttaacgc cgaaaatatc gccaagtatg cttttagaat agtcccctga   1740
```

<210> SEQ ID NO 8
<211> LENGTH: 579
<212> TYPE: PRT
<213> ORGANISM: Pseudomonas syringae

<400> SEQUENCE: 8

```
Met Ala Gly Ile Asn Gly Ala Gly Pro Ser Gly Ala Tyr Phe Val Gly
 1               5                  10                  15

His Thr Asp Pro Glu Pro Ala Ser Gly Gly Ala His Gly Ser Ser Ser
            20                  25                  30

Gly Ala Ser Ser Asn Ser Pro Arg Leu Pro Ala Pro Pro Asp Ala
        35                  40                  45

Pro Ala Ser Gln Ala Arg Asp Arg Arg Glu Met Leu Leu Arg Ala Arg
    50                  55                  60

Pro Leu Ser Arg Gln Thr Arg Glu Trp Val Ala Gln Gly Met Pro Pro
65                  70                  75                  80
```

-continued

```
Thr Ala Glu Ala Gly Val Pro Ile Arg Pro Gln Ser Ala Glu Ala
                 85                  90                  95

Ala Ala Pro Gln Ala Arg Ala Glu Glu Arg His Thr Pro Glu Ala Asp
            100                 105                 110

Ala Ala Ala Ser His Val Arg Thr Glu Gly Gly Arg Thr Pro Gln Ala
            115                 120                 125

Leu Ala Gly Thr Ser Pro Arg His Thr Gly Ala Val Pro His Ala Asn
            130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg His Ala Ile Ala Leu Pro
                165                 170                 175

Ser Arg Thr Val Gln Ser Ile Leu Ile Glu His Phe Pro His Leu Leu
                180                 185                 190

Ala Gly Glu Leu Ile Ser Gly Ser Glu Leu Ala Thr Ala Phe Arg Ala
                195                 200                 205

Ala Leu Arg Arg Glu Val Arg Gln Gln Glu Ala Ser Ala Pro Pro Arg
            210                 215                 220

Thr Ala Ala Arg Ser Ser Val Arg Thr Pro Glu Arg Ser Thr Val Pro
225                 230                 235                 240

Pro Thr Ser Thr Glu Ser Ser Ser Gly Ser Asn Gln Arg Thr Leu Leu
                245                 250                 255

Gly Arg Phe Ala Gly Leu Met Thr Pro Asn Gln Arg Arg Pro Ser Ser
                260                 265                 270

Ala Ser Asn Ala Ser Ala Ser Gln Arg Pro Val Asp Arg Ser Pro Pro
            275                 280                 285

Arg Val Asn Gln Val Pro Thr Gly Ala Asn Arg Val Val Met Arg Asn
            290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
                340                 345                 350

Gly Ile Ala Pro Ser Ile Asp Thr Gly Glu Ser Leu Met Glu Asn Pro
            355                 360                 365

Leu Met Asn Leu Ser Val Ala Leu His Arg Ala Leu Gly Pro Arg Pro
    370                 375                 380

Ala Arg Ala Gln Ala Pro Arg Pro Ala Val Pro Val Ala Pro Ala Thr
385                 390                 395                 400

Val Ser Arg Arg Pro Asp Ser Ala Arg Ala Thr Arg Leu Gln Val Ile
                405                 410                 415

Pro Ala Arg Glu Asp Tyr Glu Asn Asn Val Ala Tyr Gly Val Arg Leu
            420                 425                 430

Leu Ser Leu Asn Pro Gly Ala Gly Val Arg Glu Thr Val Ala Ala Phe
            435                 440                 445

Val Asn Asn Arg Tyr Glu Arg Gln Ala Val Val Ala Asp Ile Arg Ala
            450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Leu Ala Asp His
                485                 490                 495

Pro Asp Asp Ala Thr Gln Cys Leu Phe Gly Glu Glu Leu Ser Leu Thr
```

```
                  500                 505                 510
Ser Ser Val Gln Gln Val Ile Gly Leu Ala Gly Lys Ala Thr Asp Met
        515                 520                 525

Ser Glu Ser Tyr Ser Arg Glu Ala Asn Lys Asp Leu Val Phe Met Asp
    530                 535                 540

Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
                565                 570                 575

Ile Val Pro

<210> SEQ ID NO 9
<211> LENGTH: 16
<212> TYPE: PRT
<213> ORGANISM: Pseudomonas syringae

<400> SEQUENCE: 9

Ala Gly Pro Ser Gly Ala Tyr Phe Val Gly His Thr Asp Pro Glu Pro
1               5                  10                  15

<210> SEQ ID NO 10
<211> LENGTH: 9
<212> TYPE: PRT
<213> ORGANISM: Pseudomonas syringae

<400> SEQUENCE: 10

Ser Gly Ala Ser Ser Asn Ser Pro
1               5

<210> SEQ ID NO 11
<211> LENGTH: 8
<212> TYPE: PRT
<213> ORGANISM: Pseudomonas syringae

<400> SEQUENCE: 11

Leu Ser Arg Gln Thr Arg Glu Trp
1               5

<210> SEQ ID NO 12
<211> LENGTH: 6
<212> TYPE: PRT
<213> ORGANISM: Pseudomonas syringae

<400> SEQUENCE: 12

Ile Val Gln Gln Leu Val
1               5

<210> SEQ ID NO 13
<211> LENGTH: 5
<212> TYPE: PRT
<213> ORGANISM: Pseudomonas syringae

<400> SEQUENCE: 13

Ser Ser Ser Gly Ser
1               5

<210> SEQ ID NO 14
<211> LENGTH: 11
<212> TYPE: PRT
<213> ORGANISM: Pseudomonas syringae

<400> SEQUENCE: 14
```

```
Pro Val Asp Arg Ser Pro Pro Arg Val Asn Gln
 1               5                  10

<210> SEQ ID NO 15
<211> LENGTH: 12
<212> TYPE: PRT
<213> ORGANISM: Pseudomonas syringae

<400> SEQUENCE: 15

Ala Pro Arg Pro Ala Val Pro Val Ala Pro Ala Thr
 1               5                  10

<210> SEQ ID NO 16
<211> LENGTH: 5
<212> TYPE: PRT
<213> ORGANISM: Pseudomonas syringae

<400> SEQUENCE: 16

Ser Arg Arg Pro Asp
 1               5

<210> SEQ ID NO 17
<211> LENGTH: 5
<212> TYPE: PRT
<213> ORGANISM: Pseudomonas syringae

<400> SEQUENCE: 17

Arg Ala Thr Arg Leu
 1               5

<210> SEQ ID NO 18
<211> LENGTH: 15
<212> TYPE: PRT
<213> ORGANISM: Pseudomonas syringae

<400> SEQUENCE: 18

Arg Glu Asp Tyr Glu Asn Asn Val Ala Tyr Gly Val Arg Leu Leu
 1               5                  10                  15

<210> SEQ ID NO 19
<211> LENGTH: 5
<212> TYPE: PRT
<213> ORGANISM: Pseudomonas syringae

<400> SEQUENCE: 19

Val Ala Ala Phe Val
 1               5

<210> SEQ ID NO 20
<211> LENGTH: 5
<212> TYPE: PRT
<213> ORGANISM: Pseudomonas syringae

<400> SEQUENCE: 20

Ile Arg Ala Ala Leu
 1               5

<210> SEQ ID NO 21
<211> LENGTH: 5
<212> TYPE: PRT
<213> ORGANISM: Pseudomonas syringae

<400> SEQUENCE: 21

Ser Lys Ala Asp Ala
 1               5
```

<210> SEQ ID NO 22
<211> LENGTH: 8
<212> TYPE: PRT
<213> ORGANISM: Pseudomonas syringae

<400> SEQUENCE: 22

Gln Gln Val Ile Gly Leu Ala Gly
 1               5

<210> SEQ ID NO 23
<211> LENGTH: 38
<212> TYPE: PRT
<213> ORGANISM: Pseudomonas syringae

<400> SEQUENCE: 23

Phe Met Asp Met Lys Lys Leu Ala Gln Phe Leu Ala Gly Lys Pro Glu
 1               5                  10                  15

His Pro Met Thr Arg Glu Thr Leu Asn Ala Glu Asn Ile Ala Lys Tyr
            20                  25                  30

Ala Phe Arg Ile Val Pro
        35

<210> SEQ ID NO 24
<211> LENGTH: 553
<212> TYPE: PRT
<213> ORGANISM: Pseudomonas syringae
<220> FEATURE:
<221> NAME/KEY: UNSURE
<222> LOCATION: (1)..(6)
<223> OTHER INFORMATION: Xaa at positions 1-6 can be any amino acid
<220> FEATURE:
<221> NAME/KEY: UNSURE
<222> LOCATION: (23)..(31)
<223> OTHER INFORMATION: Xaa at positions 23-31 can be any amino acid
<220> FEATURE:
<221> NAME/KEY: UNSURE
<222> LOCATION: (41)..(70)
<223> OTHER INFORMATION: Xaa at positions 41-70 can be any amino acid
<220> FEATURE:
<221> NAME/KEY: UNSURE
<222> LOCATION: (79)..(131)
<223> OTHER INFORMATION: Xaa at positions 79-131 can be any amino acid
<220> FEATURE:
<221> NAME/KEY: UNSURE
<222> LOCATION: (138)..(220)
<223> OTHER INFORMATION: Xaa at positions 138-220 can be any amino acid
<220> FEATURE:
<221> NAME/KEY: UNSURE
<222> LOCATION: (226)..(253)
<223> OTHER INFORMATION: Xaa at positions 226-253 can be any amino acid
<220> FEATURE:
<221> NAME/KEY: UNSURE
<222> LOCATION: (265)..(360)
<223> OTHER INFORMATION: Xaa at positions 265-360 can be any amino acid
<220> FEATURE:
<221> NAME/KEY: UNSURE
<222> LOCATION: (373)
<223> OTHER INFORMATION: Xaa at position 373 can be any amino acid
<220> FEATURE:
<221> NAME/KEY: UNSURE
<222> LOCATION: (379)..(380)
<223> OTHER INFORMATION: Xaa at positions 379-380 can be any amino acid
<220> FEATURE:
<221> NAME/KEY: UNSURE
<222> LOCATION: (386)..(390)
<223> OTHER INFORMATION: Xaa at positions 386-390 can be any amino acid
<220> FEATURE:
<221> NAME/KEY: UNSURE
<222> LOCATION: (406)..(433)
<223> OTHER INFORMATION: Xaa at positions 406-433 can be any amino acid
<220> FEATURE:

```
<221> NAME/KEY: UNSURE
<222> LOCATION: (439)..(451)
<223> OTHER INFORMATION: Xaa at positions 439-451 can be any amino acid
<220> FEATURE:
<221> NAME/KEY: UNSURE
<222> LOCATION: (457)..(489)
<223> OTHER INFORMATION: Xaa at positions 457-489 can be any amino acid
<220> FEATURE:
<221> NAME/KEY: UNSURE
<222> LOCATION: (498)..(515)
<223> OTHER INFORMATION: Xaa at positions 498-515 can be any amino acid

<400> SEQUENCE: 24

Xaa Xaa Xaa Xaa Xaa Xaa Ala Gly Pro Ser Gly Ala Tyr Phe Val Gly
  1               5                  10                  15

His Thr Asp Pro Glu Pro Xaa Xaa Xaa Xaa Xaa Xaa Xaa Xaa Xaa Ser
             20                  25                  30

Gly Ala Ser Ser Ser Asn Ser Pro Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Leu Ser Arg Gln Thr Arg Glu Trp Xaa Xaa
 65                  70                  75                  80

Xaa Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Ile Val Gln Gln Leu Val Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Ser Ser Gly
            210                 215                 220

Ser Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Pro Val Asp
            245                 250                 255

Arg Ser Pro Pro Arg Val Asn Gln Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350
```

Xaa Xaa Xaa Xaa Xaa Xaa Xaa Ala Pro Arg Pro Ala Val Pro Val
            355                 360                 365

Ala Pro Ala Thr Xaa Ser Arg Arg Pro Asp Xaa Xaa Arg Ala Thr Arg
    370                 375                 380

Leu Xaa Xaa Xaa Xaa Xaa Arg Glu Asp Tyr Glu Asn Asn Val Ala Tyr
385                 390                 395                 400

Gly Val Arg Leu Leu Xaa Xaa Xaa Xaa Xaa Xaa Xaa Xaa Xaa Xaa Xaa
                405                 410                 415

Val Ala Ala Phe Val Xaa Xaa Xaa Xaa Xaa Xaa Xaa Xaa Xaa Xaa Xaa
            420                 425                 430

Xaa Ile Arg Ala Ala Leu Xaa Xaa Xaa Xaa Xaa Xaa Xaa Xaa Xaa Xaa
            435                 440                 445

Xaa Xaa Xaa Ser Lys Ala Asp Ala Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Gln Gln Val Ile Gly Leu Ala
                485                 490                 495

Gly Xaa Xaa Xaa Xaa Xaa Xaa Xaa Xaa Xaa Xaa Xaa Xaa Xaa Xaa Xaa
            500                 505                 510

Xaa Xaa Xaa Phe Met Asp Met Lys Lys Leu Ala Gln Phe Leu Ala Gly
            515                 520                 525

Lys Pro Glu His Pro Met Thr Arg Glu Thr Leu Asn Ala Glu Asn Ile
530                 535                 540

Ala Lys Tyr Ala Phe Arg Ile Val Pro
545                 550

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 25
gtaatgcagc gcctccctat c                                           21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 26 tcagggact attctaaaag c                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 27
atggcgggta tcaatagagc g                                           21

<210> SEQ ID NO 28
<211> LENGTH: 23

```
<212> TYPE: DNA
<213> ORGANISM: Artificial Sequence
<220> FEATURE:
<223> OTHER INFORMATION: Description of Artificial Sequence: primer

<400> SEQUENCE: 28
tcacacccgc aatcgtgttg cac                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 29
tcatacatgt ctttcaaggg ccg                                              23

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 30
gtatcaatag agcgggacca tc                                               22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 31
cactgaccac ttgctgaacg                                                  20

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 32
tgtcgcgcca aaccagggcg tg                                               22

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 33
ccatcaccag ggcaaacc                                                    18

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 34
```
gtatcgttca gcaattggtc agtg                                          24

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 35
acgcgtatgg gtctttggtt g                                             21

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 36
acgattgcgg gtgatgc                                                  17

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 37
cctcttggct gtaaggctgc                                               20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 38
atggcgggta tcaatagagc gg                                            22

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 39
gaattcgata tcaagcttat cgataccgtc gacctcgag                          39

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 40
gaattcgaat tgggatatca agcttatcga taccgtcgac ctcgag                  46

<210> SEQ ID NO 41
<211> LENGTH: 44
<212> TYPE: DNA
<213> ORGANISM: Artificial Sequence

```
<220> FEATURE:
<223> OTHER INFORMATION: Description of Artificial Sequence:  primer

<400> SEQUENCE: 41
gaattcgaat tgatatcaag cttatcgata ccgtcgacct cgag                44

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:  primer

<400> SEQUENCE: 42
cggaggcgaa cagccgagca g                                         21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 43
gcaattcgaa gtggcagtga                                           20

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence:  primer

<400> SEQUENCE: 44
ttatgcttta ttggtatttt tagagg                                    26

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 45
atggcgggta tcaatagagc                                           20

<210> SEQ ID NO 46
<211> LENGTH: 26
<212> TYPE: DNA
<213> ORGANISM: Pseudomonas syringae
<220> FEATURE:
<221> NAME/KEY: unsure
<222> LOCATION: (7)..(22)
<223> OTHER INFORMATION: N at positions 7-22 can be A, C, T, or G

<400> SEQUENCE: 46
ggaactnnnn nnnnnnnnnn nnccac                                    26

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:  primer

<400> SEQUENCE: 47
```

```
Met Ala Gly Ile Asn Arg Ala Gly
  1               5
```

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: UNSURE
<222> LOCATION: (2)
<223> OTHER INFORMATION: Xaa at position 2 can be any amino acid except
      E
<220> FEATURE:
<221> NAME/KEY: UNSURE
<222> LOCATION: (3)
<223> OTHER INFORMATION: Xaa at position 3 can be any amino acid except
      D
<220> FEATURE:
<221> NAME/KEY: UNSURE
<222> LOCATION: (4)
<223> OTHER INFORMATION: Xaa at position 4 can be any amino acid except
      R
<220> FEATURE:
<221> NAME/KEY: UNSURE
<222> LOCATION: (5)
<223> OTHER INFORMATION: Xaa at position 5 can be any amino acid except
      K
<220> FEATURE:
<221> NAME/KEY: UNSURE
<222> LOCATION: (6)
<223> OTHER INFORMATION: Xaa at position 6 can be any amino acid except
      H
<220> FEATURE:
<221> NAME/KEY: UNSURE
<222> LOCATION: (7)
<223> OTHER INFORMATION: Xaa at position 7 can be any amino acid except
      P
<220> FEATURE:
<221> NAME/KEY: UNSURE
<222> LOCATION: (8)
<223> OTHER INFORMATION: Xaa at position 8 can be any amino acid except
      F
<220> FEATURE:
<221> NAME/KEY: UNSURE
<222> LOCATION: (9)
<223> OTHER INFORMATION: Xaa at position 9 can be any amino acid except
      Y
<220> FEATURE:
<221> NAME/KEY: UNSURE
<222> LOCATION: (10)
<223> OTHER INFORMATION: Xaa at position 10 can be any amino acid except
      W
<220> FEATURE:
<221> NAME/KEY: UNSURE
<222> LOCATION: (11)..(12)
<223> OTHER INFORMATION: Xaa at positions 11-12 can be any amino acid
<220> FEATURE:
<221> NAME/KEY: UNSURE
<222> LOCATION: (19)
<223> OTHER INFORMATION: Xaa at position 19 can be any amino acid except
      P

<400> SEQUENCE: 48

```
Gly Xaa Xaa Xaa Xaa Xaa Xaa Xaa Xaa Xaa Xaa Xaa Ser Thr Ala Gly
  1               5                  10                  15

Cys Asn Xaa
```

<210> SEQ ID NO 49
<211> LENGTH: 16
<212> TYPE: PRT
<213> ORGANISM: Artificial Sequence
<220> FEATURE:

```
<223> OTHER INFORMATION: Description of Artificial Sequence:  consensus
      sequence
<220> FEATURE:
<221> NAME/KEY: UNSURE
<222> LOCATION: (2)..(3)
<223> OTHER INFORMATION: Xaa at positions 2-3 can be any amino acid
<220> FEATURE:
<221> NAME/KEY: UNSURE
<222> LOCATION: (5)..(6)
<223> OTHER INFORMATION: Xaa at positions 5-6 can be any amino acid
<220> FEATURE:
<221> NAME/KEY: UNSURE
<222> LOCATION: (8)..(9)
<223> OTHER INFORMATION: Xaa at positions 8-9 can be any amino acid
<220> FEATURE:
<221> NAME/KEY: UNSURE
<222> LOCATION: (11)
<223> OTHER INFORMATION: Xaa at position 11 can be any amino acid
<220> FEATURE:
<221> NAME/KEY: UNSURE
<222> LOCATION: (13)..(15)
<223> OTHER INFORMATION: Xaa at positions 13-15 can be any amino acid

<400> SEQUENCE: 49

Arg Xaa Xaa Leu Xaa Xaa Ser Xaa Xaa Leu Xaa Arg Xaa Xaa Xaa Glu
 1               5                  10                  15

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence:  consensus
      sequence
<220> FEATURE:
<221> NAME/KEY: UNSURE
<222> LOCATION: (2)
<223> OTHER INFORMATION: Xaa at position 2 can be any amino acid
<220> FEATURE:
<221> NAME/KEY: UNSURE
<222> LOCATION: (4)
<223> OTHER INFORMATION: Xaa at position 4 can be any amino acid

<400> SEQUENCE: 50

Ser Xaa Arg Xaa Arg
 1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence:  consensus
      sequence
<220> FEATURE:
<221> NAME/KEY: UNSURE
<222> LOCATION: (4)..(8)
<223> OTHER INFORMATION: Xaa at positions 4-8 can be any amino acid

<400> SEQUENCE: 51

Asn Pro Ser Xaa Xaa Xaa Xaa Xaa Ser
 1               5

<210> SEQ ID NO 52
<211> LENGTH: 539
<212> TYPE: PRT
<213> ORGANISM: Pseudomonas syringae

<400> SEQUENCE: 52

Met Pro Gly Ile Asn Gly Ala Gly Pro Ser Asn Phe Phe Trp Gln Trp
 1               5                  10                  15
```

-continued

```
Arg Thr Asp Gly Glu Pro Val Thr Glu Arg Glu His Asp Ser Ser Arg
             20                  25                  30

Ser Ala Ser Ser Ala Asn Ser Pro Glu Leu Pro Pro Ala Ser Pro
         35                  40                  45

Ala Glu Ser Gly Arg Gln Arg Leu Leu Arg Ser Ala Leu Ser Arg
     50                  55                  60

Gln Thr Arg Glu Trp Leu Glu Ala Thr Pro Ala Arg Val Gln Gly Ala
 65                  70                  75                  80

Thr Pro Pro Ala Glu Ala Arg Gln Ser Pro Glu Ala Gln Gln Ala Glu
                 85                  90                  95

Arg Ile Val Gln Glu Leu Val Arg Gly Gly Ala Asp Leu Asn Asn Val
            100                 105                 110

Arg Thr Met Leu Arg Asn Val Met Asp Asn Asn Ala Val Ala Phe Ser
            115                 120                 125

Arg Val Glu Arg Asp Ile Leu Leu Gln His Phe Pro Asn Met Pro Met
        130                 135                 140

Thr Gly Ile Ser Ser Asp Ser Val Leu Ala Asn Glu Leu Arg Gln Arg
145                 150                 155                 160

Leu Arg Gln Thr Val Arg Gln Gln Arg Ile Gln Ser Ser Thr Pro Ala
                165                 170                 175

Arg Leu Ala Asp Ser Ser Ser Gly Ser Ser Gln Arg Ser Leu Ile Gly
            180                 185                 190

Arg Ser Thr Met Leu Met Thr Pro Gly Arg Ser Ser Ser Ser Ser Ala
        195                 200                 205

Ala Ala Ser Arg Thr Ser Val Asp Arg His Pro Gln Gly Leu Asp Leu
    210                 215                 220

Glu Ser Ala Arg Leu Ala Ser Ala Ala Arg His Asn His Ser Ala Asn
225                 230                 235                 240

Gln Thr Asn Glu Ala Leu Arg Arg Leu Thr Gln Glu Gly Val Asp Met
                245                 250                 255

Glu Arg Leu Arg Thr Ser Leu Gly Arg Tyr Ile Met Ser Leu Glu Pro
            260                 265                 270

Leu Pro Pro Asp Leu Arg Arg Ala Leu Glu Ser Val Gly Ile Asn Pro
        275                 280                 285

Phe Ile Pro Glu Glu Leu Ser Leu Val Asp His Pro Val Leu Asn Phe
    290                 295                 300

Ser Ala Ala Leu Asn Arg Met Leu Ala Ser Arg Gln Thr Thr Thr Asn
305                 310                 315                 320

Ser Pro Glu Leu Pro Pro Leu Ala Ser Ser Ala Glu Ser Gly Arg Arg
                325                 330                 335

Arg Leu Leu Arg Ser Pro Pro Leu Leu Ser Gly Gln Arg Glu Trp Ile
            340                 345                 350

Glu Gln Ser Met Arg Gln Glu Ala Glu Pro Gln Ser Ser Arg Leu Asn
        355                 360                 365

Arg Ala Val Arg Leu Ala Val Met Pro Pro Gln Asn Glu Asn Glu Asp
    370                 375                 380

Asn Val Ala Tyr Ala Ile Arg Leu Arg Arg Leu Asn Pro Gly Ala Asp
385                 390                 395                 400

Val Ser Arg Val Val Ala Ser Phe Ile Thr Asp Pro Ala Ala Arg Gln
                405                 410                 415

Gln Val Val Asn Asp Ile Arg Ala Ala Leu Asp Ile Ala Pro Gln Phe
            420                 425                 430

Ser Gln Leu Arg Thr Ile Ser Lys Ala Asp Ala Glu Ser Glu Glu Leu
```

-continued

```
                435                 440                 445
Gly Phe Arg Asp Ala Ala Asp His Pro Asp Asn Ala Thr Ser Cys Leu
    450                 455                 460

Phe Gly Glu Glu Leu Ser Leu Ser Asn Pro Asp Gln Gln Val Ile Gly
465                 470                 475                 480

Leu Ala Val Asn Pro Thr Asp Lys Pro Gln Pro Tyr Ser Gln Glu Val
                485                 490                 495

Asn Lys Ala Leu Thr Phe Met Asp Met Lys Lys Leu Ala Gln Tyr Leu
            500                 505                 510

Ala Asp Lys Pro Glu His Pro Leu Asn Arg Gln Arg Leu Asp Ala Lys
        515                 520                 525

Asn Ile Ala Lys Tyr Ala Phe Lys Ile Val Pro
    530                 535

<210> SEQ ID NO 53
<211> LENGTH: 158
<212> TYPE: PRT
<213> ORGANISM: Pseudomonas syringae

<400> SEQUENCE: 53

Met Gly Asn Ile Cys Val Gly Gly Ser Arg Met Ala His Gln Val Asn
1               5                   10                  15

Ser Pro Asp Arg Val Ser Asn Asn Ser Gly Asp Glu Asp Asn Val Thr
            20                  25                  30

Ser Ser Gln Leu Leu Ser Val Arg His Gln Leu Ala Glu Ser Ala Gly
        35                  40                  45

Leu Pro Arg Asp Gln His Glu Phe Val Ser Ser Gln Ala Pro Gln Ser
    50                  55                  60

Leu Arg Asn Arg Tyr Asn Asn Leu Tyr Ser His Thr Gln Arg Thr Leu
65                  70                  75                  80

Asp Met Ala Asp Met Gln His Arg Tyr Met Thr Gly Ala Ser Gly Ile
                85                  90                  95

Asn Pro Gly Met Leu Pro His Glu Asn Val Asp Asp Met Arg Ser Ala
            100                 105                 110

Ile Thr Asp Trp Ser Asp Met Arg Glu Ala Leu Gln His Ala Met Gly
        115                 120                 125

Ile His Ala Asp Ile Pro Pro Ser Pro Glu Arg Phe Val Ala Thr Met
    130                 135                 140

Asn Pro Ser Gly Ser Ile Arg Met Ser Thr Leu Ser Pro Ser
145                 150                 155

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence:  consensus
      sequence
<220> FEATURE:
<221> NAME/KEY: UNSURE
<222> LOCATION: (2)
<223> OTHER INFORMATION: Xaa at position 2 can be any amino acid
<220> FEATURE:
<221> NAME/KEY: UNSURE
<222> LOCATION: (4)..(5)
<223> OTHER INFORMATION: Xaa at positions 4-5 can be any amino acid
<220> FEATURE:
<221> NAME/KEY: UNSURE
<222> LOCATION: (7)..(8)
<223> OTHER INFORMATION: Xaa at positions 7-8 can be any amino acid
<220> FEATURE:
```

```
<221> NAME/KEY: UNSURE
<222> LOCATION: (10)..(11)
<223> OTHER INFORMATION: Xaa at positions 10-11 can be any amino acid
<220> FEATURE:
<221> NAME/KEY: UNSURE
<222> LOCATION: (13)
<223> OTHER INFORMATION: Xaa at position 13 can be any amino acid
<220> FEATURE:
<221> NAME/KEY: UNSURE
<222> LOCATION: (15)..(17)
<223> OTHER INFORMATION: Xaa at positions 15-17 can be any amino acid

<400> SEQUENCE: 54

Ser Xaa Arg Xaa Xaa Leu Xaa Xaa Ser Xaa Xaa Leu Xaa Arg Xaa Xaa
 1               5                  10                  15

Xaa Glu
```